(12) United States Patent
Inoue et al.

(10) Patent No.: US 9,200,022 B2
(45) Date of Patent: Dec. 1, 2015

(54) ORGANIC LIGHT-EMITTING ELEMENT, ORGANOMETALLIC COMPLEX, LIGHT-EMITTING DEVICE, ELECTRONIC APPLIANCE, AND LIGHTING DEVICE

(75) Inventors: Hideko Inoue, Kanagawa (JP); Hiromi Nowatari, Kanagawa (JP); Satoshi Seo, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 461 days.

(21) Appl. No.: 13/446,216

(22) Filed: Apr. 13, 2012

(65) Prior Publication Data
US 2012/0264936 A1 Oct. 18, 2012

(30) Foreign Application Priority Data
Apr. 15, 2011 (JP) ................................ 2011-091514

(51) Int. Cl.
C07F 15/00 (2006.01)

(52) U.S. Cl.
CPC .......... *C07F 15/0033* (2013.01); *C07F 15/0086* (2013.01)

(58) Field of Classification Search
CPC .......................... C07F 15/0033; C07F 15/0086
USPC ........................................................ 544/225
See application file for complete search history.

(56) References Cited

U.S. PATENT DOCUMENTS

| 7,901,792 | B2 | 3/2011 | Egawa et al. |
| 7,960,038 | B2 | 6/2011 | Ohsawa et al. |
| 7,993,494 | B2 | 8/2011 | Inoue et al. |
| 8,084,145 | B2 | 12/2011 | Inoue et al. |
| 8,173,277 | B2 | 5/2012 | Egawa et al. |
| 8,623,523 | B2 | 1/2014 | Egawa et al. |
| 2007/0129545 | A1 | 6/2007 | Inoue et al. |
| 2008/0149923 | A1 | 6/2008 | Ohsawa et al. |
| 2008/0233432 | A1 | 9/2008 | Inoue et al. |
| 2008/0286604 | A1 | 11/2008 | Inoue et al. |
| 2008/0305361 | A1 | 12/2008 | Inoue et al. |
| 2008/0312437 | A1 | 12/2008 | Inoue et al. |
| 2009/0015143 | A1 | 1/2009 | Inoue et al. |
| 2009/0039776 | A1 | 2/2009 | Yamada et al. |
| 2010/0145044 | A1 | 6/2010 | Inoue et al. |
| 2010/0181905 | A1 | 7/2010 | Inoue et al. |
| 2010/0219407 | A1 | 9/2010 | Kamatani et al. |
| 2011/0082296 | A1 | 4/2011 | Inoue et al. |
| 2011/0187265 | A1 | 8/2011 | De Cola et al. |
| 2011/0245495 | A1 | 10/2011 | Inoue et al. |
| 2011/0298360 | A1 | 12/2011 | Ohsawa et al. |

FOREIGN PATENT DOCUMENTS

| CN | 001866576 A | 11/2006 |
| CN | 101263126 A | 9/2008 |
| CN | 102099365 A | 6/2011 |
| JP | 2009-23938 | 2/2009 |
| JP | 2009-40728 | 2/2009 |
| JP | 2009-114137 | 5/2009 |
| JP | 2011-528328 | 11/2011 |
| JP | 2012-4526 | 1/2012 |
| KR | 10-2011-0440941 | 4/2011 |
| TW | I231157 B | 4/2005 |
| WO | WO 00/70655 A2 | 11/2000 |
| WO | WO 2007/032258 A1 | 3/2007 |
| WO | WO 2009/011447 A2 | 1/2009 |
| WO | WO 2009/060995 A1 | 5/2009 |
| WO | WO 2010/007107 A1 | 1/2010 |
| WO | WO 2012/128188 | * 9/2012 |

OTHER PUBLICATIONS

Iridium, Chapter 31, Comprehensive Analytical Chemistry, vol. 30, pp. 465-471 (1996).*
Platinum, Chapter 42, Comprehensive Analytical Chemistry, vol. 30, pp. 589-600 (1996).*
Crossley, The Organometallic Chemistry of Group 9 Poly(pyrazolyl)borate complexes, Advances in Organometallic Chemistry, vol. 56, pp. 199-321 (2008).*
Merola, Iridium: Organometallic Chemistry, Encyclopedia of Inorganic Chemistry, pp. 1-18, 2006.*
Mydlak, M. et al, "Positively Charged Iridium (III) Triazole Derivatives as Blue Emitters for Light-Emitting Electrochemical Cells," Advanced Functional Materials, vol. 20, No. 11, 2010, pp. 1812-1820.
International Search Report re application No. PCT/JP2012/059829, dated Jul. 3, 2012.
Written Opinion re Application No. PCT/JP2012/059829, dated Jul. 3, 2012.
Bredereck, H. et al., Formamide-Reactions, VIII, A New Pyrimidine-Synthesis, Chem. Ber. (Chemische Berichte), vol. 90, 1957, pp. 942-952 (English translation, pp. 1-17).
Bredereck, H. et al., "Formamide Reactions, VIII. EINE NEUE Pyrimidin-Synthese," Chem.Ber. (Chemische Berichte), vol. 90, 1957, pp. 942-952 (in German).
Chinese Ofice Action re Application No. CN 201280018708.9, dated Aug. 5, 2015.

* cited by examiner

*Primary Examiner* — Deepak Rao
(74) *Attorney, Agent, or Firm* — Husch Blackwell LLP

(57) ABSTRACT

Disclosed is a phosphorescent organometallic complex having: a 6-membered aromatic heterocycle having a nitrogen atom; iridium or platinum to which the nitrogen atom coordinates; and an aryl group which is bonded to an α-carbon of the nitrogen atom and is ortho-metalated with the iridium or platinum, where at least one of the aromatic heterocycle and the aryl group has an alicyclic hydrocarbon having an intramolecular carbon-carbon bridged bond as a substituent. The ability of the bulky structure of the alicyclic hydrocarbon to inhibit aggregation of the organometallic complex, concerted with the strong electron-donating property of the alicyclic hydrocarbon to the aromatic heterocycle or the aryl group, contributes to the increase in absorption coefficient and phosphorescent efficiency of the organometallic complex. The improved absorption coefficient and the phosphorescent efficiency allow the formation of a light-emitting element with excellent external quantum efficiency over 25%.

11 Claims, 20 Drawing Sheets

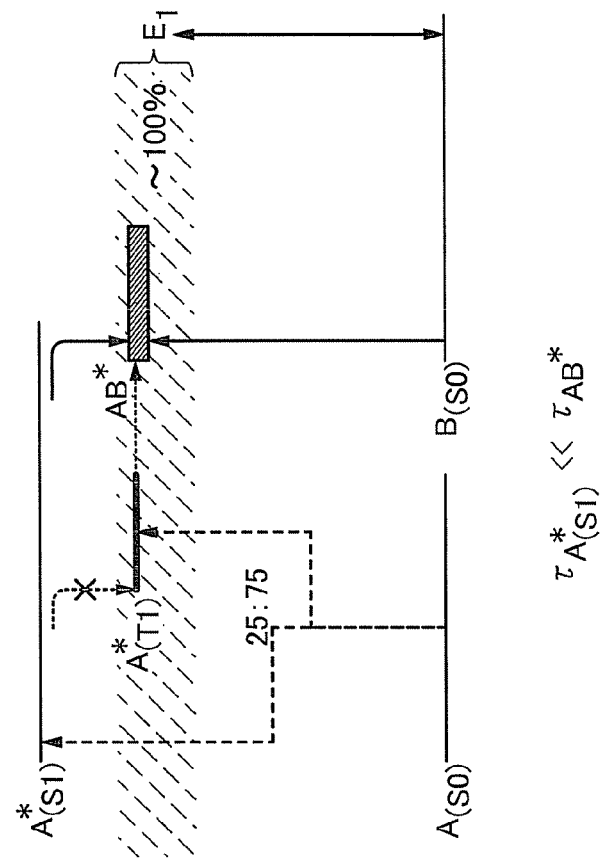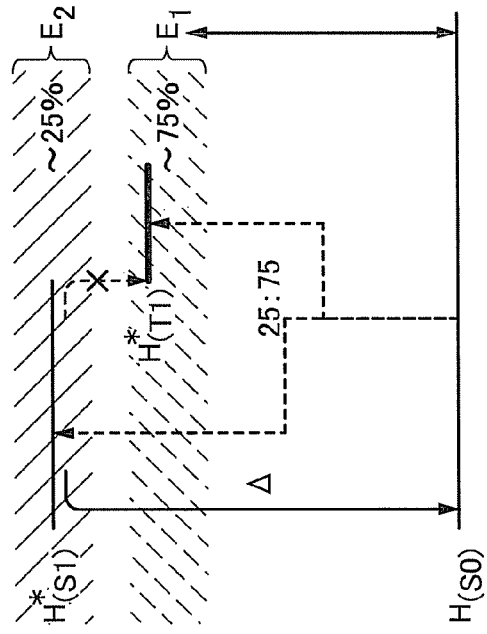

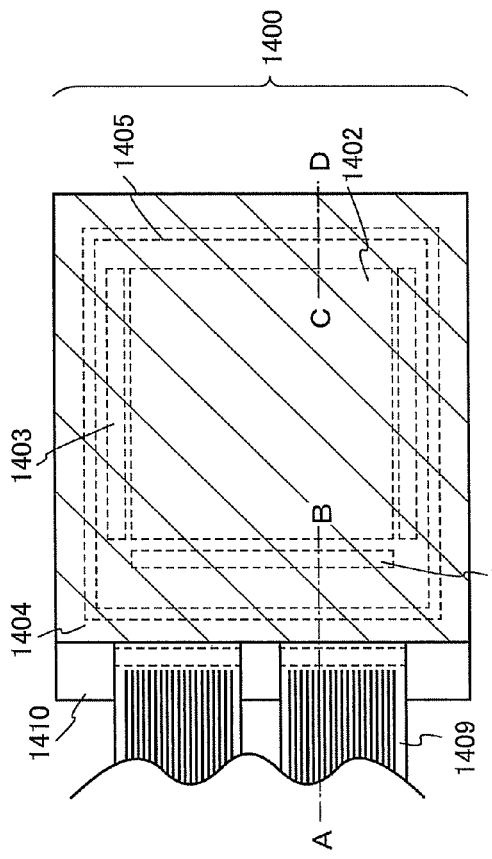
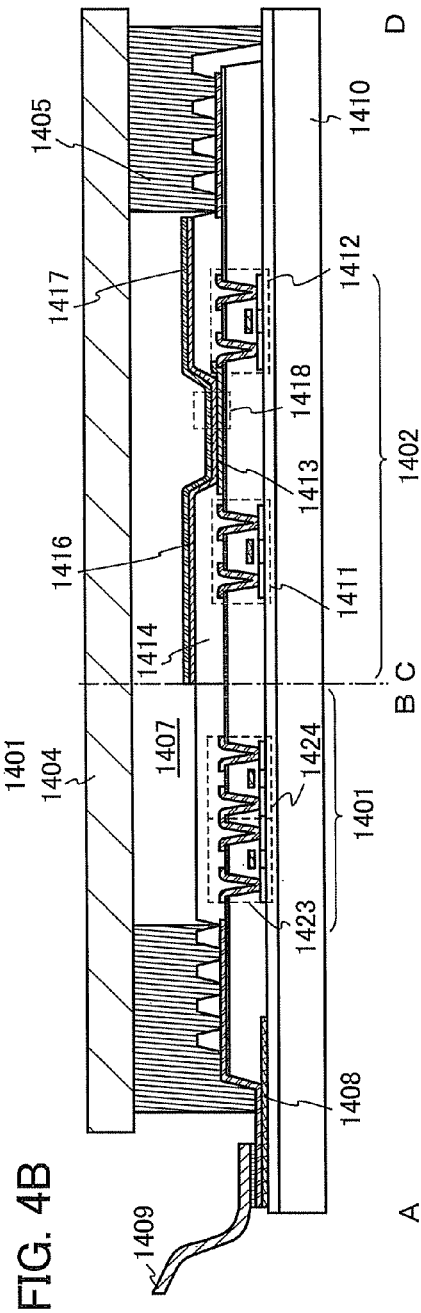
FIG. 4A
FIG. 4B

US 9,200,022 B2

ORGANIC LIGHT-EMITTING ELEMENT, ORGANOMETALLIC COMPLEX, LIGHT-EMITTING DEVICE, ELECTRONIC APPLIANCE, AND LIGHTING DEVICE

TECHNICAL FIELD

The present invention relates to an organic light-emitting element or an organometallic complex. The invention further relates to a light-emitting device, an electronic appliance, or a lighting device including any of the organic light-emitting element and the organometallic complex.

BACKGROUND ART

As an example of an element containing an organic compound, a light-emitting element containing a light-emitting organic compound or light-emitting inorganic compound as a light-emitting material has been developed. For example, a light-emitting element called EL (electroluminescent) element having a simple structure in which a light-emitting layer containing a light-emitting material is provided between a pair of electrodes has been studied.

Owing to the simple structure, a thinner and lighter EL element can be easily prepared. Further, the EL element has capabilities for high-speed response with respect to input signals, driving with a DC power at a relatively low voltage (about several volts to several tens of volts), and formation in a large-area film form and thus has been applied to a display device and a lighting device.

In the EL element, from a pair of electrodes between which a light-emitting layer is interposed, electrons and holes are injected to be recombined in the light-emitting layer. Thus, energy is generated and used for exciting a light-emitting substance in the light-emitting layer. The excited light-emitting substance emits light when relaxing to a ground state, whereby the light is extracted and used.

A light-emitting substance can have two types of the excited states: a singlet excited state (S*) and a triplet excited state (T*). The statistical generation ratio thereof in a light emitting element is considered to be S*:T*=1:3.

For a compound that emits light from the singlet excited state (hereinafter, the compound will be referred to as fluorescent compound) at room temperature, only emission from the singlet excited state (fluorescence) is observed, and no emission from the triplet excited state (phosphorescence) is observed. The internal quantum efficiency (the ratio of generated photons to injected carriers) in a light-emitting element containing a fluorescent compound is assumed to have a theoretical limit of 25% based on S*:T*=1:3.

On the other hand, the internal quantum efficiency of the EL element utilizing a compound that emits light from the triplet excited state (hereinafter, the compound will be referred to as phosphorescent compound) can be increased to 75% to 100% in theory, considering intersystem crossing from a singlet excited state to a triplet excited state. In other words, emission efficiency can be 3 to 4 times as much as that of the EL element utilizing the fluorescent compound. Therefore, the light-emitting element containing a phosphorescent compound has been actively developed in recent years in order to achieve a high-efficiency light-emitting element. As the phosphorescent compound, an organometallic complex that has iridium or the like as a central metal have particularly attracted attention owing to their high phosphorescence quantum yield; for example, an organometallic complex that has iridium as a central metal is disclosed as a phosphorescent material in Patent Document 1.

REFERENCE

Patent Document

[Patent Document 1] PCT International Publication No. 2000/070655

DISCLOSURE OF INVENTION

Even an organic light-emitting element containing a phosphorescent compound still needs to be improved because the internal quantum efficiency has not yet been increased to the theoretical limit.

An embodiment of the invention is made in view of the foregoing technical background. Thus, an object is to provide an organic light-emitting element with high emission efficiency. Another object is to provide an organometallic complex with high emission efficiency. Another object is to provide a light-emitting element with high emission efficiency. Another object is to provide a light-emitting device with high emission efficiency and low power consumption. Another object is to provide an electronic appliance with low power consumption. Another object is to provide a lighting device with low power consumption.

To achieve the above objects, the inventors investigated a method to increase the emission efficiency of an organic light-emitting element without prolongation of the emission wavelength, which led to an concept to increase a molecular absorption coefficient or difficulty in aggregation of a phosphorescent compound contained in an organic light-emitting element. That is, the inventors studied a structure in which the absorption coefficient of a phosphorescent organometallic iridium complex is increased by donating an electron to a ligand of the phosphorescent compound without leading to prolongation of the emission wavelength owing to a resonance effect (also referred to as R effect), or a structure in which bulkiness of the ligand is increased to suppress the aggregation. As a result, focus is placed on an alicyclic substituent having an electron-donating inductive effect (also referred to as I effect) and a bulky structure, which led to a structure of an organic light-emitting element containing a phosphorescent organometallic complex in which a carbon of nitrogen, which coordinates to iridium or platinum, of a nitrogen-containing 6-membered aromatic heterocycle, such as pyridine or monocyclic diazine, is bonded to an ortho-metalated aryl group, and in which the 6-membered aromatic heterocycle or the aryl group has an alicyclic hydrocarbon having an intramolecular carbon-carbon bridged bond such as a tricyclo[5.2.1.0(2,6)]decanyl group, a norbornyl group, and an adamantyl group. Thus, the aforementioned objects are achieved.

That is, an embodiment of the invention is an organic light-emitting element containing a phosphorescent organometallic complex which includes a metal and a 6-membered aromatic heterocycle having a nitrogen atom coordinating to the metal. The metal is iridium or platinum. Further, an aryl group is bonded to an α-carbon atom of the nitrogen atom, and the aryl group is ortho-metalated by bonding to the metal. Furthermore, the 6-membered aromatic heterocycle or the aryl group has, as a substituent, an alicyclic hydrocarbon having an intramolecular carbon-carbon bridged bond. The 6-membered aromatic heterocycle is preferably pyridine or monocyclic diazine, and the alicyclic hydrocarbon is preferably a tricyclo[5.2.1.0(2,6)]decanyl group, a norbornyl group, or an adamantyl group. Note that, in the specification, a 6-membered aromatic heterocycle having a nitrogen atom means that at least one of the atoms which form the ring of the aromatic heterocycle is a nitrogen atom.

The alicyclic hydrocarbon such as tricyclo[5.2.1.0(2,6)] decanyl group, the norbornyl group, and the adamantyl group, which is bonded to the ligand of the phosphorescent organometallic complex, does not cause the prolongation of the emission wavelength owing to the resonance effect and donates an electron to the ligand owing to the inductive effect. The phosphorescent organometallic complex including the ligand to which an electron is donated has a high molecular absorption coefficient; thus, when it is dispersed in a host material, energy can be received from the host material efficiently. Alternatively, with the use of the phosphorescent organometallic complex including the ligand which has a bulky alicyclic hydrocarbon such as tricyclo[5.2.1.0(2,6)]decanyl group, the norbornyl group, and the adamantyl group, concentration quenching is unlikely to occur because the increased intermolecular distance inhibits the aggregation.

With the use of such a phosphorescent organometallic complex, an organic light-emitting element with high emission efficiency can be provided.

As to the aforementioned phosphorescent organometallic complex used in an embodiment of the invention, the lowest triplet excited state of the phosphorescent organometallic complex is formed with the metal-ligand bonding structure, so that phosphorescence due to the metal-ligand bonding structure can be obtained. Thus, high emission efficiency can be obtained.

Another embodiment of the invention is the above-described organic light-emitting element containing the phosphorescent organometallic complex in which the aryl group is selected from substituted or unsubstituted phenyl, biphenyl, and naphthyl groups.

In the phosphorescent organometallic complex having such a structure, the phenomenon of the emission-wavelength prolongation (also called red shift) is suppressed, and red, yellow, or green light can be emitted with high efficiency. With the use of such a phosphorescent organometallic complex, an organic light-emitting element with high emission efficiency can be provided.

Another embodiment of the invention is an organic light-emitting element containing a phosphorescent organometallic complex which has a structure represented by the following general formula (G1). Further, the phosphorescent organometallic complex includes a metal M which is iridium or platinum and a pyrimidine ring coordinating to the metal M. Furthermore, a phenyl group is bonded to an α-carbon atom of the nitrogen which coordinates to the metal M, and the phenyl group is ortho-metalated by bonding to the metal M. Furthermore, among the substituents $R^2$, $R^3$, $R^4$, $R^5$, $R^6$, and $R^7$, any one of $R^1$, $R^5$, $R^6$, and $R^7$ is an alicyclic hydrocarbon having an intramolecular carbon-carbon bridged bond, and the others are separately any of hydrogen, halogen, a substituted or unsubstituted alkyl group having 1 to 4 carbon atoms, a substituted or unsubstituted alkoxy group having 1 to 4 carbon atoms, a substituted or unsubstituted alkylthio group having 1 to 4 carbon atoms, a substituted or unsubstituted haloalkyl group having 1 to 4 carbon atoms, and a substituted or unsubstituted aryl group having 6 to 10 carbon atoms. Note that the alicyclic hydrocarbon is preferably selected from a tricyclo[5.2.1.0(2,6)]decanyl group, a norbornyl group, and an adamantyl group.

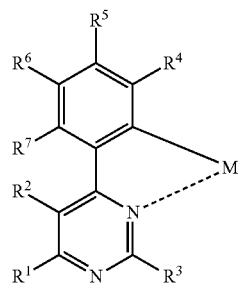

(G1)

The alicyclic hydrocarbon such as tricyclo[5.2.1.0(2,6)] decanyl group, the norbornyl group, and the adamantyl group, which is bonded to the ligand of the metal M, does not cause the prolongation of the emission wavelength owing to the resonance effect and donates an electron to the ligand owing to the inductive effect. A phosphorescent organometallic complex including a ligand to which an electron is donated has a high molecular absorption coefficient; thus, when it is dispersed in a host material, energy can be received from the host material efficiently. Alternatively, with the use of a phosphorescent organometallic complex including a ligand to which a bulky alicyclic hydrocarbon such as the tricyclo[5.2.1.0(2,6)]decanyl group, the norbornyl group, and the adamantyl group is bonded, concentration quenching is unlikely to occur because the increased intermolecular distance inhibits the aggregation.

In a phosphorescent organometallic complex having such a structure, the phenomenon of the emission-wavelength prolongation (also called red shift) is suppressed, and red, yellow, or green light can be emitted with high efficiency. With the use of such a phosphorescent organometallic complex, a light-emitting element with high emission efficiency can be provided.

Another embodiment of the invention is the above-described organic light-emitting element containing the phosphorescent organometallic complex which has a structure represented by the following general formula (G1). Further, among the substituents $R^2$, $R^3$, $R^4$, $R^5$, $R^6$, and $R^7$, $R^1$ is an alicyclic hydrocarbon having an intramolecular carbon-carbon bridged bond, and the others are separately any of hydrogen, halogen, a substituted or unsubstituted alkyl group having 1 to 4 carbon atoms, a substituted or unsubstituted alkoxy group having 1 to 4 carbon atoms, a substituted or unsubstituted alkylthio group having 1 to 4 carbon atoms, a substituted or unsubstituted haloalkyl group having 1 to 4 carbon atoms, and a substituted or unsubstituted aryl group having 6 to 10 carbon atoms. Note that the alicyclic hydrocarbon is preferably selected from a tricyclo[5.2.1.0(2,6)]decanyl group, a norbornyl group, and an adamantyl group.

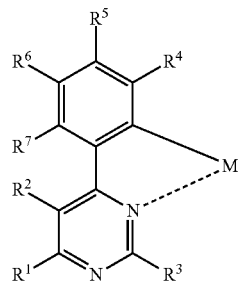

(G1)

The substituent $R^1$ of the pyrimidine ring coordinating to the metal M is an alicyclic hydrocarbon such as the tricyclo [5.2.1.0(2,6)]decanyl group, the norbornyl group, and the adamantyl group, so that an electron is donated to the ligand owing to the inductive effect, and the molecular absorption coefficient of the phosphorescent organometallic complex remarkably increases. With the use of such a phosphorescent organometallic complex, an organic light-emitting element with high emission efficiency can be provided:

Another embodiment of the invention is a phosphorescent organometallic complex which has a structure represented by the following general formula (G1). Further, the phosphorescent organometallic complex includes a metal M which is iridium or platinum and a pyrimidine ring coordinating to the metal M. A phenyl group is bonded to an α-carbon atom of the nitrogen which coordinates to the metal M, and the phenyl group is ortho-metalated by bonding to the metal M. Furthermore, among substituents $R^1$, $R^2$, $R^3$, $R^4$, $R^5$, $R^6$, and $R^7$, any one of $R^1$, $R^5$, $R^6$, and $R^7$ is an alicyclic hydrocarbon having an intramolecular carbon-carbon bridged bond, and the others are separately any of hydrogen, halogen, a substituted or unsubstituted alkyl group having 1 to 4 carbon atoms, a substituted or unsubstituted alkoxy group having 1 to 4 carbon atoms, a substituted or unsubstituted alkylthio group having 1 to 4 carbon atoms, a substituted or unsubstituted haloalkyl group having 1 to 4 carbon atoms, and a substituted or unsubstituted aryl group having 6 to 10 carbon atoms. Note that the alicyclic hydrocarbon is preferably selected from a tricyclo [5.2.1.0(2,6)]decanyl group, a norbornyl group, and an adamantyl group.

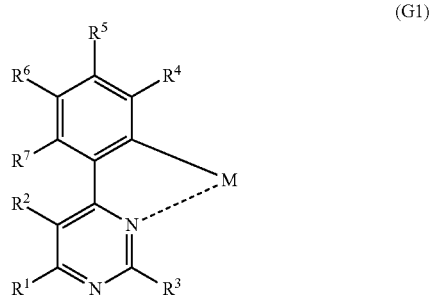

(G1)

The alicyclic hydrocarbon such as tricyclo[5.2.1.0(2,6)] decanyl group, the norbornyl group, and the adamantyl group, which is bonded to a ligand, does not cause the prolongation of the emission wavelength owing to the resonance effect and donates an electron to the ligand owing to the inductive effect. A phosphorescent organometallic complex including a ligand to which an electron is donated has a high molecular absorption coefficient; thus, when it is dispersed in a host material, the phosphorescent organometallic complex can receive energy from the host material efficiently.

Alternatively, with the use of a phosphorescent organometallic complex including a ligand to which a bulky alicyclic hydrocarbon such as tricyclo[5.2.1.0(2,6)]decanyl group, the norbornyl group, and the adamantyl group is bonded, concentration quenching is unlikely to occur because the increased intermolecular distance inhibits the aggregation.

Another embodiment of the invention is the above-described phosphorescent organometallic complex which has the structure represented by the following general formula (G1). Further, among the substituents $R^1$, $R^2$, $R^3$, $R^4$, $R^5$, $R^6$, and $R^7$, $R^1$ is an alicyclic hydrocarbon having an intramolecular carbon-carbon bridged bond, and the others are separately any of hydrogen, halogen, a substituted or unsubstituted alkyl group having 1 to 4 carbon atoms, a substituted or unsubstituted alkoxy group having 1 to 4 carbon atoms, a substituted or unsubstituted alkylthio group having 1 to 4 carbon atoms, a substituted or unsubstituted haloalkyl group having 1 to 4 carbon atoms, and a substituted or unsubstituted aryl group having 6 to 10 carbon atoms. Note that the alicyclic hydrocarbon is preferably selected from a tricyclo[5.2.1.0(2,6)] decanyl group, a norbornyl group, and an adamantyl group.

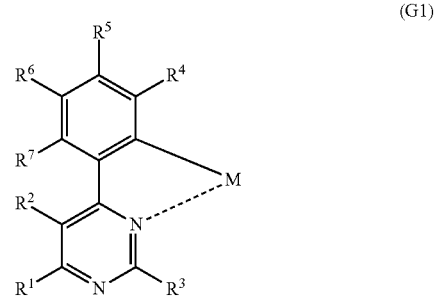

(G1)

The substituent $R^1$ of the pyrimidine ring coordinating to the metal M is an alicyclic hydrocarbon such as the tricyclo [5.2.1.0(2,6)]decanyl group, the norbornyl group, and the adamantyl group, so that an electron is donated to the ligand owing to the inductive effect, and the molecular absorption coefficient of the phosphorescent organometallic complex remarkably increases, which increases emission efficiency.

Another embodiment of the invention is a phosphorescent organometallic complex having the above-described structure in which the metal M is iridium.

Since the metal M is iridium, the spin-orbit interaction is increased. In addition, since the metal M and a ligand have metal-carbon bonding, charge is likely to be transferred to a pyrimidine ring which is the ligand (this transfer is also called triplet metal to ligand charge transfer (triplet MLCT)). As a result, a forbidden transition such as phosphorescence is likely to occur and the triplet excitation lifetime becomes shorter, which provides an effect of increasing the emission efficiency of the phosphorescent organometallic complex.

Another embodiment of the invention is a phosphorescent organometallic complex represented by the following general formula (G2). Further, the phosphorescent organometallic complex includes iridium, a pyrimidine ring coordinating to the iridium, and a monoanionic ligand L. Furthermore, a phenyl group is bonded to an α-carbon atom of a nitrogen atom which coordinates to the iridium, and the phenyl group is ortho-metalated by bonding to the iridium. Furthermore, among substituents $R^1$, $R^2$, $R^3$, $R^4$, $R^5$, $R^6$, and $R^7$, any one of $R^1$, $R^5$, $R^6$, and $R^7$ is an alicyclic hydrocarbon having an intramolecular carbon-carbon bridged bond, and the others are separately any of hydrogen, halogen, a substituted or unsubstituted alkyl group having 1 to 4 carbon atoms, a substituted or unsubstituted alkoxy group having 1 to 4 carbon atoms, a substituted or unsubstituted alkylthio group having 1 to 4 carbon atoms, a substituted or unsubstituted haloalkyl group having 1 to 4 carbon atoms, and a substituted or unsubstituted aryl group having 6 to 10 carbon atoms. Note that the alicyclic hydrocarbon is preferably selected from a tricyclo [5.2.1.0(2,6)]decanyl group, a norbornyl group, and an adamantyl group.

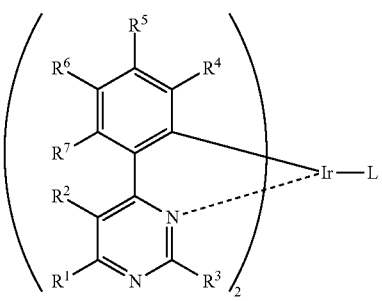

(G2)

Another embodiment of the invention is the phosphorescent organometallic complex represented by the following general formula (G2). Further, among the substituents $R^1$, $R^2$, $R^3$, $R^4$, $R^5$, $R^6$, and $R^7$, $R^1$ is an alicyclic hydrocarbon having an intramolecular carbon-carbon bridged bond, and the others are separately any of hydrogen, halogen, a substituted or unsubstituted alkyl group having 1 to 4 carbon atoms, a substituted or unsubstituted alkoxy group having 1 to 4 carbon atoms, a substituted or unsubstituted alkylthio group having 1 to 4 carbon atoms, a substituted or unsubstituted haloalkyl group having 1 to 4 carbon atoms, and a substituted or unsubstituted aryl group having 6 to 10 carbon atoms. Note that the alicyclic hydrocarbon is preferably selected from a tricyclo[5.2.1.0(2,6)]decanyl group, a norbornyl group, and an adamantyl group.

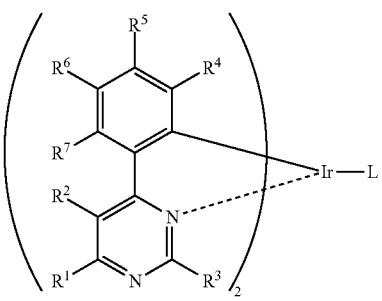

(G2)

The structure in which two pyrimidine rings and one monoanionic ligand L coordinate to iridium allows the increase in the phosphorescence quantum yield. This is because the symmetry of ligands coordinating to iridium is broken.

Another embodiment of the invention is the above-described phosphorescent organometallic complex in which the monoanionic ligand L is a β-diketone.

With the use of the β-diketone as the monoanionic ligand, the sublimation temperature can be lower; thus, an evaporation film can be easily formed. In addition, the material is unlikely to be decomposed by heat treatment in vacuum evaporation and thus is used efficiently. Alternatively, a decomposition product is unlikely to enter the evaporation film, so that characteristics of the evaporation film are hardly decreased and the reliability of the light-emitting element can be increased.

Another embodiment of the invention is a phosphorescent organometallic complex represented by the following general formula (G3). Further, the phosphorescent organometallic complex includes iridium and a pyrimidine ring coordinating to the iridium. Furthermore, a phenyl group is bonded to an et-carbon atom of a nitrogen atom which coordinates to the iridium, and the phenyl group is ortho-metalated by bonding to the iridium. Furthermore, among substituents $R^1$, $R^2$, $R^3$, $R^4$, $R^5$, $R^6$, and $R^7$, any one of $R^1$, $R^5$, $R^6$, and $R^7$ is an alicyclic hydrocarbon having an intramolecular carbon-carbon bridged bond, and the others are separately any of hydrogen, halogen, a substituted or unsubstituted alkyl group having 1 to 4 carbon atoms, a substituted or unsubstituted alkoxy group having 1 to 4 carbon atoms, a substituted or unsubstituted alkylthio group having 1 to 4 carbon atoms, a substituted or unsubstituted haloalkyl group having 1 to 4 carbon atoms, and a substituted or unsubstituted aryl group having 6 to 10 carbon atoms. Note that the alicyclic hydrocarbon is preferably selected from a tricyclo[5.2.1.0(2,6)]decanyl group, a norbornyl group, and an adamantyl group.

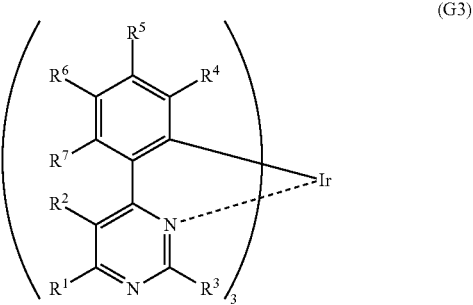

(G3)

The structure in which three pyrimidine rings coordinate to iridium has an effect of increasing the heat resistance. In addition, the material is unlikely to be decomposed by heat treatment in vacuum evaporation and thus is used efficiently. Alternatively, a decomposition product is unlikely to enter the evaporation film, so that characteristics of the evaporation film are hardly decreased and the reliability of the light-emitting element can be increased. In addition, the chemical stability can be one of factors in increasing the reliability.

Another embodiment of the invention is the above-described phosphorescent organometallic complex represented by the following general formula (G3). Further, among the substituents $R^1$, $R^2$, $R^3$, $R^4$, $R^5$, $R^6$, and $R^7$, $R^1$ is an alicyclic hydrocarbon having an intramolecular carbon-carbon bridged bond, and the others are separately any of hydrogen, halogen, a substituted or unsubstituted alkyl group having 1 to 4 carbon atoms, a substituted or unsubstituted alkoxy group having 1 to 4 carbon atoms, a substituted or unsubstituted alkylthio group having 1 to 4 carbon atoms, a substituted or unsubstituted haloalkyl group having 1 to 4 carbon atoms, and a substituted or unsubstituted aryl group having 6 to 10 carbon atoms. Note that the alicyclic hydrocarbon is preferably selected from a tricyclo[5.2.1.0(2,6)]decanyl group, a norbornyl group, and an adamantyl group.

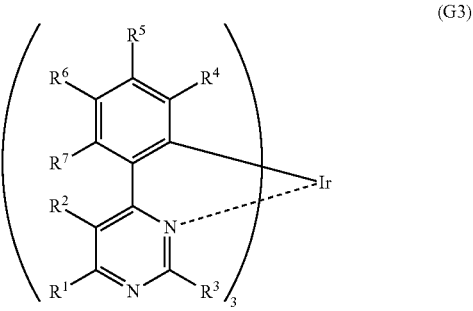

(G3)

The structure in which three pyrimidine rings coordinate to iridium has an effect of increasing the heat resistance. In addition, the material is unlikely to be decomposed by heat treatment in vacuum-evaporation and thus is used efficiently. Alternatively, a decomposition product is unlikely to enter the evaporation film, so that characteristics of the evaporation film are hardly decreased and the reliability of the light-emitting element can be increased. Further, the substituent $R^1$ of the pyrimidine ring coordinating to iridium is an alicyclic hydrocarbon having an intramolecular carbon-carbon bridged bond, which is selected from the tricyclo[5.2.1.0(2,6)]decanyl group, the norbornyl group, the adamantyl group, and the like, so that an electron is donated to the ligand owing to the inductive effect, and the molecular absorption coefficient of the phosphorescent organometallic complex remarkably increases, which increases emission efficiency.

Alternatively, when the phosphorescent organometallic complex is dispersed in a host material, energy can be received from the host material efficiently.

Another embodiment of the invention is a light-emitting device including the above-described light-emitting element.

Another embodiment of the invention is an electronic appliance including the above-described light-emitting device in a display portion.

Another embodiment of the invention is a lighting device including the above-described light-emitting device.

The phosphorescent organometallic complex has a 6-membered aromatic heterocycle, such as pyridine or monocyclic diazine, having a nitrogen atom, in which the nitrogen atom coordinates to iridium or platinum and an ortho-metalated aryl group is bonded to an α-carbon atom of the nitrogen atom. Further, the 6-membered aromatic heterocycle or the aryl group has an alicyclic hydrocarbon having an intramolecular carbon-carbon bridged bond, such as a tricyclo[5.2.1.0(2,6)]decanyl group, a norbornyl group, and an adamantyl group, as a substituent. When the phosphorescent organometallic complex is dispersed in a host material, energy can be received from the host material efficiently, and concentration quenching is unlikely to occur because the increased intermolecular distance inhibits the aggregation. By including a light-emitting element to which such a phosphorescent organometallic complex is applied, a light-emitting device, an electronic appliance, or a lighting device with high emission efficiency and low power consumption can be provided.

Note that in this specification, an "EL layer" refers to a layer provided between a pair of electrodes in a light-emitting element. Thus, a light-emitting layer containing an organic compound that is a light-emitting substance interposed between electrodes is an embodiment of the EL layer.

In this specification, in the case where a substance A is dispersed in a matrix formed using a substance B, the substance B forming the matrix is referred to as host material, and the substance A dispersed in the matrix is referred to as guest material. Note that the substance A and the substance B may each be a single substance or a mixture of two or more kinds of substances.

According to an embodiment of the invention, an organic light-emitting element with high emission efficiency can be provided. Alternatively, an organometallic complex with high emission efficiency can be provided. Alternatively, a light-emitting element with high emission efficiency can be provided. Alternatively, a light-emitting device with high emission efficiency and low power consumption can be provided. Alternatively, an electronic appliance with low power consumption can be provided. Alternatively, a lighting device with low power consumption can be provided.

BRIEF DESCRIPTION OF DRAWINGS

FIGS. 3A and 3B each illustrate an excited state of a host material which can be used for a light-emitting element according to an embodiment.

FIGS. 4A and 4B illustrate a light-emitting device according to an embodiment.

BEST MODE FOR CARRYING OUT THE INVENTION

Figure 1A:
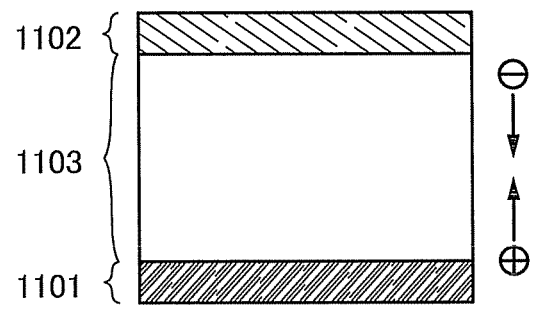
FIGS. 1A to 1C each illustrate a light-emitting element according to an embodiment.

Embodiments are described in detail with reference to the accompanying drawings. Note that the invention is not limited to the following description, and it will be easily understood by those skilled in the art that various changes and modifications can be made without departing from the spirit and scope of the invention. Therefore, the invention should not be construed as being limited to the description in the following embodiments.

Note that in the structures of the invention described below, the same portions or portions having similar functions are denoted by the same reference numerals in different drawings, and description of such portions is not repeated.

[Embodiment 1]

This embodiment shows, with reference to FIGS. 1A to 1C and FIGS. 2A and 2B, an example of a light-emitting element in which a phosphorescent organometallic complex according to an embodiment of the invention is applied to a layer which is provided between a pair of electrodes and which contains a light-emitting organic compound. In the phosphorescent organometallic complex, a 6-membered aromatic heterocycle such as pyridine and monocyclic diazine has a nitrogen atom coordinating to iridium or platinum, an ortho-metalated aryl group is bonded to an α-carbon atom of the nitrogen atom, and the 6-membered aromatic heterocycle or the aryl group has any one of a tricyclo[5.2.1.0(2,6)]decanyl group, a norbornyl group, and an adamantyl group, as a substituent. Specifically, this embodiment shows a structure in which the phosphorescent organometallic complex is dispersed in a host material and used for a light-emitting layer.

The light-emitting element exemplified in this embodiment includes a first electrode, a second electrode, and a layer containing a light-emitting organic compound (hereinafter referred to as EL layer) provided between the first electrode and the second electrode. Note that one of the first electrode and the second electrode functions as an anode, and the other functions as a cathode.

The EL layer is provided between the first electrode and the second electrode, and the structure of the EL layer may be appropriately selected in accordance with materials of the first electrode and second electrode. An example of the structure of the light-emitting element is described below; it is needless to say that the structure of the light-emitting element is not limited to this example.

[Structure Example 1 of the Light-Emitting Element]

An example of the structure of the light-emitting element is illustrated in FIG. 1A. In the light-emitting element illustrated in FIG. 1A, an EL layer 1103 is provided between an anode 1101 and a cathode 1102.

When a voltage higher than the threshold voltage of the light-emitting element is applied between the anode 1101 and the cathode 1102, holes are injected to the EL layer 1103 from the anode 1101 side and electrons are injected to the EL layer 1103 from the cathode 1102 side. The injected electrons and holes are recombined in the EL layer 1103 and the light-emitting substance contained in the EL layer 1103 emits light.

The EL layer 1103 may include at least a light-emitting layer containing a light-emitting substance, and may have a structure in which a layer other than the light-emitting layer and the light-emitting layer are stacked. Examples of the layer other than the light-emitting layer are layers containing a substance having a high hole-injection property, a substance having a high hole-transport property, a substance having a poor hole-transport property (substance which blocks holes), a substance having a high electron-transport property, a substance having a high electron-injection property, and a substance having a bipolar property (substance having high electron- and hole-transport properties).

Figure 1B:
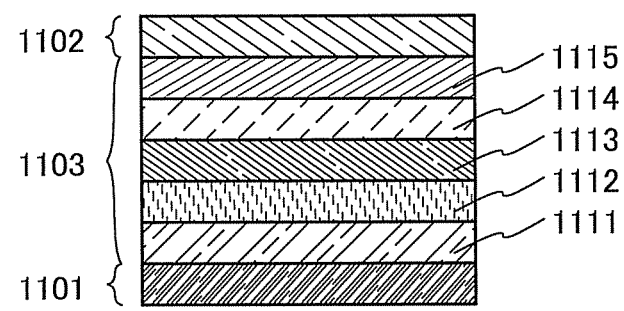

An example of a specific structure of the EL layer 1103 is illustrated in FIG. 1B. The EL layer 1103 illustrated in FIG. 1B has a structure in which a hole-injection layer 1111, a hole-transport layer 1112, a light-emitting layer 1113, an electron-transport layer 1114, and an electron-injection layer 1115 are stacked in that order from the anode 1101 side.

[Structure Example 2 of the Light-Emitting Element]

Figure 1C:
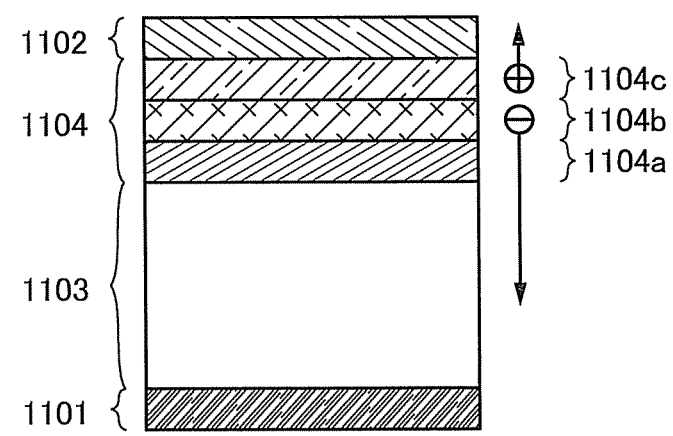

Another example of the structure of the light-emitting element is illustrated in FIG. 1C. In the light-emitting element exemplified in FIG. 1C, the EL layer 1103 is provided between the anode 1101 and the cathode 1102. Further, an intermediate layer 1104 is provided between the cathode 1102 and the EL layer 1103. Note that a structure similar to that in the above structure example 1 of the light-emitting element can be applied to the EL layer 1103 in the structure example 2 of the light-emitting element, and for the details, the description of the structure example 1 of the light-emitting element can be referred to.

The intermediate layer 1104 may be formed to include at least a charge production region, and may have a structure in which the charge production region and a layer other than the charge production region are stacked. For example, a structure can be employed in which a first charge production region 1104c, an electron-relay layer 1104b, and an electron-injection buffer 1104a are stacked in that order from the cathode 1102 side.

The behaviors of electrons and holes in the intermediate layer 1104 are described. When a voltage higher than the threshold voltage of the light-emitting element is applied between the anode 1101 and the cathode 1102, in the first charge production region 1104c, holes and electrons are produced, and the holes move into the cathode 1102 and the electrons move into the electron-relay layer 1104b. The electron-relay layer 1104b has a high electron-transport property and immediately transfers the electrons produced in the first charge production region 1104c to the electron-injection buffer 1104a. The electron-injection buffer 1104a can reduce a barrier in injection of electrons into the EL layer 1103, and the efficiency of the electron injection into the EL layer 1103 can be increased. Thus, the electrons produced in the first charge production region 1104c are injected into the LUMO level of the EL layer 1103 through the electron-relay layer 1104b and the electron-injection buffer 1104a.

In addition, the electron-relay layer 1104b can prevent the damage to the first charge production region 1104c and the electron-injection buffer 1104a caused by the reaction of the substance contained in the first charge production region 1104c with the substance contained in the electron-injection buffer 1104a at the interface thereof.

A material for the cathode in the structure example 2 of the light-emitting element can be selected from a wider range than the material for the cathode of the structure example 1. This is because the cathode of the structure example 2 can be formed using a material having a relatively high work function as long as the cathode receives holes produced in the intermediate layer.

[Structure Example 3 of the Light-Emitting Element]

Figure 2A:
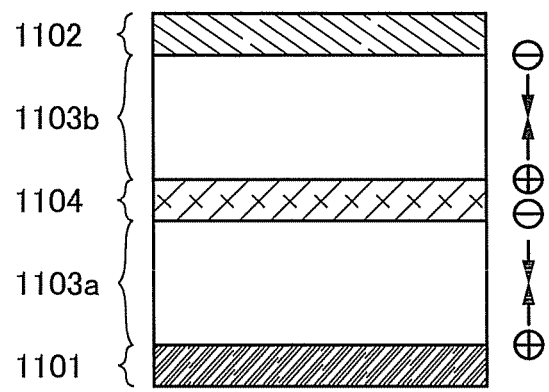
FIGS. 2A and 2B each illustrate a light-emitting element according to an embodiment.
Figure 2B:
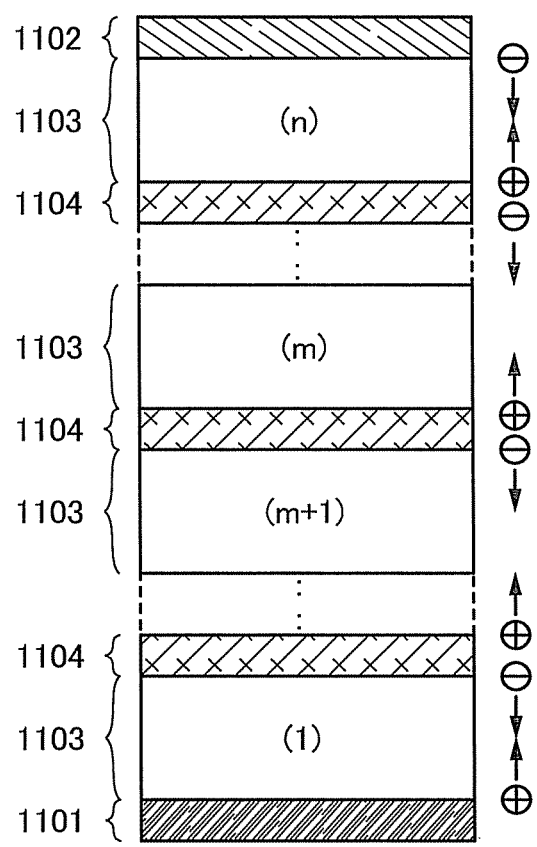

Another example of the structure of the light-emitting element is illustrated in FIG. 2A. In the light-emitting element exemplified in FIG. 2A, two EL layers are provided between the anode 1101 and the cathode 1102. Further, the intermediate layer 1104 is provided between an EL layer 1103a and an EL layer 1103b.

Note that the number of the EL layers provided between the anode and the cathode is not limited to two. A light-emitting element exemplified in FIG. 2B has a structure in which a plurality of EL layers 1103 are stacked, that is, a tandem-type light-emitting element structure. Note that in the case where n (n is a natural number of 2 or more) EL layers 1103 are provided between the anode 1101 and the cathode 1102, the intermediate layer 1104 is provided between an m-th (m is a natural number greater than or equal to 1 and less than or equal to n−1) EL layer and an (m+1)-th EL layer.

Note that a structure similar to that in the above structure example 1 of the light-emitting element can be applied to the EL layers 1103 in the structure example 3 of the light-emitting element; a structure similar to that in the above structure example 2 of the light-emitting element can be applied to the intermediate layer 1104 in the structure example 3 of the light-emitting element. Thus, for the details, the description of the structure example 1 of the light-emitting element or the structure example 2 of the light-emitting element can be referred to.

The behaviors of electrons and holes in the intermediate layer 1104 provided between the EL layers are described. When a voltage higher than the threshold voltage of the light-emitting element is applied between the anode 1101 and the cathode 1102, in the intermediate layer 1104, holes and electrons are produced, and the holes move into the EL layer which is provided on the cathode 1102 side and the electrons move into the EL layer which is provided on the anode 1101 side. The holes injected into the EL layer which is provided on the cathode side are recombined with the electrons injected from the cathode side, so that the light-emitting substance contained in the EL layer emits light. The electrons injected into the EL layer which is provided on the anode side are recombined with the holes injected from the anode side, so that the light-emitting substance contained in the EL layer emits light. Thus, the holes and electrons produced in the intermediate layer 1104 cause light emission in the respective EL layers.

Note that in the case where a structure which is the same as an intermediate layer is formed between the EL layers by contacting the EL layers with each other, the EL layers can be formed to be in contact with each other. Specifically, when a charge production region is formed on one surface of the EL layer, the charge production region functions as a first charge production region of an intermediate layer; thus, the EL layers can be formed to be in contact with each other.

The structure examples 1 to 3 of the light-emitting element can be implemented in combination. For example, an intermediate layer may be provided between the cathode and the n-th EL layer in the structure example 3 of the light-emitting element.

[Material for the Light-Emitting Element]

Next, specific materials that can be used for the light-emitting element having the above-described structure are described. Materials for the anode, the cathode, the EL layer, the first charge production region, the electron-relay layer, and the electron-injection buffer are described in that order.

[Material for the Anode]

The anode 1101 is preferably formed using a metal, an alloy, an electrically conductive compound, a mixture thereof, or the like which has a high work function (specifically, a work function of 4.0 eV or higher is more preferable). Specifically, for example, indium tin oxide (ITO), indium tin oxide containing silicon or silicon oxide, indium zinc oxide (TZO), indium oxide containing tungsten oxide and zinc oxide, and the like are given.

Such conductive metal oxide films are usually formed by a sputtering method, but may also be formed by application of a sol-gel method or the like. For example, an indium-zinc oxide film can be formed by a sputtering method using a target in which zinc oxide is added to indium oxide at greater than or equal to 1 wt % and less than or equal to 20 wt %. A film of indium oxide containing tungsten oxide and zinc oxide can be formed by a sputtering method using a target in which tungsten oxide and zinc oxide are added to indium oxide at greater than or equal to 0.5 wt % and less than or equal to 5 wt % and greater than or equal to 0.1 wt % and less than or equal to 1 wt %, respectively.

Besides, as a material used for the anode 1101, the following can be given: gold (Au), platinum (Pt), nickel (Ni), tungsten (W), chromium (Cr), molybdenum (Mo), iron (Fe), cobalt (Co), copper (Cu), palladium (Pd), titanium (Ti), nitride of a metal material (e.g., titanium nitride), and the like.

Note that in the case where a second charge production region is provided in contact with the anode 1101, a variety of conductive materials can be used for the anode 1101 regardless of their work functions. Specifically, besides a material which has a high work function, a material which has a low work function can also be used for the anode 1101. A material for forming the second charge production region is subsequently described together with a material for forming the first charge production region.

[Material for the Cathode]

In the case where the first charge production region 1104c is provided between the cathode 1102 and the EL layer 1103 to be in contact with the cathode 1102, a variety of conductive materials can be used for the cathode 1102 regardless of their work functions.

Note that at least one of the cathode 1102 and the anode 1101 is formed using a conductive film that transmits visible light. For the conductive film that transmits visible light, for example, indium oxide containing tungsten oxide, indium zinc oxide containing tungsten oxide, indium oxide containing titanium oxide, indium tin oxide containing titanium oxide, indium tin oxide (also referred to as ITO), indium zinc oxide, indium tin oxide to which silicon oxide is added, or the like can be used. Further, a thin metal film having a thickness enough to transmit light (preferably, approximately 5 nm to 30 nm) can also be used. In this case, the thin metal film serves as a semi-transmissive and semi-reflective electrode.

[Material for the EL Layer]

Specific examples of materials for the layers included in the above EL layer 1103 are described below.

The hole-injection layer contains a substance having a high hole-injection property. As the substance having a high hole-injection property, for example, molybdenum oxide, vanadium oxide, ruthenium oxide, tungsten oxide, manganese oxide, or the like can be used. In addition, it is possible to use a phthalocyanine-based compound such as phthalocyanine (abbreviation: $H_2Pc$) or copper phthalocyanine (abbreviation: CuPc), a polymer such as poly(3,4-ethylenedioxythiophene)/poly(styrenesulfonic acid) (PEDOT/PSS), or the like to form the hole-injection layer.

Note that the second charge production region may be formed instead of the hole-injection layer. When the second charge production region is used, a variety of conductive materials can be used for the anode 1101 regardless of their work functions as described above. A material for forming the second charge production region is subsequently described together with a material for forming the first charge production region.

The hole-transport layer contains a substance having a high hole-transport property. The hole-transport layer is not limited to a single layer, but may be a stack of two or more layers each containing a substance having a high hole-transport property. The hole-transport layer contains any substance having a higher hole-transport property than an electron-transport property; and preferably contains a substance having a hole mobility of $10^{-6}$ cm$^2$/V·s or higher because the driving voltage of the light-emitting element can be reduced.

Examples of the substance having a high hole-transport property include aromatic amine compounds such as 4,4'-bis[N-(1-naphthyl)-N-phenylamino]biphenyl (abbreviation:

NPB or α-NPD), N,N'-bis(3-methylphenyl)-N,N'-diphenyl-[1,1'-biphenyl]-4,4'-diamine (abbreviation: TPD), 4-phenyl-4'-(9-phenylfluoren-9-yl)triphenylamine (abbreviation: BPAFLP), 4,4',4''-tris(carbazol-9-yl)triphenylamine (abbreviation: TCTA), 4,4',4''-tris(N,N-diphenylamino)triphenylamine (abbreviation: TDATA), 4,4',4''-tris[N-(3-methylphenyl)-N-phenylamino]triphenylamine (abbreviation: MTDATA), and 4,4'-bis[N-(spiro-9,9'-bifluorene-2-yl)-N-phenylamino]biphenyl (abbreviation: BSPB). Examples further include 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), and the like. Examples further include carbazole derivatives such as 4,4'-di(N-carbazolyl)biphenyl (abbreviation: CBP), 1,3,5-tris[4-(N-carbazolyl)phenyl]benzene (abbreviation: TCPB), and 9-[4-(10-phenyl-9-anthracenyl)phenyl]-9H-carbazole (abbreviation: CzPA).

Besides the above substances, the hole-transport layer can be formed using a high molecular compound such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl)methacrylamide] (abbreviation: PTPDMA), or poly[N,N'-bis(4-butylphenyl)-N,N'-bis(phenyl)benzidine] (abbreviation: Poly-TPD).

The light-emitting layer contains the phosphorescent organometallic complex according to the embodiments of the invention as a light-emitting substance. The light-emitting layer is not limited to a single layer, but may be a stack of two or more layers containing light-emitting substances. As the light-emitting substance, a fluorescent compound may be used together with the phosphorescent organometallic complex.

The light-emitting element exemplified in this embodiment contains the phosphorescent organometallic complex in a light-emitting layer. In the phosphorescent organometallic complex, a 6-membered aromatic heterocycle such as pyridine and monocyclic diazine has a nitrogen atom coordinating to iridium or platinum, an ortho-metalated aryl group is bonded to an α-carbon atom of the nitrogen atom, and the 6-membered aromatic heterocycle or the aryl group has any one of a tricyclo[5.2.1.0(2,6)]decanyl group, a norbornyl group, and an adamantyl group, as a substituent.

A phosphorescent organometallic iridium complex which can be used for a light-emitting element according to an embodiment of the invention is described in detail in Embodiment 2. An example of the phosphorescent organometallic iridium complex is (acetylacetonato)bis[4-(2-norbornyl)-6-phenylpyrimidinato]iridium(III) (endo- and exo-mixture) (abbreviation: Ir(nbppm)$_2$(acac)) or the like.

Examples of a fluorescent compound that can be used together with the phosphorescent organometallic complex of an embodiment of the present invention include N,N'-bis[4-(9H-carbazol-9-yl)phenyl]-N,N'-diphenylstilbene-4,4'-diamine (abbreviation: YGA2S), 4-(9H-carbazol-9-yl)-4'-(10-phenyl-9-anthryl)triphenylamine (abbreviation: YGAPA), 4-(9H-carbazol-9-yl)-4'-(9,10-diphenyl-2-anthryl)triphenylamine (abbreviation: 2YGAPPA), N,9-diphenyl-N-[4-(10-phenyl-9-anthryl)phenyl]-9H-carbazol-3-amine (abbreviation: PCAPA), perylene, 2,5,8,11-tetra-tert-butylperylene (abbreviation: TBP), 4-(10-phenyl-9-anthryl)-4'-(9-phenyl-9H-carbazol-3-yl)triphenylamine (abbreviation: PCBAPA), N,N''-(2-tert-butylanthracene-9,10-diyldi-4,1-phenylene)bis[N,N',N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), N,N,N',N',N'',N'',N''',N'''-Nm-octaphenyldibenzo[g,p]chrysene-2,7,10,15-tetraamine (abbreviation: DBC1), coumarin 30, N-(9,10-diphenyl-2-anthryl)-N,9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N'-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA), coumarin 545T, N,N'-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinitrile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), 2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), 2-{2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), 2-{2,6-bis[2-(8-methoxy-1,1,7,7-tetramethyl-2,3,6,7-tetrahydro-1H,5H-benzo[ij]quinolizin-9-yl]ethenyl}-4H-pyran-4-ylidene}propanedinitrile (abbreviation: BisDCJTM), SD1 (product name; manufactured by SFC Co., Ltd), and the like.

Examples of a phosphorescent compound that can be used together with the phosphorescent organometallic complex of an embodiment of the present invention include bis[2-(4',6'-difluorophenyl)pyridinato-N,C$^{2'}$]iridium(III)tetrakis(1-pyrazolyl)borate (abbreviation: FIr6), bis[2-(4',6'-difluorophenyl)pyridinato-N,C$^{2'}$]iridium(III) picolinate (abbreviation: FIrpic), bis[2-(3',5'-bistrifluoromethylphenyl)pyridinato-N,C$^{2'}$]iridium(III) picolinate (abbreviation: Ir(CF$_3$ppy)$_2$(pic)), bis[2-(4',6'-difluorophenyl)pyridinato-N,C$^{2'}$]iridium(III) acetylacetonate (abbreviation: FIracac), tris(2-phenylpyridinato)iridium(III) (abbreviation: Ir(ppy)$_3$), bis(2-phenylpyridinato)iridium(III) acetylacetonate (abbreviation: Ir(ppy)$_2$(acac)), bis(benzo[h]quinolinato)iridium(III) acetylacetonate (abbreviation: Ir(bzq)$_2$(acac)), bis(2,4-diphenyl-1,3-oxazolato-N,C$^{2'}$)iridium(III) acetylacetonate (abbreviation: Ir(dpo)$_2$(acac)), bis{2-[4'-(perfluorophenyl)phenyl]pyridinato-N,C$^{2'}$}iridium(III) acetylacetonate (abbreviation: Ir(p-PF-ph)$_2$(acac)), bis(2-phenylbenzothiazolato-N,C$^{2'}$)iridium(III) acetylacetonate (abbreviation: Ir(bt)$_2$(acac)), bis[2-(2'-benzo[4,5-a]thienyl)pyridinato-N,C$^{3'}$]iridium(III) acetylacetonate (abbreviation: Ir(btp)$_2$(acac)), bis(1-phenylisoquinolinato-N,C$^{2'}$)iridium(III) acetylacetonate (abbreviation: Ir(piq)$_2$(acac)), (acetylacetonato)bis[2,3-bis(4-fluorophenyl)quinoxalinato]iridium(III) (abbreviation: Ir(Fdpq)$_2$(acac)), (acetylacetonato)bis(2,3,5-triphenylpyrazinato)iridium(III) (abbreviation: Ir(tppr)$_2$(acac)), (2,3,7,8,12,13,17,18-octaethyl-21H,23H-porphine)platinum(II) (abbreviation: PtOEP), tris(acetylacetonato)(monophenanthroline)terbium(III) (abbreviation: Tb(acac)$_3$ (Phen)), tris(1,3-diphenyl-1,3-propanedionato)(monophenanthroline)europium(III) (abbreviation: Eu(DBM)$_3$(Phen)), tris[1-(2-thenoyl)-3,3,3-trifluoroacetonato](monophenanthroline)europium(III) (abbreviation: Eu(TTA)$_3$(Phen)), bis(2,3,5-triphenylpyrazinato)(dipivaloylmethanato)iridium(III) (abbreviation: Ir(tppr)$_2$(dpm)), and the like.

The light-emitting substance is preferably dispersed in a host material. As the host material, it is possible to use an aromatic amine compound such as NPB, TPD, TCTA, TDATA, MTDATA, or BSPB; or a carbazole derivative such as PCzPCA1, PCzPCA2, PCzPCN1, CBP, TCPB, CzPA, 9-phenyl-3-[4-(10-phenyl-9-anthryl)phenyl]-9H-carbazole (abbreviation: PCzPA), or 4-phenyl-4'-(9-phenyl-9H-carbazol-3-yl)triphenylamine (abbreviation: PCBA1BP). Alternatively, it is possible to use a substance which has a high hole-transport property and includes a high molecular compound, such as PVK, PVTPA, PTPDMA, or Poly-TPD. Alternatively, it is possible to use a metal complex having a quinoline skeleton or a benzoquinoline skeleton, such as tris(8-quinolinolato)aluminum (abbreviation: Alq), tris(4-methyl-8-quinolinolato)aluminum (abbreviation: Almq$_3$), bis(10-hydroxybenzo [h]quinolinato)beryllium (abbreviation: BeBq$_2$), or bis(2-methyl-8-quinolinolato)(4-phenylphenolato)aluminum (abbreviation: BAlq). Alternatively, it is possible to use a metal complex having an oxazole-based or thiazole-based ligand, such as bis[2-(2'-hydroxyphenyl)benzoxazolato]zinc (abbreviation: Zn(BOX)$_2$) or bis[2-(2'-hydroxyphenyl)benzothiazolato]zinc (abbreviation: Zn(BTZ)$_2$). Further alternatively, it is possible to use a substance having a high electron-transport property, such as 2-(4-biphenylyl)-5-(4-tert-butylphenyl)-1,3,4-oxadiazole (abbreviation: PBD), 1,3-bis[5-(p-tert-butylphenyl)-1,3,4-oxadiazol-2-yl]benzene (abbreviation: OXD-7), 9-[4-(5-phenyl-1,3,4-oxadiazol-2-yl)phenyl]carbazole (abbreviation: CO11), 3-(4-biphenylyl)-4-phenyl-5-(4-tert-butylphenyl)-1,2,4-triazole (abbreviation: TAZ), bathophenanthroline (abbreviation: BPhen), or bathocuproine (abbreviation: BCP).

The electron-transport layer contains a substance having a high electron-transport property. The electron-transport layer is not limited to a single layer, but may be a stack of two or more layers each containing a substance having a high electron-transport property. The electron-transport layer contains any substance having a higher electron-transport property than a hole-transport property, and preferably contains a substance having an electron mobility of $10^{-6}$/V·s or higher because the driving voltage of the light-emitting element can be reduced.

As the substance having a high electron-transport property, for example, a metal complex having a quinoline skeleton or a benzoquinoline skeleton, such as Alq, Almq$_3$, BeBq$_2$, or BAlq, or the like can be used. Alternatively, a metal complex having an oxazole-based or thiazole-based ligand, such as Zn(BOX)$_2$ or Zn(BTZ)$_2$, or the like can be used. Further alternatively, PBD, OXD-7, CO11, TAZ, BPhen, BCP, 2-[4-(dibenzothiophen-4-yl)phenyl]-1-phenyl-1H-benzimidazole (abbreviation: DBTBIm-II), or the like can be used.

Besides the above-described materials, the electron-transport layer can be formed using a polymer such as poly[(9,9-dihexylfluorene-2,7-diyl)-co-(pyridine-3,5-diyl)] (abbreviation: PF-Py) or poly[(9,9-dioctylfluorene-2,7-diyl)-co-(2,2'-bipyridine-6,6'-diyl)] (abbreviation: PF-BPy).

The electron-injection layer contains a substance having a high electron-injection property. The electron-injection layer is not limited to a single layer, but may be a stack of two or more layers containing substances having a high electron-injection property. The electron-injection layer is preferably provided because the efficiency of electron injection from the cathode 1102 can be increased and the driving voltage of the light-emitting element can be reduced.

As the substance having a high electron-injection property, the following can be given: an alkali metal and an alkaline earth metal such as lithium (Li), cesium (Cs), calcium (Ca) and a compound thereof, such as lithium fluoride (LiF), cesium fluoride (CsF), and calcium fluoride (CaF$_2$). Alternatively, a layer containing a substance having an electron-transport property and an alkali metal, an alkaline earth metal, magnesium (Mg), or a compound thereof (e.g., an Alq layer containing magnesium (Mg)) can be used.

As a method for forming the EL layer 1103 by combining these layers as appropriate, any of a variety of methods (e.g., a dry process and a wet process) can be selected as appropriate. For example, a vacuum evaporation method, an inkjet method, a spin coating method, or the like may be selected in accordance with a material to be used. Note that a different formation method may be employed for each layer.

[Material for the Charge Production Region]

The first charge production region 1104c and the second charge production region contain a substance having a high hole-transport property and an acceptor substance. These charge production regions may contain a substance having a high hole-transport property and an acceptor substance in the same film or may be a stack of a layer containing a substance having a high hole-transport property and a layer containing an acceptor substance. Note that in the case where the first charge production region which is in contact with the cathode has a stacked-layer structure, the layer containing the substance having a high hole-transport property is in contact with the cathode 1102. In the case where the second charge production region which is in contact with the anode has a stacked-layer structure, the layer containing the acceptor substance is in contact with the anode 1101.

Note that the acceptor substance is preferably added to the charge production region so that the mass ratio of the acceptor substance to the substance having a high hole-transport property is from 0.1:1 to 4.0:1.

As the acceptor substance that is used for the charge production region, a transition metal oxide, particularly an oxide of a metal belonging to Group 4 to 8 of the periodic table is preferred. Specifically, molybdenum oxide is particularly preferable. Note that molybdenum oxide has a low hygroscopic property.

As the high hole-transport substance used for the charge production region, any of a variety of organic compounds such as an aromatic amine compound, a carbazole derivative, an aromatic hydrocarbon, and a polymer (including an oligomer and a dendrimer) can be used. Specifically, a substance having a hole mobility of $10^{-6}$ cm$^2$/V·s or higher is preferably used.

[Material for the Electron-Relay Layer]

The electron-relay layer 1104b can smoothly accept electrons abstracted by the acceptor substance in the first charge production region 1104c. Therefore, the electron-relay layer 1104b contains a substance having a high electron-transport property, and the LUMO level thereof is positioned between the acceptor level of the acceptor substance in the first charge production region 1104c and the LUMO level of the EL layer 1103. Specifically, the LUMO level of the electron-relay layer 1104b is preferably about from −5.0 eV to −3.0 eV.

As the substance used for the electron-relay layer 1104b, for example, a perylene derivative and a nitrogen-containing condensed aromatic compound can be given. Note that a nitrogen-containing condensed aromatic compound is preferably used for the electron-relay layer 1104b because of its stability. Among nitrogen-containing condensed aromatic compounds, a compound having an electron-withdrawing group such as a cyano group or fluorine is preferably used because such a compound further facilitates acceptance of electrons in the electron-relay layer 1104b.

As specific examples of the perylene derivative, the following can be given: 3,4,9,10-perylenetetracarboxylic dianhydride (abbreviation: PTCDA), 3,4,9,10-perylenetetracarboxylic bisbenzimidazole (abbreviation: PTCBI), N,N'-dioctyl-3,4,9,10-perylenetetracarboxylic diimide (abbreviation: PTCDI-C8H), N,N'-dihexyl-3,4,9,10-perylenetetracarboxylic diimide (abbreviation: Hex PTC), and the like.

As specific examples of the nitrogen-containing condensed aromatic compound, the following can be given: pirazino[2,3-f][1,10]phenanthroline-2,3-dicarbonitrile (abbreviation: PPDN), 2,3,6,7,10,11-hexacyano-1,4,5,8,9,12-hexaazatriphenylene (abbreviation: HAT(CN)$_6$), 2,3-diphenylpyrido[2,3-b]pyrazine (abbreviation: 2PYPR), 2,3-bis(4-fluorophenyl)pyrido[2,3-b]pyrazine (abbreviation: F2PYPR), and the like.

Besides, 7,7,8,8-tetracyanoquinodimethane (abbreviation: TCNQ), 1,4,5,8-naphthalenetetracarboxylic dianhydride (abbreviation: NTCDA), perfluoropentacene, copper hexadecafluorophthalocyanine (abbreviation: F$_{16}$CuPc), N,N'-bis(2,2,3,3,4,4,5,5,6,6,7,7,8,8-pentadecafluorooctyl)-1,4,5,8-naphthalenetetracarboxylic diimide (abbreviation: NTCDI-C8F), 3',4'-dibutyl-5,5'''-bis(dicyanomethylene)-5,5'''-dihydro-2,2':5',2''-terthiophen (abbreviation: DCMT), methanofullerenes (e.g., [6,6]-phenyl C$_{61}$ butyric acid methyl ester), or the like can be used for the electron-relay layer 1104b.

[Material for the Electron-Injection Buffer]

The electron-injection buffer 1104a facilitates electron injection from the first charge production region 1104c into the EL layer 1103. The provision of the electron-injection buffer 1104a between the first charge production region 1104c and the EL layer 1103 makes it possible to reduce the injection barrier therebetween.

A substance having a high electron-injection property can be used for the electron-injection buffer 1104a. For example, an alkali metal, an alkaline earth metal, a rare earth metal, a compound thereof (e.g., an alkali metal compound (including an oxide such as lithium oxide, a halide, and a carbonate such as lithium carbonate or cesium carbonate), an alkaline earth metal compound (including an oxide, a halide, and a carbonate), or a rare earth metal compound (including an oxide, a halide, and a carbonate)) can be used.

Further, in the case where the electron-injection buffer 1104a contains a substance having a high electron-transport property and a donor substance, the donor substance is preferably added so that the mass ratio of the donor substance to the substance having a high electron-transport property is greater than or equal to 0.001:1 and less than or equal to 0.1:1. Note that as the donor substance, an organic compound such as tetrathianaphthacene (abbreviation: TTN), nickelocene, or decamethylnickelocene can be used besides an alkali metal, an alkaline earth metal, a rare earth metal, a compound thereof (e.g., an alkali metal compound (including an oxide of lithium oxide or the like, a halide, and a carbonate such as lithium carbonate or cesium carbonate), an alkaline earth metal compound (including an oxide, a halide, and a carbonate), and a rare earth metal compound (including an oxide, a halide, and a carbonate). Note that as the substance having a high electron-transport property, a material similar to the above-described material for the electron-transport layer that can be formed in part of the EL layer 1103 can be used.

The light-emitting element described in this embodiment can be fabricated by combination of the above-described materials. Light emission from the phosphorescent organometallic iridium complex according to an embodiment of the invention can be obtained with this light-emitting element, and the emission color can be selected by changing the phosphorescent organometallic iridium complex. Further, a plurality of light-emitting substances which emit light of different colors can be used, whereby, for example, white light emission can also be obtained by expanding the width of the emission spectrum. Note that in order to obtain white light emission, light-emitting substances whose emission colors are complementary to each other may be used. For example, different layers whose emission colors are complementary to each other are used. Specific examples of complementary colors include "blue and yellow", "blue-green and red", and the like.

In an organic light-emitting element according to an embodiment of the invention, a phosphorescent organometallic complex according to an embodiment of the invention is applied to the light-emitting layer. In the phosphorescent organometallic complex, a 6-membered aromatic heterocycle such as pyridine and monocyclic diazine has a nitrogen atom coordinating to iridium or platinum, an ortho-metalated aryl group is bonded to an α-carbon atom of the nitrogen atom, and the 6-membered aromatic heterocycle or the aryl group has any one of a tricyclo[5.2.1.0(2,6)]decanyl group, a norbornyl group, and an adamantyl group as a substituent.

The tricyclo[5.2.1.0(2,6)]decanyl group, the norbornyl group, or the adamantyl group, which is bonded to a ligand of iridium or platinum, does not cause the prolongation of the emission wavelength owing to the resonance effect and donates an electron to the ligand owing to the inductive effect. A phosphorescent organometallic complex including a ligand to which an electron is donated has a high molecular absorption coefficient; thus, when it is dispersed in a host material, energy can be received from the host material efficiently. Alternatively, with the use of a phosphorescent organometallic complex including a bulky substituent such as tricyclo[5.2.1.0(2,6)]decanyl group, the norbornyl group, and the adamantyl group, concentration quenching is unlikely to occur because the increased intermolecular distance inhibits the aggregation.

With the use of such a phosphorescent organometallic complex, an organic light-emitting element with high emission efficiency can be provided.

This embodiment can be combined with any of the other embodiments in this specification as appropriate.

(Embodiment 2)

This embodiment shows examples of the phosphorescent organometallic complex according to an embodiment of the invention.

The phosphorescent organometallic complex according to an embodiment of the invention includes a metal and a 6-membered aromatic heterocycle having a nitrogen atom coordinating to the metal. The metal is iridium or platinum. Further, the 6-membered aromatic heterocycle is pyridine or monocyclic diazine, an aryl group is bonded to an α-carbon atom of the nitrogen atom, and the aryl group is ortho-metalated by bonding to the metal. Furthermore, the 6-membered aromatic heterocycle or the aryl group has any one of a tricyclo[5.2.1.0(2,6)]decanyl group, a norbornyl group, and an adamantyl group as a substituent.

The 6-membered aromatic heterocycle included in the phosphorescent organometallic complex according to an embodiment of the invention has a pyridine skeleton or a monocyclic diazine skeleton. Specifically, the monocyclic diazine skeleton is a 1,2-diazine (also called pyridazine) skeleton, a 1,3-diazine or 1,5-diazine (also called pyrimidine) skeleton, or a 1,4-diazine (also called pyrazine) skeleton. A nitrogen atom of the pyridine skeleton and one of nitrogen atoms in the monocyclic diazine skeleton coordinate to iridium or platinum, and an aryl group is bonded to an α-carbon atom of the nitrogen (i.e., a carbon atom which is directly bonded to the nitrogen atom). The aryl group is ortho-metalated by bonding to the iridium or platinum.

Examples of the aryl group included in the phosphorescent organometallic complex according to an embodiment of the invention include a phenyl group, a phenyl group substituted by one or more alkyl groups each having 1 to 4 carbon atoms, a phenyl group substituted by one or more alkoxy groups each having 1 to 4 carbon atoms, a phenyl group substituted by one or more alkylthio groups each having 1 to 4 carbon atoms, a phenyl group substituted by one or more aryl groups each having 6 to 10 carbon atoms, a phenyl group substituted by one or more halogens, a phenyl group substituted by one or more haloalkyl groups each having 1 to 4 carbon atoms, a substituted or unsubstituted biphenyl group, and a substituted or unsubstituted naphthyl group.

The 6-membered aromatic heterocycle or the aryl group in the phosphorescent organometallic complex according to an embodiment of the invention has a bridged alicyclic substituent as a substituent. Examples of the bridged alicyclic substituent include a tricyclo[5.2.1.0(2,6)]decanyl group, a norbornyl group, and an adamantyl group. There are an endo-isomer and an exo-isomer of a norbornane compound, and either may be applied to the invention, or both may be used in combination.

The tricyclo[5.2.1.0(2,6)]decanyl group, the norbornyl group, or the adamantyl group, which is bonded to the 6-membered aromatic heterocycle or the aryl group included in the phosphorescent organometallic complex according to an embodiment of the invention, does not cause the prolongation of the emission wavelength of the phosphorescent organometallic complex owing to the resonance effect and donates an electron to the ligand owing to the inductive effect. A phosphorescent organometallic complex including a ligand to which an electron is donated has a high molecular absorption coefficient; thus, when it is dispersed in a host material, energy can be received from the host material efficiently. Alternatively, since the tricyclo[5.2.1.0(2,6)]decanyl group, the norbornyl group, and the adamantyl group each has a bulky structure, with the use of a phosphorescent organometallic complex including a ligand to which any of the substituents is bonded, concentration quenching is unlikely to occur because the increased intermolecular distance inhibits the aggregation.

[Structure Example 1 of the Phosphorescent Organometallic Complex]

An embodiment of the invention is a phosphorescent organometallic complex which has a structure represented by the following general formula (G1). The phosphorescent organometallic complex includes a metal M which is iridium or platinum and a pyrimidine ring coordinating to the metal M. A phenyl group is bonded to an α-carbon atom of a nitrogen atom which coordinates to the metal M, and the phenyl group is ortho-metalated by bonding to the metal M. Among substituents $R^1$, $R^2$, $R^3$, $R^4$, $R^5$, $R^6$, and $R^7$, any one of $R^1$, $R^5$, $R^6$, and $R^7$ is selected from a tricyclo[5.2.1.0(2,6)]decanyl group, a norbornyl group, and an adamantyl group, and the others are separately any of hydrogen, halogen, a substituted or unsubstituted alkyl group having 1 to 4 carbon atoms, a substituted or unsubstituted alkoxy group having 1 to 4 carbon atoms, a substituted or unsubstituted alkylthio group having 1 to 4 carbon atoms, a substituted or unsubstituted haloalkyl group having 1 to 4 carbon atoms, and a substituted or unsubstituted aryl group having 6 to 10 carbon atoms.

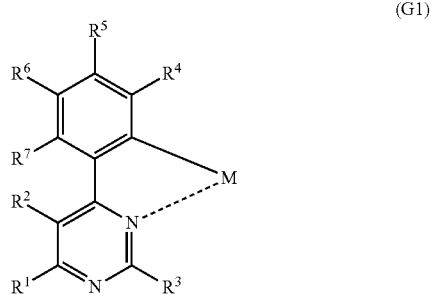

(G1)

As the halogen, for example, fluorine can be given.

As the substituted or unsubstituted alkyl group having 1 to 4 carbon atoms, for example, a methyl group, an ethyl group, a propyl group, an isopropyl group, a n-butyl group, a sec-butyl group, an isobutyl group, a tert-butyl group and the like can be given.

As the substituted or unsubstituted alkoxy group having 1 to 4 carbon atoms, for example, a methoxy group, an ethoxy group, a propoxy group, an isopropoxy group, a n-butoxy group, a sec-butoxy group, an isobutoxy group, a tert-butoxy group, and the like can be given.

As the substituted or unsubstituted alkylthio group having 1 to 4 carbon atoms, for example, a methylsulfanyl group (methylthio group), an ethylsulfanyl group (ethylthio group), a propylsulfanyl group (propylthio group), an isopropylsulfanyl group (isopropylthio group), a n-butylsulfanyl group (n-butylthio group), an isobutylsulfanyl group (isobutylthio group), a sec-butylsulfanyl group (sec-butylthio group), a tert-butylsulfanyl group (tert-butylthio group), and the like can be given.

As the substituted or unsubstituted haloalkyl group having 1 to 4 carbon atoms, for example, a fluoromethyl group, a difluoromethyl group, a trifluoromethyl group, a chloromethyl group, a dichloromethyl group, a trichloromethyl group, a bromomethyl group, a 2,2,2-trifluoroethyl group, a 3,3,3-trifluoropropyl group, and a 1,1,1,3,3,3-hexafluoroisopropyl group, and the like can be given.

As the substituted or unsubstituted aryl group having 6 to 10 carbon atoms, a phenyl group, a phenyl group substituted by one or more alkyl groups each having 1 to 4 carbon atoms, a phenyl group substituted by one or more alkoxy groups each having 1 to 4 carbon atoms, a phenyl group substituted by one or more alkylthio groups each having 1 to 4 carbon atoms, a phenyl group substituted by one or more aryl groups each having 6 to 10 carbon atoms, a phenyl group substituted by one or more halogens, a phenyl group substituted by one or more haloalkyl groups each having 1 to 4 carbon atoms, a substituted or unsubstituted naphthalene-yl group, and the like can be given.

The alkyl group having 1 to 4 carbon atoms in $R^1$ is preferably an alkyl group having 2 or more carbon atoms. An alkyl group having 2 or more carbon atoms suppresses intermolecular interaction due to steric hindrance. Therefore, side reaction in synthesis reaction of an organometallic complex according to an embodiment of the invention is suppressed and the yield is increased. Considering this tendency, the alkyl group having 1 to 4 carbon atoms in $R^1$ is more preferably an ethyl group, a propyl group, an isopropyl group, a n-butyl group, a sec-butyl group, an isobutyl group, or a tert-butyl group.

The alkyl group having 1 to 4 carbon atoms in $R^2$ is preferably a methyl group. By providing a methyl group in $R^2$, it is possible to shift the emission wavelength of the phosphorescent organometallic complex according to an embodiment of the invention to a short wavelength side (this shift is also referred to as blue shift).

[Structure Example 2 of the Phosphorescent Organometallic Complex]

Another embodiment of the invention is a phosphorescent organometallic complex in the structure example 1 of the phosphorescent organometallic complex which has the structure represented by the following general formula (G1). Further, among the substituents $R^1, R^2, R^3, R^4, R^5, R^6$ and $R^7$, $R^1$ is one selected from a tricyclo[5.2.1.0(2,6)]decanyl group, a norbornyl group, and an adamantyl group, and the others are separately any of hydrogen, halogen, a substituted or unsubstituted alkyl group having 1 to 4 carbon atoms, a substituted or unsubstituted alkoxy group having 1 to 4 carbon atoms, a substituted or unsubstituted alkylthio group having 1 to 4 carbon atoms, a substituted or unsubstituted haloalkyl group having 1 to 4 carbon atoms, and a substituted or unsubstituted aryl group having 6 to 10 carbon atoms.

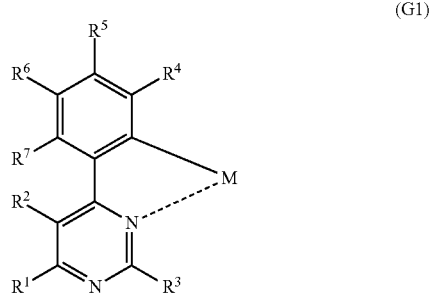

(G1)

Specific examples of the halogen, the substituted or unsubstituted alkyl group having 1 to 4 carbon atoms, the substituted or unsubstituted alkoxy group having 1 to 4 carbon atoms, the substituted or unsubstituted alkylthio group having 1 to 4 carbon atoms, the substituted or unsubstituted haloalkyl group having 1 to 4 carbon atoms, and the substituted or unsubstituted aryl group having 6 to 10 carbon atoms are the same as those in the structure example 1 of the phosphorescent organometallic complex.

The substituent $R^1$ of the pyrimidine ring coordinating to iridium or platinum is one selected from a tricyclo[5.2.1.0(2,6)]decanyl group, a norbornyl group, and an adamantyl group, so that an electron is donated to the ligand owing to the inductive effect, and the molecular absorption coefficient of the phosphorescent organometallic complex remarkably increases, which increases emission efficiency.

[Structure Example 3 of the Phosphorescent Organometallic Complex]

Another embodiment of the invention is a phosphorescent organometallic complex in the structure example 1 or 2 of the phosphorescent organometallic complex in which the metal M is iridium.

Since the metal M is iridium, the spin-orbit interaction is increased. In addition, since the metal M and a ligand have metal-carbon bonding, charge is likely to be transferred from iridium to a pyrimidine ring (this transfer is also called triplet metal to ligand charge transfer (triplet MLCT)). As a result, a forbidden transition such as phosphorescence is likely to occur and the triplet excitation lifetime decreases, giving an effect of increasing the emission efficiency of the phosphorescent organometallic complex.

[Structure Example 4 of the Phosphorescent Organometallic Complex]

Another embodiment of the invention is a phosphorescent organometallic complex represented by the following general formula (G2). The phosphorescent organometallic complex includes iridium, a pyrimidine ring coordinating to the iridium, and a monoanionic ligand L. A phenyl group is bonded to an α-carbon atom of a nitrogen atom coordinating to the iridium, and the phenyl group is ortho-metalated by bonding to the iridium. Among substituents $R^1, R^2, R^3, R^4, R^5, R^6$, and $R^7$, any one of $R^1, R^5, R^6$, and $R^7$ is selected from a tricyclo[5.2.1.0(2,6)]decanyl group, a norbornyl group, and an adamantyl group, and the others are separately any of hydrogen, halogen, a substituted or unsubstituted alkyl group having 1 to 4 carbon atoms, a substituted or unsubstituted alkoxy group having 1 to 4 carbon atoms, a substituted or unsubstituted alkylthio group having 1 to 4 carbon atoms, a substituted or unsubstituted haloalkyl group having 1 to 4 carbon atoms, and a substituted or unsubstituted aryl group having 6 to 10 carbon atoms.

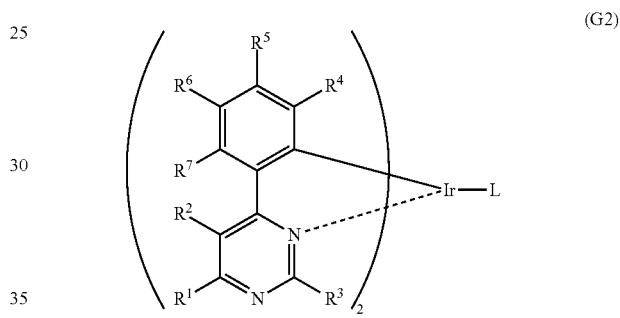

(G2)

[Structure Example 5 of the Phosphorescent Organometallic Complex]

Another embodiment of the invention is the phosphorescent organometallic complex represented by the following general formula (G2). Among the substituents $R^1, R^2, R^3, R^4, R^5, R^6$, and $R^7$, $R^1$ is one selected from a tricyclo[5.2.1.0(2,6)]decanyl group, a norbornyl group, and an adamantyl group, and the others are separately any of hydrogen, halogen, a substituted or unsubstituted alkyl group having 1 to 4 carbon atoms, a substituted or unsubstituted alkoxy group having 1 to 4 carbon atoms, a substituted or unsubstituted alkylthio group having 1 to 4 carbon atoms, a substituted or unsubstituted haloalkyl group having 1 to 4 carbon atoms, and a substituted or unsubstituted aryl group having 6 to 10 carbon atoms.

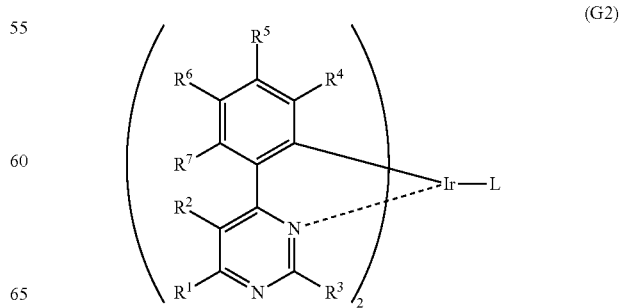

(G2)

With the phosphorescent organometallic complexes in the structure examples 4 and 5, in which two pyrimidine rings and one monoanionic ligand L coordinate to iridium, the phosphorescence quantum yield is increased. This is because the symmetry of ligands coordinating to iridium is broken.

[Structure Example 6 of the Phosphorescent Organometallic Complex]

Another embodiment of the invention is a phosphorescent organometallic complex in the structure example 4 or 5 of the phosphorescent organometallic complex in which the monoanionic ligand is a β-diketone.

With the use of the β-diketone as the monoanionic ligand, the sublimation temperature can be lower; thus, an evaporation film can be easily formed. In addition, the material is unlikely to be decomposed by heat treatment in vacuum evaporation and thus is used efficiently. Alternatively, a decomposition product is unlikely to enter the evaporation film, so that characteristics of the evaporation film are hardly decreased and the reliability of the light-emitting element can be increased.

[Structure Example 7 of the Phosphorescent Organometallic Complex]

Another embodiment of the invention is a phosphorescent organometallic complex represented by the following general formula (G3). The phosphorescent organometallic complex includes iridium and a pyrimidine ring coordinating to the iridium. Furthermore, a phenyl group is bonded to an α-carbon atom of a nitrogen atom coordinating to the iridium, and the phenyl group is ortho-metalated by bonding to the iridium. Furthermore, among substituents $R^1$, $R^2$, $R^3$, $R^4$, $R^5$, $R^6$, and $R^7$, any one of $R^1$, $R^5$, $R^6$, and $R^7$ is selected from a tricyclo[5.2.1.0(2,6)]decanyl group, a norbornyl group, and an adamantyl group, and the others are separately any of hydrogen, halogen, a substituted or unsubstituted alkyl group having 1 to 4 carbon atoms, a substituted or unsubstituted alkoxy group having 1 to 4 carbon atoms, a substituted or unsubstituted alkylthio group having 1 to 4 carbon atoms, a substituted or unsubstituted haloalkyl group having 1 to 4 carbon atoms, and a substituted or unsubstituted aryl group having 6 to 10 carbon atoms.

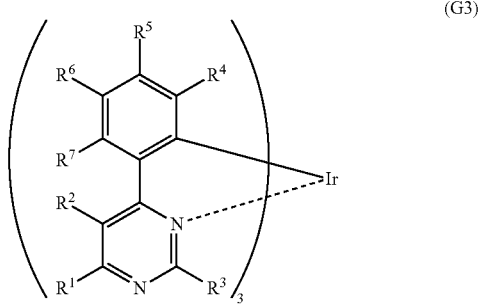

(G3)

The structure in which three pyrimidine rings coordinate to iridium has an effect of increasing the heat resistance. In addition, the material is unlikely to be decomposed by heat treatment in vacuum evaporation and thus is used efficiently. Alternatively, a decomposition product is unlikely to enter the evaporation film, so that characteristics of the evaporation film are hardly decreased and the reliability of the light-emitting element can be increased. In addition, the chemical stability can be one of factors in increasing the reliability.

[Structure Example 8 of the Phosphorescent Organometallic Complex]

Another embodiment of the invention is a phosphorescent organometallic complex represented by the following general formula (G3). Among the substituents $R^1$, $R^2$, $R^3$, $R^4$, $R^5$, $R^6$, and $R^7$, $R^1$ is one selected from a tricyclo[5.2.1.0(2,6)]decanyl group, a norbornyl group, and an adamantyl group, and the others are separately any of hydrogen, halogen, a substituted or unsubstituted alkyl group having 1 to 4 carbon atoms, a substituted or unsubstituted alkoxy group having 1 to 4 carbon atoms, a substituted or unsubstituted alkylthio group having 1 to 4 carbon atoms, a substituted or unsubstituted haloalkyl group having 1 to 4 carbon atoms, and a substituted or unsubstituted aryl group having 6 to 10 carbon atoms.

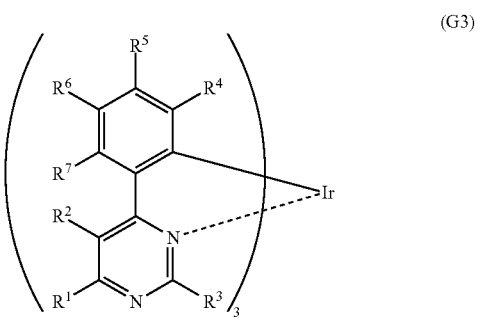

(G3)

The structure in which three pyrimidine rings coordinate to iridium has an effect of increasing the heat resistance. In addition, the material is unlikely to be decomposed by heat treatment in vacuum evaporation and thus is used efficiently. Alternatively, a decomposition product is unlikely to enter the evaporation film, so that characteristics of the evaporation film are hardly decreased and the reliability of the light-emitting element can be increased. Further, the substituent $R^1$ of the pyrimidine ring coordinating to iridium is one selected from the tricyclo[5.2.1.0(2,6)]decanyl group, the norbornyl group, and the adamantyl group, so that an electron is donated to the ligand owing to the inductive effect, and the molecular absorption coefficient of the phosphorescent organometallic complex remarkably increases, which increases emission efficiency.

Alternatively, when the phosphorescent organometallic complex is dispersed in a host material, energy can be received from the host material efficiently.

The following shows an example of a method of synthesizing a phosphorescent organometallic complex according to an embodiment of the invention.

[Method of Synthesizing a 4-Arylpyrimidine Derivative Represented by a General Formula (G0)]

An example of a method of synthesizing a 4-arylpyrimidine derivative represented by the following general formula (G0) is described. The 4-arylpyrimidine derivative represented by the general formula (G0) can be synthesized by any of synthesis schemes (a), (a'), and (a''), which are simple as illustrated below.

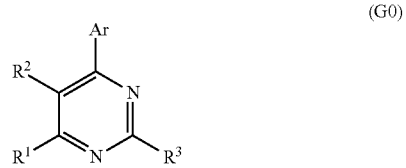

(G0)

In the general formula (G0), $R^1$ to $R^3$ separately represent hydrogen, a substituted or unsubstituted alkyl group having 1 to 4 carbon atoms, a substituted or unsubstituted alkoxy group having 1 to 4 carbon atoms, a substituted or unsubstituted alkylthio group having 1 to 4 carbon atoms, a substituted or unsubstituted haloalkyl group having 1 to 4 carbon atoms, or a substituted or unsubstituted aryl group having 6 to 10 carbon atoms, and Ar represents a substituted or unsubstituted aryl group having 6 to 10 carbon atoms, provided that at least one of $R^1$ and the substituent of the aryl group is an alicyclic hydrocarbon having an intramolecularly bridged carbon-carbon bond. Note that a substituent other than hydrogen is particularly preferable for $R^1$.

For example, as illustrated in the synthesis scheme (a), an arylboronic acid (A1) is coupled with a halogenated pyrimidine compound (A2), whereby the 4-arylpyrimidine derivative represented by the general formula (G0) is obtained.

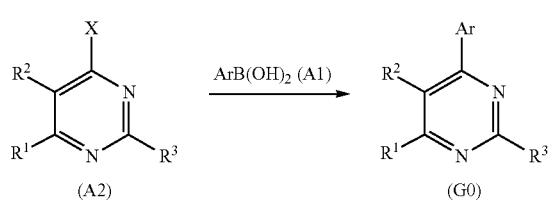

(a)

In the synthesis scheme (a), X represents halogen.

Alternatively, as illustrated in the synthesis scheme (a'), an aryllithium compound or a Grignard reagent illustrated in (A1') is reacted with a pyrimidine compound (A2'), whereby the 4-arylpyrimidine derivative represented by the general formula (G0) is obtained.

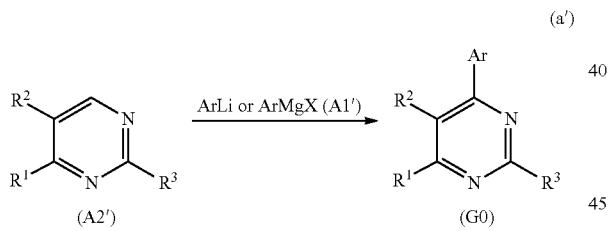

(a')

In the synthesis scheme (a'), X represents halogen.

Further alternatively, as illustrated in the synthesis scheme (a''), a 1,3-diketone (A1'') with an aryl substituent is reacted with an amidine (A2''), whereby the 4-arylpyrimidine derivative represented by the general formula (G0) is obtained.

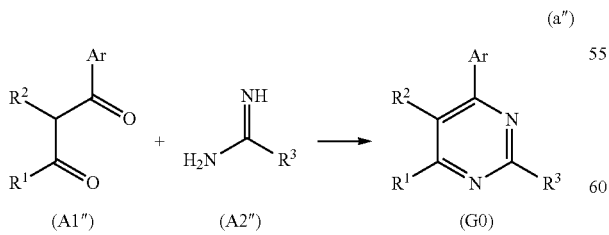

(a'')

Note that in the case where $R^3$ is hydrogen in the general formula (G0), as shown in Non-Patent Document (H. Bredereck, R. Gompper, G Morlock, "Chemische Berichte," 90, pp. 942-952 (1957)), the 1,3-diketone (A1'') with an aryl substituent is reacted with formamide under heating in the presence of an acid catalyst, whereby the 4-arylpyrimidine derivative represented by the general formula (G0) is obtained.

In the synthesis scheme (a''), $R^1$ represents a substituted or unsubstituted alkyl group having 1 to 4 carbon atoms or a substituted or unsubstituted aryl group having 6 to 10 carbon atoms, $R^2$ represents any of hydrogen, halogen, a substituted or unsubstituted alkyl group having 1 to 4 carbon atoms, a substituted or unsubstituted alkoxy group having 1 to 4 carbon atoms, a substituted or unsubstituted alkylthio group having 1 to 4 carbon atoms, a substituted or unsubstituted haloalkyl group having 1 to 4 carbon atoms, and a substituted or unsubstituted phenyl group, $R^3$ represents hydrogen or a substituted or unsubstituted alkyl group having 1 to 4 carbon atoms, and Ar represents a substituted or unsubstituted aryl group having 6 to 10 carbon atoms, provided that at least one of $R^1$ and the substituent of the aryl group is an alicyclic hydrocarbon having an intramolecularly bridged carbon-carbon bond.

Since a wide variety of compounds (A1), (A2), (A1'), (A2'), (A1''), and (A2'') are commercially available or their synthesis is feasible, a great variety of the 4-arylpyrimidine derivative represented by the general formula (G0) can be synthesized. Thus, a feature of the organometallic complex according to an embodiment of the invention is the abundance of ligand variations.

[Method of Synthesizing Organometallic Complexes According to Embodiments of the Invention, Represented by General Formulas (G2) and (G3)]

The following shows examples of a method of synthesizing an organometallic complex represented by the following general formulas (G2) and (G3) by ortho-metalating a 4-arylpyrimidine derivative represented by the general formula (G0). Specifically, as a preferable example, the following shows methods of synthesizing organometallic complexes by using a general formula (G0') in which the aryl group in the general formula (G0) is a phenyl group and $R^2$ is hydrogen.

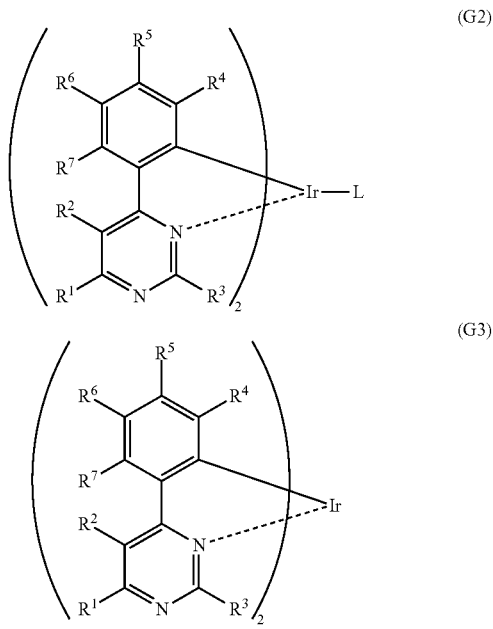

In each of the general formulas (G2) and (G3), L represents a monoanionic ligand. In addition, $R^1$ and $R^3$ to $R^7$ separately represent hydrogen, halogen, a substituted or unsubstituted alkyl group having 1 to 4 carbon atoms, a substituted or unsubstituted alkoxy group having 1 to 4 carbon atoms, a substituted or unsubstituted alkylthio group having 1 to 4 carbon atoms, a substituted or unsubstituted haloalkyl group having 1 to 4 carbon atoms, or a substituted or unsubstituted aryl group having 6 to 10 carbon atoms, provided that at least one of $R^1$ and $R^3$ to $R^7$ is an alicyclic hydrocarbon having an intramolecularly bridged carbon-carbon bond.

[Method of Synthesizing an Organometallic Complex According to an Embodiment of the Invention, Represented by the General Formula (G2)]

First, as illustrated in a synthesis scheme (b) below, a 4-phenylpyrimidine derivative represented by a general formula (G0') and an iridium halide (e.g., iridium chloride, iridium bromide, or iridium iodide, preferably iridium trichloride hydrate) are heated in an inert gas atmosphere in bulk, in an alcoholic solvent (e.g., glycerol, ethylene glycol, 2-metoxyethanol, or 2-ethoxyethanol) alone, or in a mixed solvent of water and one or more of the alcoholic solvents, whereby a dinuclear complex (B), which is a novel type of an organometallic complex including a halogen-bridged structure, can be obtained. Microwaves can be used as a heating means.

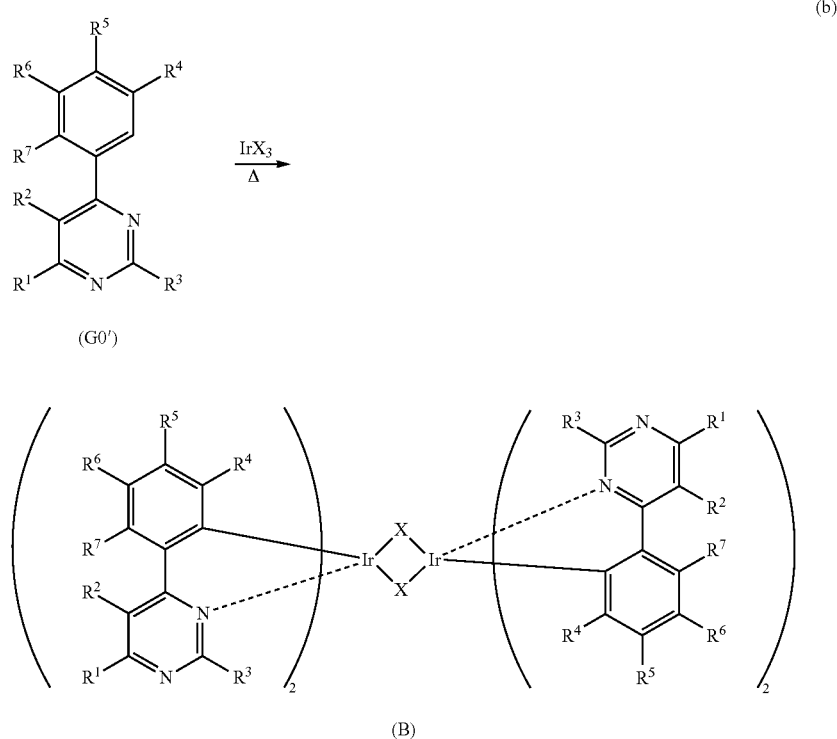

(b)

In the synthesis scheme (b), X represents halogen.

Further, as illustrated in a synthesis scheme (c) below, the dinuclear complex (B) obtained in the above synthesis scheme (b) is reacted with a ligand HL in an inert gas atmosphere, whereby a proton of HL is eliminated and L coordinates to the central metal Ir. Thus, the organometallic complex according to an embodiment of the invention, represented by the general formula (G2), can be obtained. Microwaves can be used as a heating means.

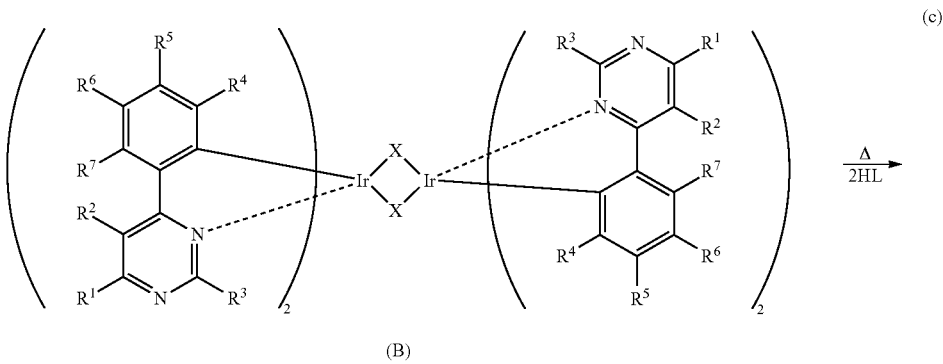

(c)

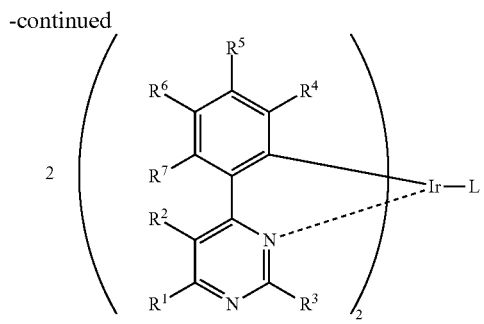

(G2)

In the synthesis scheme (c), L represents a monoanionic ligand.

Note that, compared to the case where hydrogen is used in $R^1$, the use of a substituted or unsubstituted alkyl group having 1 to 4 carbon atoms or a substituted or unsubstituted aryl group having 6 to 10 carbon atoms as $R^1$ prevents the decomposition of the dinuclear metal complex in the synthesis scheme (c), which contributes to a drastic increase in the yield.

Note that the monoanionic ligand L in the general formula (G2) is preferably any of a monoanionic bidentate chelate ligand having a β-diketone structure, a monoanionic bidentate chelate ligand having a carboxyl group, a monoanionic bidentate chelate ligand having a phenolic hydroxyl group, and a monoanionic bidentate chelate ligand in which two ligand elements are both nitrogen. A monoanionic bidentate chelate ligand having a β-diketone structure is particularly preferable because the solubility of an organometallic complex in an organic solvent is increased and the purification is easy. Further, a β-diketone structure is preferably included to obtain an organometallic complex with high emission efficiency. Inclusion of a β-diketone structure has advantages such as a higher sublimation property and excellent evaporativity.

The monoanionic ligand is preferably a ligand represented by any of general formulas (L1) to (L7). Since these ligands have high coordinative ability and can be obtained at low price, they are useful.

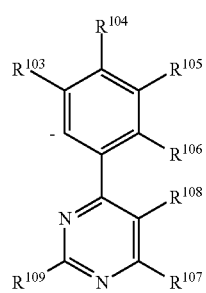

(L7)

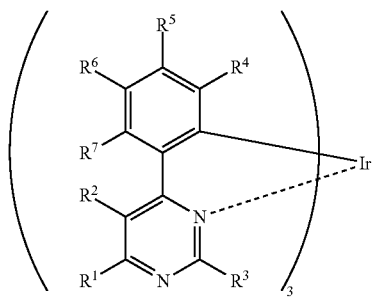

(G3)

In the general formulas (L1) to (L7), $R^{71}$ to $R^{109}$ separately represent any of hydrogen, a substituted or unsubstituted alkyl group having 1 to 4 carbon atoms, halogen, a vinyl group, a substituted or unsubstituted haloalkyl group having 1 to 4 carbon atoms, a substituted or unsubstituted alkoxy group having 1 to 4 carbon atoms, and a substituted or unsubstituted alkylthio group having 1 to 4 carbon atoms. In addition, $A^1$ to $A^3$ separately represent any of nitrogen, $sp^2$ carbon bonded to hydrogen, and $sp^2$ carbon bonded to a substituent R. The substituent R represents any of an alkyl group having 1 to 4 carbon atoms, halogen, a haloalkyl group having 1 to 4 carbon atoms, and a phenyl group.

[Method of Synthesizing an Organometallic Complex According to an Embodiment of the Invention, Represented by the General Formula (G3)]

The organometallic complex according to an embodiment of the invention, represented by the general formula (G3), can be synthesized by a synthesis scheme (d) below. That is, a 4-phenylpyrimidine derivative represented by the general formula (G0') is mixed with a iridium halide (e.g., iridium chloride, iridium bromide, or iridium iodide, preferably iridium trichloride hydrate) or an iridium complex (e.g., an acetylacetonate complex or a diethylsulfide complex) and then they are heated, whereby the organometallic complex having a structure represented by the general formula (G3) can be obtained. This reaction may be performed in the presence of a solvent such as an alcohol-based solvent (e.g., glycerol, ethylene glycol, 2-metoxyethanol, or 2-ethoxyethanol). Microwaves can be used as a heating means.

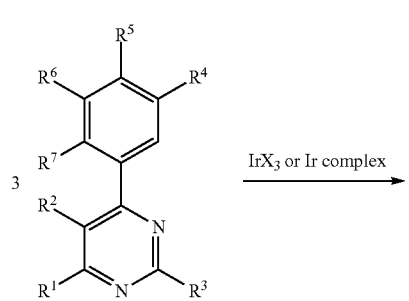

(d)

In the synthesis scheme (d), $R^1$ to $R^7$ are similarly defined as those of the aforementioned general formula (G3).

Note that, compared to the case where hydrogen is used in $R^1$, the use of a substituted or unsubstituted alkyl group having 1 to 4 carbon atoms or a substituted or unsubstituted aryl group having 6 to 10 carbon atoms as $R^1$ prevents the dinuclear metal complex from being decomposed, which leads to increase in the yield in the synthesis scheme (d).

Although examples of the synthesis methods are described above, organometallic complexes according to embodiments of the disclosed invention may be synthesized by any other synthesis method.

Specific structural formulas of an organometallic complex according to an embodiment of the invention are illustrated in structural formulas (100) to (141). Note that the invention is not limited to these examples.

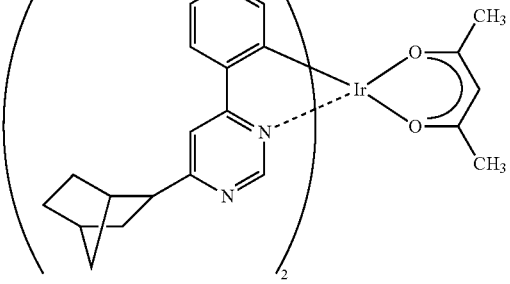

(100)

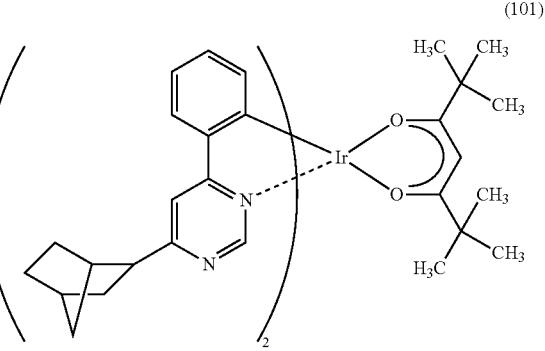

(101)

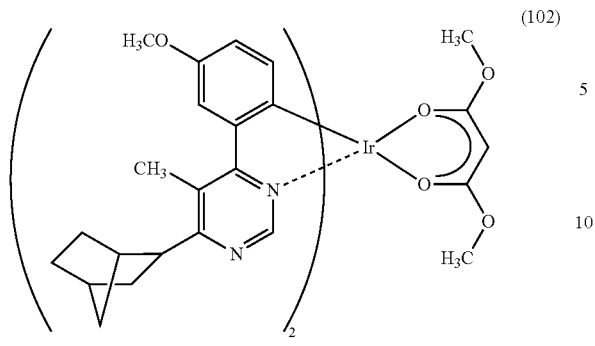
(102)
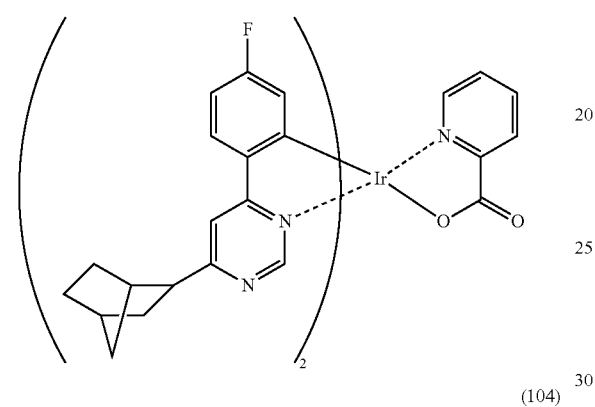
(103)
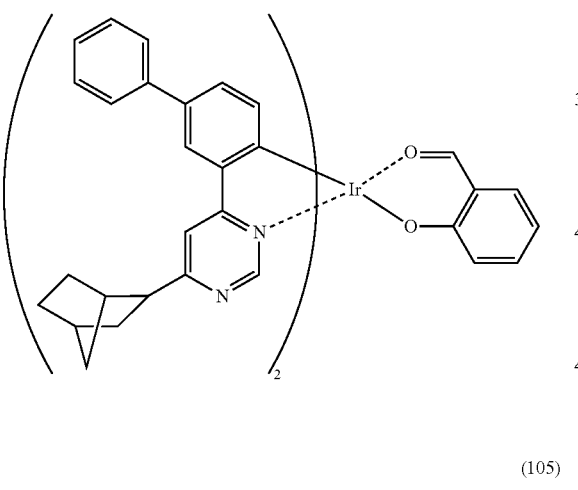
(104)
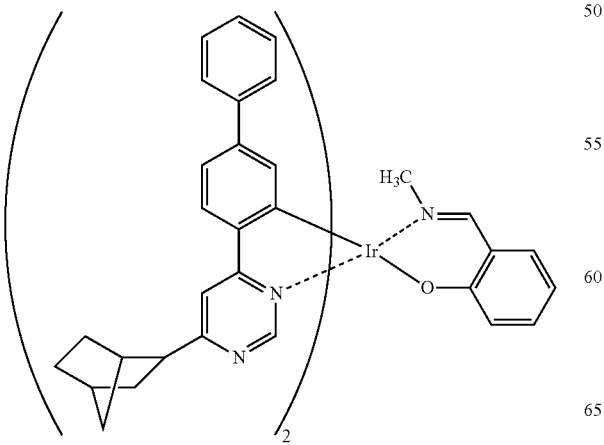
(105)
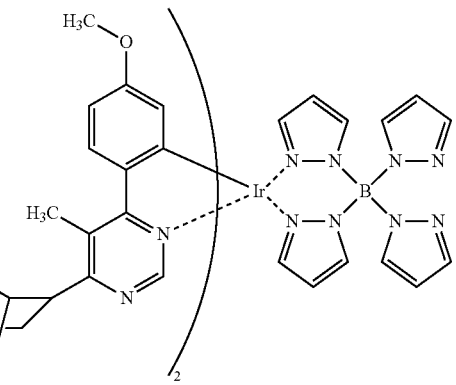
(106)
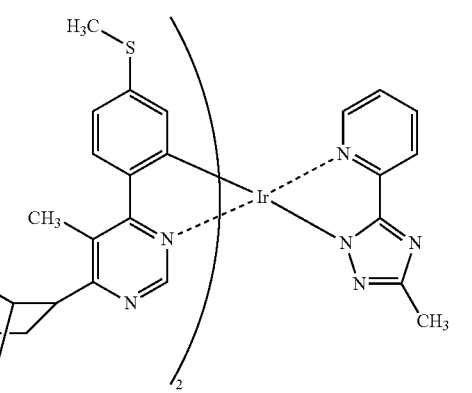
(107)
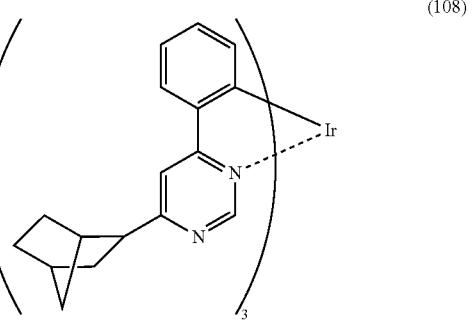
(108)
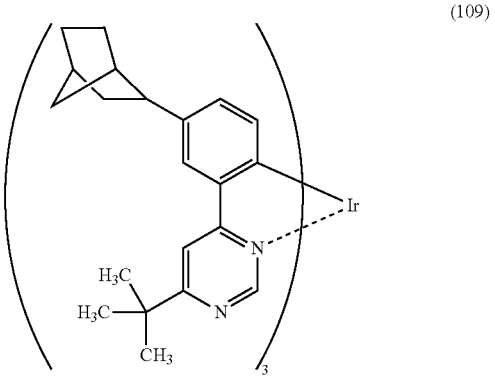
(109)

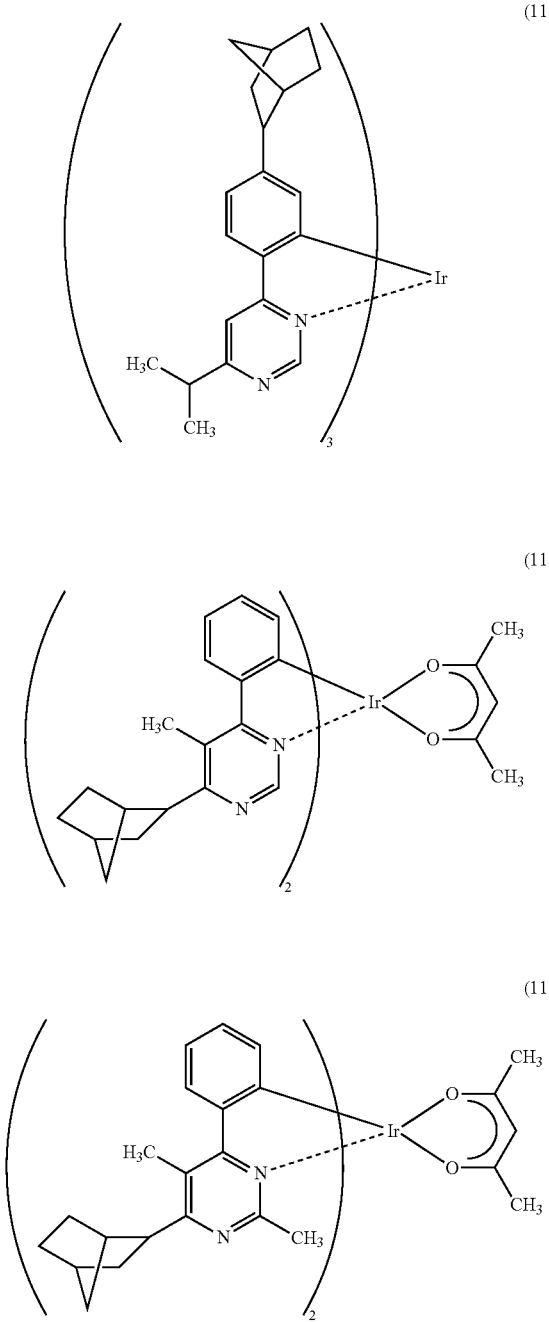
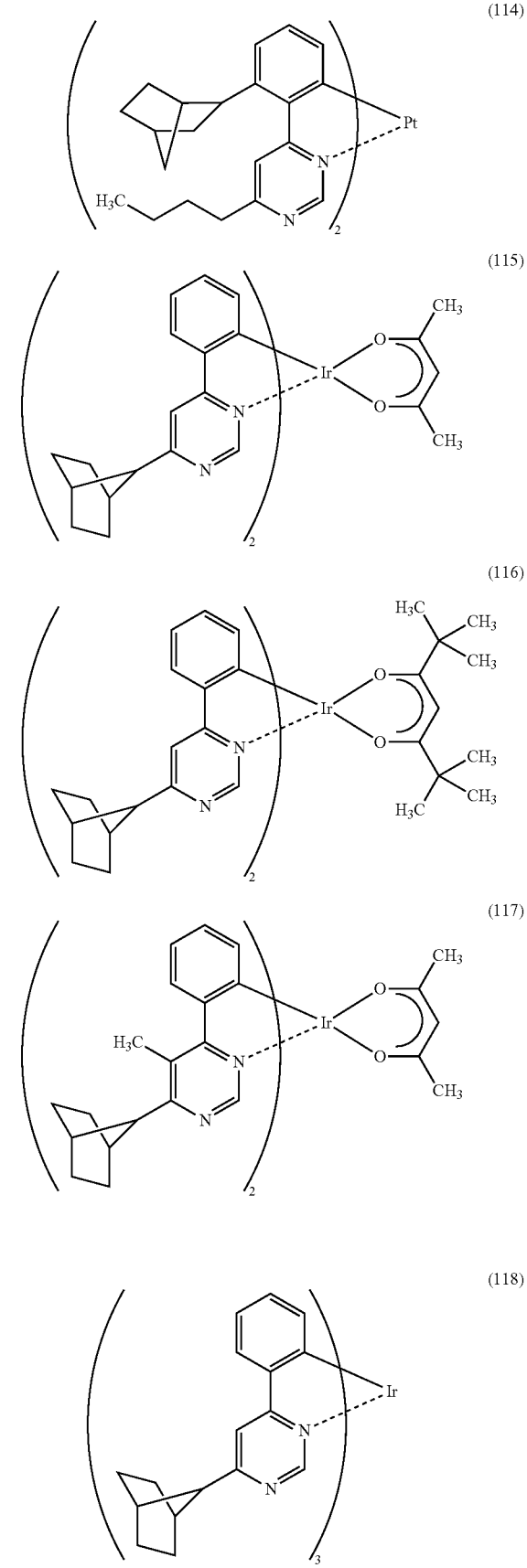

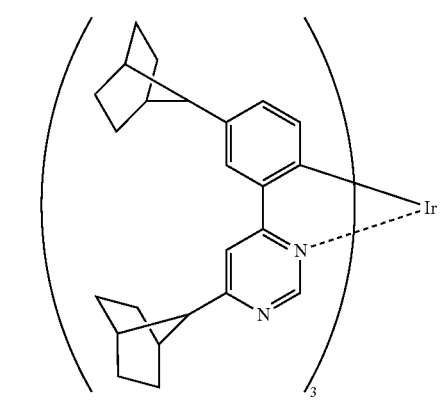
(119)
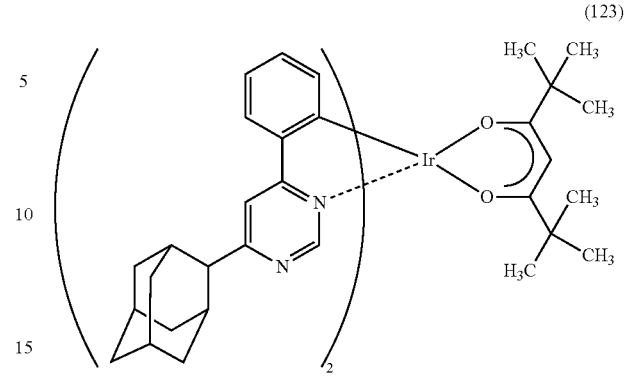
(123)
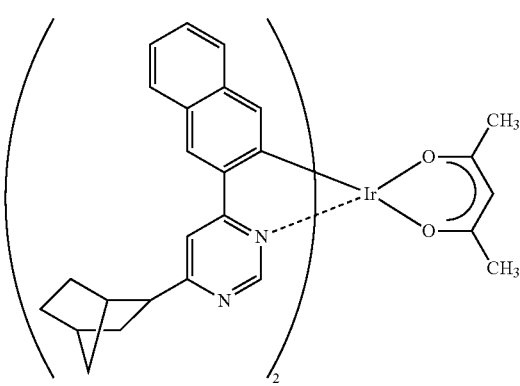
(120)
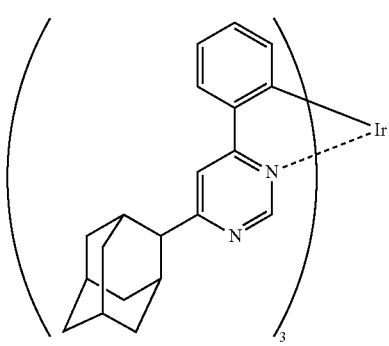
(124)
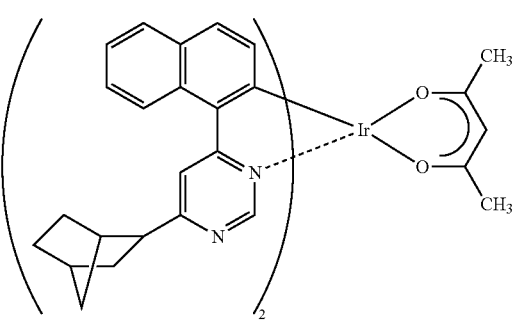
(121)
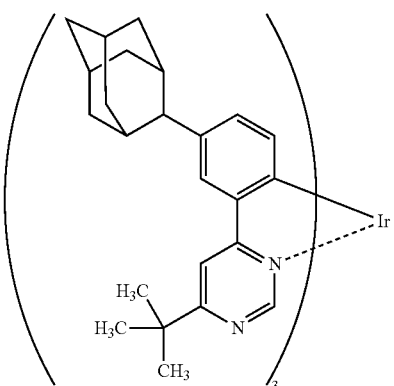
(125)
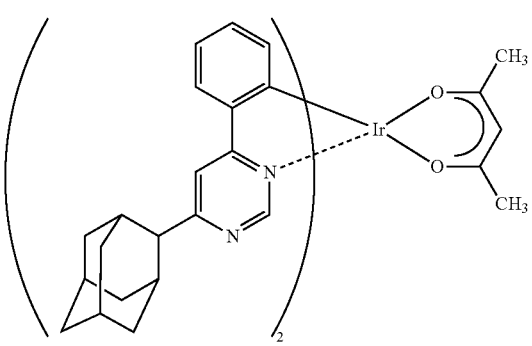
(122)
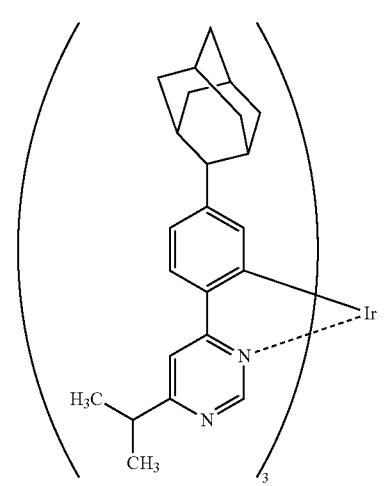
(126)

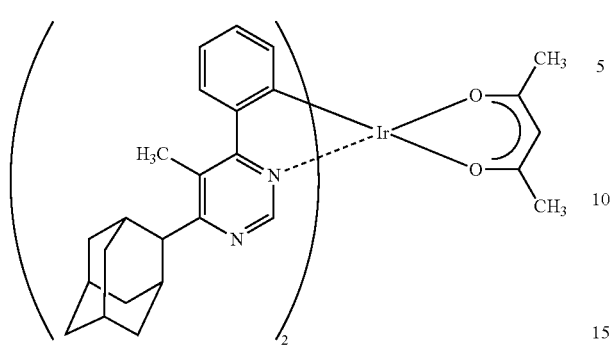
(127)
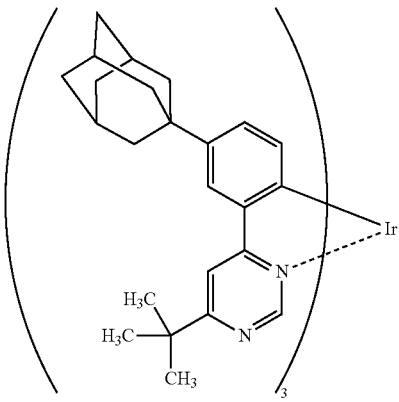
(131)
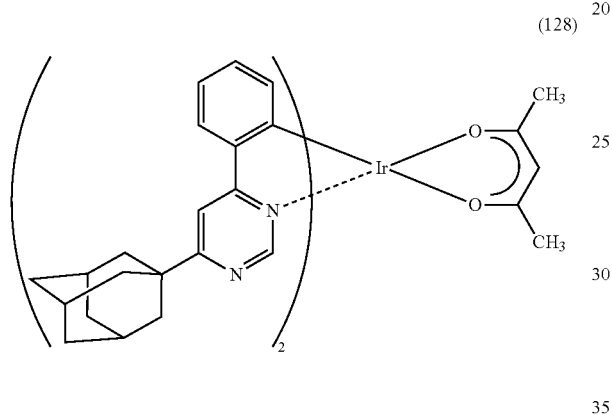
(128)
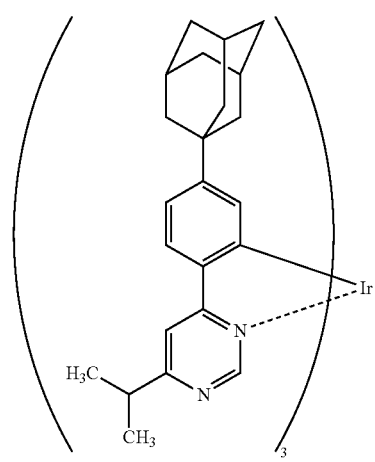
(132)
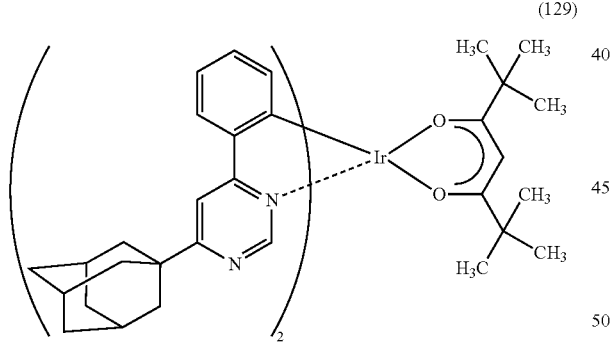
(129)
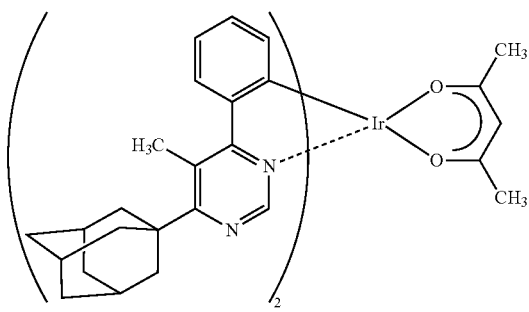
(133)
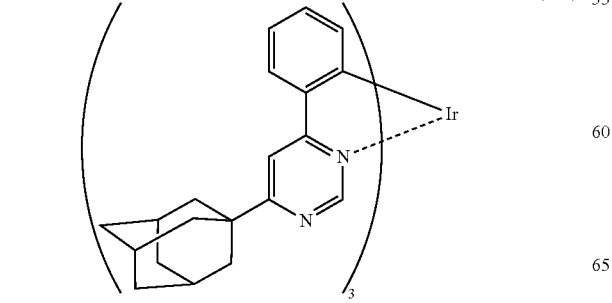
(130)
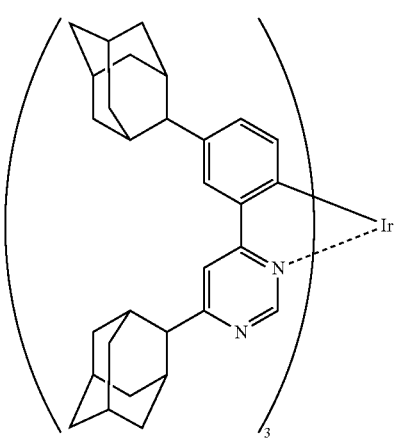
(134)

(135)
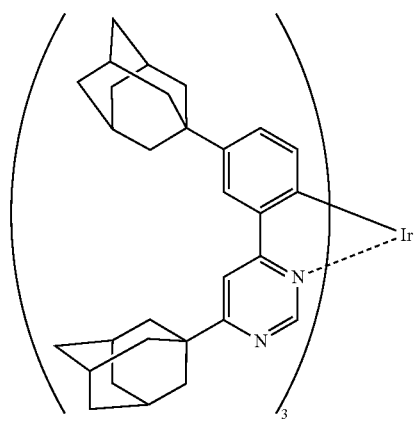

(136)
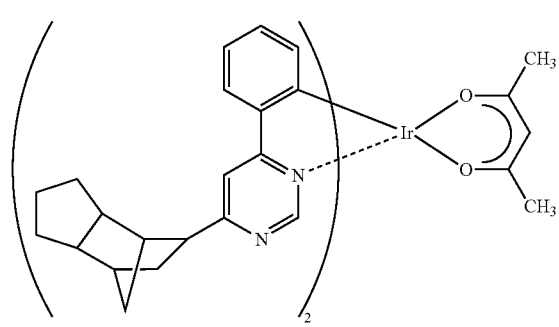

(137)
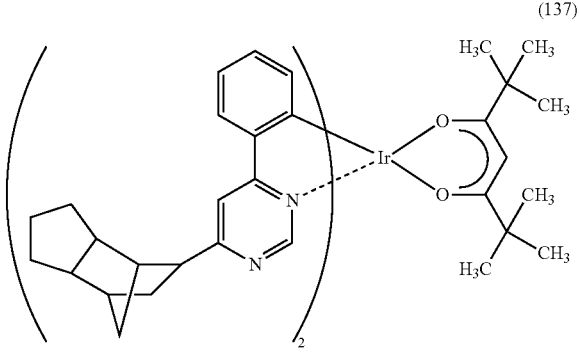

(138)
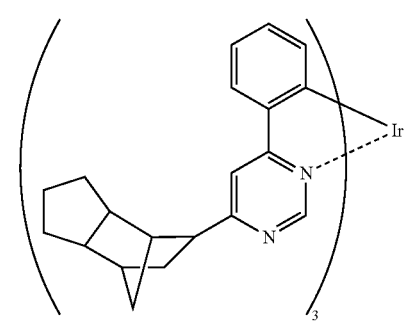

(139)
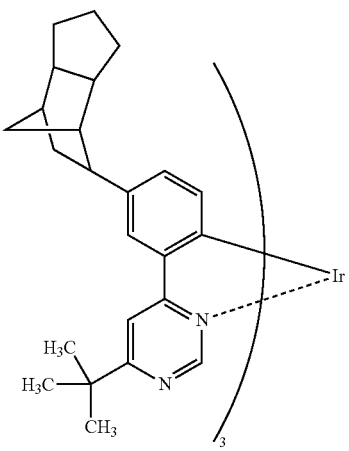

(140)
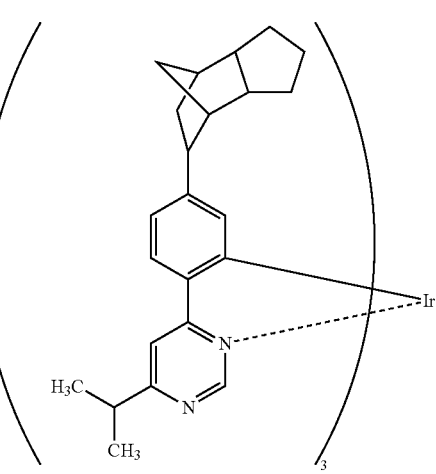

(141)
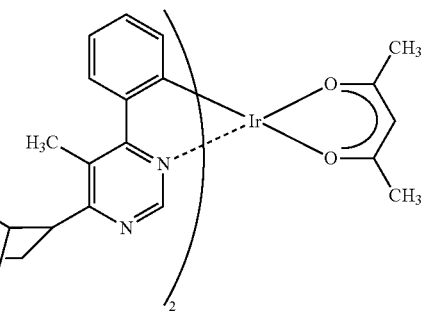

Depending on the type of the ligand, there can be stereoisomers of the organometallic complexes represented by the above structural formulas (100) to (141), and such isomers are included in the category of an organometallic complex according to an embodiment of the invention.

The phosphorescent organometallic complex according to an embodiment of the invention has the following effects.

The tricyclo[5.2.1.0(2,6)]decanyl group, the norbornyl group, or the adamantyl group, which is bonded to a ligand, does not cause the prolongation of the emission wavelength owing to the resonance effect and donates an electron to the ligand owing to the inductive effect. A phosphorescent organometallic complex including a ligand to which an electron is donated has a high molecular absorption coefficient; thus, when it is dispersed in a host material, the phosphorescent organometallic complex can receive energy from the host material efficiently.

Alternatively, with the use of a phosphorescent organometallic complex including a ligand to which a bulky substituent such as tricyclo[5.2.1.0(2,6)]decanyl group, the norbornyl group, and the adamantyl group is bonded, concentration quenching is unlikely to occur because the increased intermolecular distance inhibits the aggregation.

This embodiment can be combined with any of the other embodiments in this specification as appropriate.

(Embodiment 3)

This embodiment shows, with reference to FIGS. 3A and 3B, an example of the structure of a light-emitting element in which a phosphorescent organometallic complex according to an embodiment of the invention is used as a light-emitting organic compound serving as a guest material in a light-emitting layer. The light-emitting element exemplified in this embodiment includes a first electrode, a second electrode, and a layer containing a light-emitting organic compound (hereinafter referred to as EL layer) provided between the first electrode and the second electrode. Note that one of the first electrode and the second electrode functions as an anode, and the other functions as a cathode.

The structure of the EL layer may be appropriately selected in accordance with materials of the first electrode and second electrode. This embodiment shows a light-emitting element including a light-emitting layer in which a first organic compound serves as a host material and in which a second organic compound and a light-emitting organic compound are dispersed as guest materials, and energy generated by recombination of electrons and holes injected into the light-emitting layer results in light emission from the light-emitting organic compound through an excited complex of the first and second organic compounds. With the light-emitting layer having such a structure, energy generated by recombination of electrons and holes can be transferred to the light-emitting organic compound with high efficiency, so that a high-efficiency light-emitting element can be configured.

[Behavior of the Host Material in the Light-Emitting Layer]

The behavior of the host material in the light-emitting layer exemplified in this embodiment is described in comparison with the behavior of a host material in a traditional light-emitting layer, with reference to FIGS. 3A and 3B.

First, the behavior of the host material in the traditional light-emitting layer is shown in FIG. 3A. Here, description is made on a structure in which the light-emitting organic compound is dispersed as the guest material in the first organic compound (represented by H) serving as the host material. Unless a later described combination for forming an excited complex is used, the same description can be applied to a structure in which a plurality of guest materials are dispersed in the host material.

In the traditional light-emitting layer, the organic compound H serving as the host material is excited by energy generated by recombination of electrons and holes, so that a singlet excited state of the organic compound $H^*_{(S1)}$ and a triplet excited state of the organic compound $H^*_{(T1)}$ are produced. Note that the production probability is 25:75 (=$H^*_{(S1)}$: $H^*_{(T1)}$). In general, the singlet excited state of the organic compound $H^*_{(S1)}$ has a higher energy than the triplet excited state of the organic compound $H^*_{(T1)}$, and further, a transition from the singlet excited state to the triplet excited state is a forbidden transition. As a result, as shown in FIG. 3A, the light-emitting layer contains two types of excited species in different energy states (energy state E1 and energy state E2).

Next, the behavior of the host material in the light-emitting layer exemplified in this embodiment is shown in FIG. 3B. The light-emitting layer exemplified in this embodiment contains the first organic compound (represented by A) as the host material and the second organic compound (represented by B) and the light-emitting compound as the guest materials. Here, description is made on a case in which one type of the second organic compound in addition to the light-emitting organic compound are used as the guest materials; however, in some cases, the same description can be made on a case in which two or more types of second organic compounds in addition to the light-emitting organic compound are used or a case including one type of the first organic compound which is able to undergo intramolecular charge transfer in the excited state.

In the light-emitting layer exemplified in this embodiment, the first organic compound A serving as the host material is excited by energy generated by recombination of electrons and holes, and a singlet excited state of the first organic compound $A^*_{(S1)}$ and a triplet excited state of the first organic compound $A^*_{(T1)}$ are produced. Note that the production probability is 25:75 (=$A^*_{(S1)}$:$A^*_{(T1)}$). In general, the singlet excited state of the first organic compound $A^*_{(S1)}$ has a higher energy than the triplet excited state of the first organic compound $A^*_{(T1)}$, and further, a transition from the singlet excited state to the triplet excited state is a forbidden transition.

Next, the singlet excited state of the first organic compound $A^*_{(S1)}$ and a ground state of the second organic compound $B_{(S0)}$ existing in the same layer donate and accept electrons therebetween to form an excited complex AB*.

Here, when the second organic compound B is selected as appropriate, the energy of the excited complex AB* to be formed can be adjusted. Further, the energy of the singlet excited state of the first organic compound $A^*_{(S1)}$ can be reduced to substantially the same level as the energy of the triplet excited state of the first organic compound $A^*_{(T1)}$. As a result, as shown in FIG. 3B, the light-emitting layer exemplified in this embodiment contains excited species in substantially the same energy states (energy state E1). In other words, the energy generated by recombination of electrons and holes can be substantially concentrated to one state.

There is another process of forming the excited complex AB*. Specifically, there is a case where electrons and holes injected into the light-emitting layer generates a combination of a reduced first organic compound A and an oxidized second organic compound B or a combination of an oxidized first organic compound A and a reduced second organic compound B, and then either of the combinations directly forms the excited complex AB*. In any case, the energy substantially concentrated to one state is transferred to the light-emitting organic compound with high efficiency, resulting in light emission.

[Behavior of the Guest Material in the Light-Emitting Layer]

The following shows the behavior of the light-emitting organic compound dispersed as a guest material in the light-emitting layer exemplified in this embodiment. Here, a process in which energy is transferred from an excited state of the host material to the light-emitting organic compound is described.

The process in which energy is transferred from the excited state of the host material to the light-emitting organic compound has the Förster mechanism (dipole-dipole interaction) and the Dexter mechanism (electron exchange interaction). In either mechanism, it is known that a rate constant of energy transfer is increased with increasing combination where the integral value of the product of a normalized emission spectrum of an excited species which donates energy and an absorption spectrum of a guest material which accepts energy. In other words, it is known that the energy transfer is more likely to occur as the overlap between a normalized emission of the excited species and an absorption of the light-emitting organic compound becomes larger.

In the light-emitting layer exemplified in this embodiment, the excited complex of the first organic compound A serving as the host material and the second organic compound B is formed, and the energy generated by recombination of electrons and holes is substantially concentrated to one state (energy state E1). Accordingly, by selectively using, as the light-emitting organic compound, a material whose absorption spectrum largely overlaps with the emission spectrum from the energy state E1, the energy substantially concentrated to one state can be transferred to the light-emitting organic compound with high efficiency. Further, by selecting a material with high emission efficiency as the light-emitting organic compound as appropriate, it is possible to provide a light-emitting element in which the energy generated by recombination of electrons and holes is used for light emission efficiently.

[Material that can be Used for the Light-Emitting Layer According to this Embodiment]

The following shows examples of a material that can be used for a structure including a light-emitting layer in which a second organic compound and a light-emitting organic compound are dispersed as guest materials in a first organic compound serving as a host material, and energy generated by recombination of electrons and holes injected into the light-emitting layer is used for light emission of the light-emitting organic compound through an excited complex of the first and second organic compounds.

As a combination of the first organic compound serving as the host material and the second organic compound that forms the excited complex with the excited state of the first organic compound, a combination of a compound which is likely to accept electrons (electron-trapping compound) and a compound which is likely to accept holes (hole-trapping compound) is preferable. However, the combination of the first organic compound and the second organic compound is not limited to this, and it is also possible to use any combination as long as the excited complex can be formed, an emission spectrum of the excited complex largely overlaps with an absorption spectrum of the light-emitting organic compound dispersed in the host material, and the peak of the emission spectrum of the excited complex is located at a longer wavelength than that of the absorption spectrum of the phosphorescent compound.

Note that when a compound which is likely to accept electrons is used as the first organic compound and a compound which is likely to accept holes is used as the second organic compound, the carrier balance can be controlled by mixture ratio thereof. That is, according to an embodiment of the invention, by the mixture ratio, the recombination probability of holes and electrons in the light-emitting layer can be increased and an optimal balance can be designed in order to increase the emission efficiency. In terms of the carrier balance and formation of the excited complex, the proportion of the first organic compound and the proportion of the second organic compound are preferably not significantly different from each other. Specifically, the ratio of the first organic compound to the second organic compound is preferably 1:9 to 9:1.

Examples of the compound which is likely to accept electrons include benzoquinoxaline derivatives such as 2-[3-(dibenzothiophen-4-yl)phenyl]dibenzo[f,h]quinoxaline (abbreviation: 2mDBTPDBq-II), 2-[4-(3,6-diphenyl-9H-carbazol-9-yl)phenyl]dibenzo[f,h]quinoxaline (abbreviation: 2CzPDBq-III), 7-[3-(dibenzothiophen-4-yl)phenyl]dibenzo[f,h]quinoxaline (abbreviation: 7mDBTPDBq-II), and 6-[3-(dibenzothiophen-4-yl)phenyl]dibenzo[f,h]quinoxaline (abbreviation: 6mDBTPDBq-II).

Examples of the compound which is likely to accept holes include aromatic amine derivatives and carbazole derivatives such as 4-phenyl-4'-(9-phenyl-9H-carbazol-3-yl)triphenylamine (abbreviation: PCBA1BP), 3-[N-(1-naphthyl)-N-(9-phenylcarbazol-3-yl)amino]-9-phenylcarbazole (abbreviation: PCzPCN1), 4,4',4"-tris[N-(1-naphthyl)-N-phenylamino]triphenylamine (abbreviation: 1'-TNATA), 2,7-bis[N-(4-diphenylaminophenyl)-N-phenylamino]-spiro-9,9'-bifluorene (abbreviation: DPA2SF), N,N'-bis(9-phenylcarbazol-3-yl)-N,N'-diphenylbenzene-1,3-diamine (abbreviation: PCA2B), N-(9,9-dimethyl-2-N',N'-diphenylamino-9H-fluoren-7-yl)diphenylamine (abbreviation: DPNF), N,N',N"-triphenyl-N,N',N"-tris(9-phenylcarbazol-3-yl)benzene-1,3,5-triamine (abbreviation: PCA3B), 2-[N-(9-phenylcarbazol-3-yl)-N-phenylamino]spiro-9,9'-bifluorene (abbreviation: PCASF), 2-[N-(4-diphenylaminophenyl)-N-phenylamino]spiro-9,9'-bifluorene (abbreviation: DPASF), N,N'-bis[4-(carbazol-9-yl)phenyl]-N,N'-diphenyl-9,9-dimethylfluorene-2,7-diamine (abbreviation: YGA2F), 4,4'-bis[N-(3-methylphenyl)-N-phenylamino]biphenyl (abbreviation: TPD), 4,4'-bis[N-(4-diphenylaminophenyl)-N-phenylamino]biphenyl (abbreviation: DPAB), N-(9,9-dimethyl-9H-fluoren-2-yl)-N-{9,9-dimethyl-2-[N'-phenyl-N'-(9,9-dimethyl-9H-fluoren-2-yl)amino]-9H-fluoren-7-yl}phenylamine (abbreviation: DFLADFL), 3-[N-(9-phenylcarbazol-3-yl)-N-phenylamino]-9-phenylcarbazole (abbreviation: PCzPCA1), 3-[N-(4-diphenylaminophenyl)-N-phenylamino]-9-phenylcarbazole (abbreviation: PCzDPA1), 3,6-bis[N-(4-diphenylaminophenyl)-N-phenylamino]-9-phenylcarbazole (abbreviation: PCzDPA2), 4,4'-bis(N-{4-[N'-(3-methylphenyl)-N'-phenylamino]phenyl}-N-phenylamino)biphenyl (abbreviation: DNTPD), 3,6-bis[N-(4-diphenylaminophenyl)-N-(1-naphthyl)amino]-9-phenylcarbazole (abbreviation: PCzTPN2), and 3,6-bis[N-(9-phenylcarbazol-3-yl)-N-phenylamino]-9-phenylcarbazole (abbreviation: PCzPCA2).

As the light-emitting organic compound, a phosphorescent compound is preferable, and in particular, an iridium complex is preferable among organometallic complexes. In consideration of energy transfer due to Förster mechanism described above, the molar absorption coefficient of the absorption band in the longest wavelength region of the phosphorescent compound is preferably 2000 $M^{-1} \cdot cm^{-1}$ or higher, more preferably 5000 $M^{-1} \cdot cm^{-1}$ or higher.

Examples of the light-emitting organic compound having such a high molar absorption coefficient are bis(3,5-dimethyl-2-phenylpyrazinato)(dipivaloylmethanato)iridium(III) (abbreviation: Ir(mppr-Me)$_2$(dpm)), (acetylacetonato)bis(4,6-diphenylpyrimidinato)iridium(III) (abbreviation: Ir(dppm)$_2$(acac)), and the like.

The phosphorescent organometallic iridium complex according to an embodiment of the present invention (refer to Embodiment 2) can be suitably used for a light-emitting element, and is preferably (acetylacetonato)bis[4-(2-norbornyl)-6-phenylpyrimidinato]iridium(III) (endo- and exo-mixture) (abbreviation: [Ir(nbppm)$_2$(acac)]), for example.

In the above manner, it is possible to fabricate a light-emitting element including a light-emitting layer in which a first organic compound serves as a host material and in which a second organic compound and a light-emitting organic compound are dispersed as guest materials, and energy generated by recombination of electrons and holes injected into the light-emitting layer results in light emission from the light-emitting organic compound through an excited complex of the first and second organic compounds.

In the light-emitting element exemplified in this embodiment, energy generated by recombination of electrons and holes injected into the light-emitting layer is substantially concentrated to one state and then transferred to the light-emitting organic compound. As a result, energy can be transferred from the host material to the light-emitting organic compound with high efficiency. Further, with the use of the phosphorescent organometallic complex with high emission efficiency according to an embodiment of the invention, it is possible to provide a light-emitting element in which energy generated by recombination of electrons and holes is used for light emission efficiently.

This embodiment can be combined with any of the other embodiments in this specification as appropriate.

(Embodiment 4)

This embodiment shows, with reference to FIGS. 4A and 4B and FIGS. 5A and 5B, light-emitting devices each including a light-emitting element in which a phosphorescent organometallic complex according to an embodiment of the invention is applied to a layer which is provided between a pair of electrodes and which contains a light-emitting organic compound. Specifically, an active matrix light-emitting device and a passive matrix light-emitting device are described.

[Active Matrix Light-Emitting Device]

FIGS. 4A and 4B illustrate the structure of an active matrix light-emitting device to which the light-emitting element is applied. FIG. 4A is a top view of the light-emitting device, and FIG. 4B is a cross-sectional view taken along lines A-B and C-D in FIG. 4A.

An active matrix light-emitting device 1400 includes a driver circuit portion (source side driver circuit) 1401, a pixel portion 1402, a driver circuit portion (gate side driver circuit) 1403, a sealing substrate 1404, and a sealing member 1405 (see FIG. 4A). Note that a portion enclosed by the sealing member 1405 is a space 1407 (see FIG. 4B).

The light-emitting device 1400 receives a video signal, a clock signal, a start signal, a reset signal, and the like from an FPC (flexible printed circuit) 1409 that is an external input terminal. Note that only the FPC is illustrated here; however, the FPC may be provided with a printed wiring board (PWB). The light-emitting device in this specification includes, in its category, not only the light-emitting device itself but also the light-emitting device provided with the FPC or the FPC and the PWB.

Next, the structure of the light-emitting device 1400 is described with reference to the cross-sectional view of FIG. 4B. The light-emitting device 1400 includes a driver circuit portion including the source side driver circuit 1401 illustrated over an element substrate 1410 and the pixel portion 1402 including a pixel illustrated. Further, it includes a lead wiring 1408 for transmitting signals that are to be inputted to the source side driver circuit 1401 and the gate side driver circuit 1403.

Note that in this embodiment, the source side driver circuit 1401 includes a CMOS circuit in which an n-channel TFT 1423 and a p-channel TFT 1424 are combined; however, the driver circuit is not limited to this structure, and the driver circuit may be any of a variety of circuits, such as a CMOS circuit, a PMOS circuit, or an NMOS circuit. Although this embodiment illustrates a driver-integrated type where the driver circuit is Ruined over the substrate, the invention is not limited to this, and the driver circuit may be formed outside the substrate, not over the substrate.

The pixel portion 1402 is formed using the light-emitting element according to an embodiment of the invention. The pixel portion 1402 includes a plurality of pixels having a switching TFT 1411, a current control TFT 1412, and a first electrode 1413 electrically connected to a drain of the current control TFT 1412. For the pixel portion 1402, for example, the light-emitting element exemplified in Embodiment 1 can be employed. Specifically, a structure in which a switching TFT is provided in each of the light-emitting elements included in the pixel portion 1402 may be employed. Note that a partition 1414 is formed so as to cover an end portion of the first electrode 1413. Here, the partition 1414 is formed using a positive type photosensitive acrylic resin film.

The partition 1414 is formed to have a curved surface with curvature at an upper end or a lower end thereof. For example, when a positive photosensitive acrylic resin is used as a material for the partition 1414, it is preferable that only an upper edge portion of the partition 1414 have a curved surface with a radius of curvature (0.2 μm to 3 μm). The partition 1414 can be formed using either a negative type photosensitive resin which becomes insoluble in an etchant by light irradiation or a positive type photosensitive resin which becomes soluble in an etchant by light irradiation.

The light-emitting device 1400 includes a second electrode 1417 provided over the first electrode 1413 and an EL layer 1416 between the first electrode 1413 and the second electrode 1417. As a structure of the light-emitting element 1418, the light-emitting element exemplified in Embodiment 1 can be employed, for example.

The light-emitting device 1400 exemplified in this embodiment has a structure in which the light-emitting element 1418 is sealed in the space 1407 enclosed by the element substrate 1410, the sealing substrate 1404, and the sealing member 1405. Note that the space 1407 is filled with a filler. There are cases where the space 1407 is filled with an inert gas (such as nitrogen or argon) or the sealing member 1405. Further, a material for adsorbing an impurity, such as a desiccant, may be provided.

The sealing member 1405 and the sealing substrate 1404 are desirably formed using a material which does not transmit an impurity in the air (e.g., moisture or oxygen) as much as possible. As the sealing substrate 1404, in addition to a glass substrate or a quartz substrate, a plastic substrate formed using fiberglass-reinforced plastics (FRP), polyvinyl fluoride) (PVF), a polyester, an acrylic resin, or the like can be given. As the sealing member 1405, typically, an epoxy-based resin is preferably used.

The above-described active matrix light-emitting device according to an embodiment of the invention includes a light-emitting element in which a phosphorescent organometallic complex according to an embodiment of the invention is applied to an EL layer which is provided between a pair of electrodes. The phosphorescent organometallic complex has a 6-membered aromatic heterocycle containing a nitrogen atom, such as pyridine and monocyclic diazine and iridium or platinum, where the nitrogen atom coordinates to the iridium or the platinum, an ortho-metalated aryl group is bonded to an α-carbon atom of the nitrogen atom, and the 6-membered aromatic heterocycle or the aryl group has any one of a tricyclo[5.2.1.0(2,6)]decanyl group, a norbornyl group, and an adamantyl group as a substituent. Therefore, a light-emitting device with high emission efficiency and low power consumption can be provided.

[Passive Matrix Light-Emitting Device]

Figure 5A:
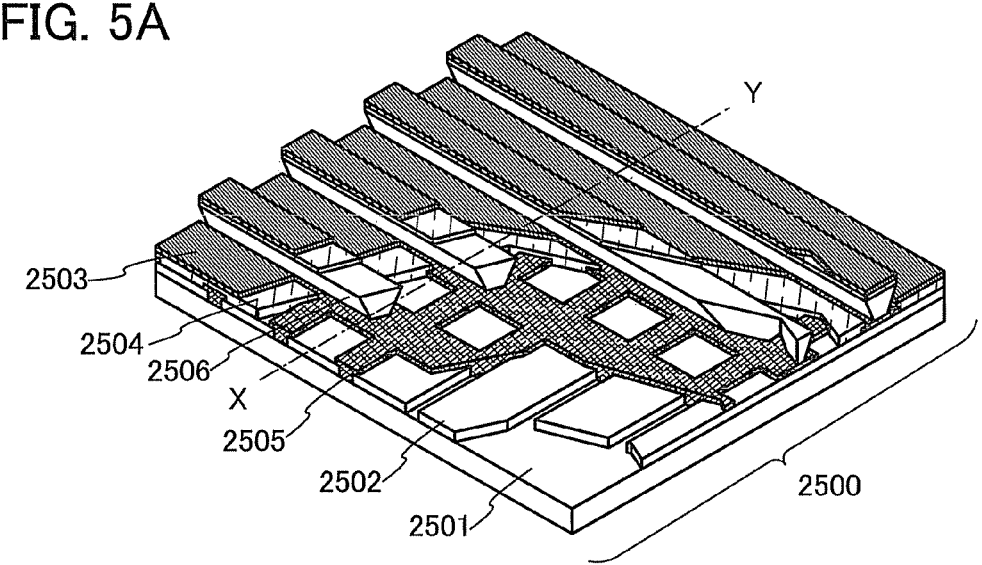
FIGS. 5A and 5B illustrate a light-emitting device according to an embodiment.
Figure 5B:
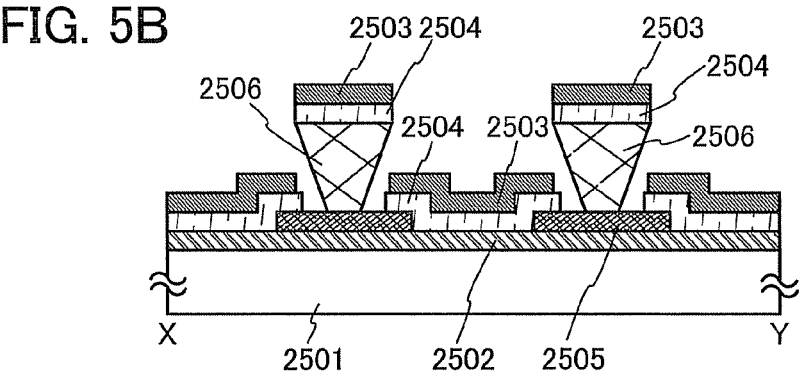

Next, FIGS. 5A and 5B illustrate the structure of a passive matrix light-emitting device to which the light-emitting element is applied. FIG. 5A is a perspective view of the light-emitting device, and FIG. 5B is a cross-sectional view taken along a line X-Y of FIG. 5A.

A passive matrix light-emitting device 2500 includes a first electrode 2502 over a substrate 2501. Further, an insulating layer 2505 is provided so as to cover an end portion of the first electrode 2502, and a partition layer 2506 is provided over the insulating layer 2505.

The light-emitting device 2500 is formed using the light-emitting element according to an embodiment of the invention. For the light-emitting element, for example, the light-emitting element exemplified in Embodiment 1 can be employed. The light-emitting element includes a second electrode 2503 provided over the first electrode 2502 and an EL layer 2504 between the first electrode 2502 and the second electrode 2503.

Sidewalls of the partition layer 2506 have a slant such that the distance between one sidewall and the other sidewall becomes narrower as the sidewalls gets closer to a surface of the substrate. That is, a cross section of the partition layer 2506 in a short-side direction is trapezoid-like, in which a bottom side (side in a direction similar to a surface direction of the insulating layer 2505, which is in contact with the insulating layer 2505) is shorter than an upper side (side in a direction similar to the surface direction of the insulating layer 2505, which is not in contact with the insulating layer 2505). With the partition layer 2506 provided in such a way, a defect of a light-emitting element due to crosstalk or the like can be prevented.

The above-described passive matrix light-emitting device according to an embodiment of the invention includes a light-emitting element in which a phosphorescent organometallic complex according to an embodiment of the invention is applied to an EL layer which is provided between a pair of electrodes. The phosphorescent organometallic complex has a 6-membered aromatic heterocycle containing a nitrogen atom, such as pyridine or monocyclic diazine and iridium or platinum, where the nitrogen atom coordinates to the iridium or the platinum, an ortho-metalated aryl group is bonded to an α-carbon atom of the nitrogen atom, and the 6-membered aromatic heterocycle or the aryl group has any one of a tricyclo[5.2.1.0(2,6)]decanyl group, a norbornyl group, and an adamantyl group as a substituent. Therefore, a light-emitting device with high emission efficiency and low power consumption can be provided.

This embodiment can be combined with any of the other embodiments as appropriate.

(Embodiment 5)

This embodiment shows, with reference to FIGS. 6A to 6E, examples of electronic appliances on each of which a light-emitting device is mounted. The light-emitting device includes a light-emitting element in which a phosphorescent organometallic complex according to an embodiment of the invention is applied to an EL layer which is provided between a pair of electrodes.

Examples of the electronic appliances to which the light-emitting device is applied are television devices (also referred to as TV or television receivers), monitors for computers and the like, cameras such as digital cameras and digital video cameras, digital photo frames, cellular phones (also referred to as portable telephone devices), portable game machines, portable information terminals, audio playback devices, large game machines such as pin-ball machines, and the like. Specific examples of these electronic appliances are illustrated in FIGS. 6A to 6E.

Figure 6A:
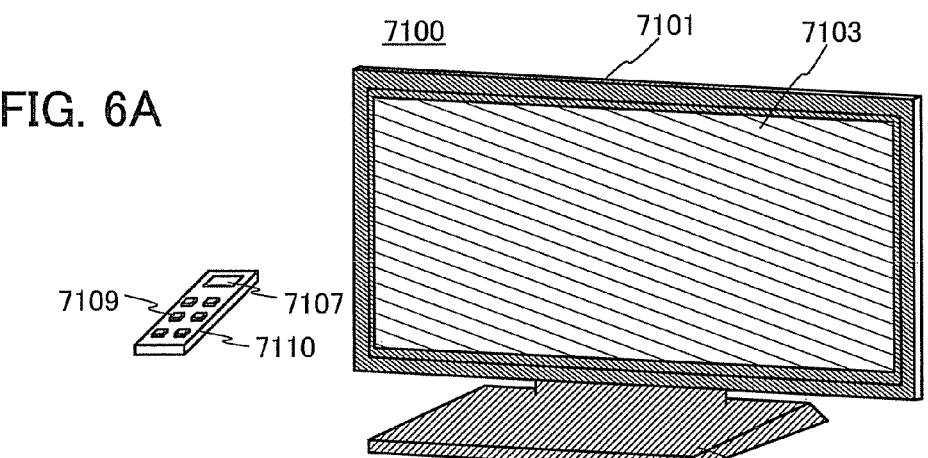
FIGS. 6A to 6E each illustrate an electronic appliance according to an embodiment.

FIG. 6A illustrates an example of a television device. In a television device 7100, a display portion 7103 is incorporated in a housing 7101. Images can be displayed by the display portion 7103, and the light-emitting device can be used for the display portion 7103. In addition, here, the housing 7101 is supported by a stand 7105.

The television device 7100 can be operated by an operation switch of the housing 7101 or a separate remote controller 7110. With operation keys 7109 of the remote controller 7110, channels and volume can be controlled and images displayed on the display portion 7103 can be controlled. Further, the remote controller 7110 may be provided with a display portion 7107 for displaying data output from the remote controller 7110.

Note that the television device 7100 is provided with a receiver, a modem, and the like. With the receiver, a general television broadcast can be received. Furthermore, when the television device 7100 is connected to a communication network by wired or wireless connection via the modem, one-way (from a transmitter to a receiver) or two-way (between a transmitter and a receiver, between receivers, or the like) data communication can be performed.

Figure 6B:
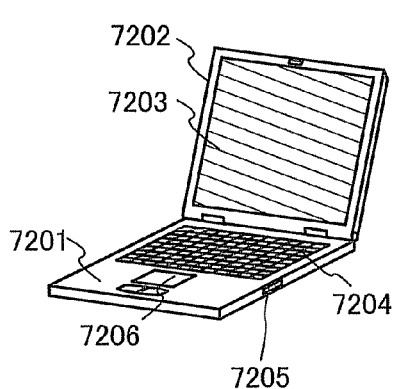

FIG. 6B illustrates a computer, which includes a main body 7201, a housing 7202, a display portion 7203, a keyboard 7204, an external connection port 7205, a pointing device 7206, and the like. This computer is manufactured by using a light-emitting device for the display portion 7203.

Figure 6C:
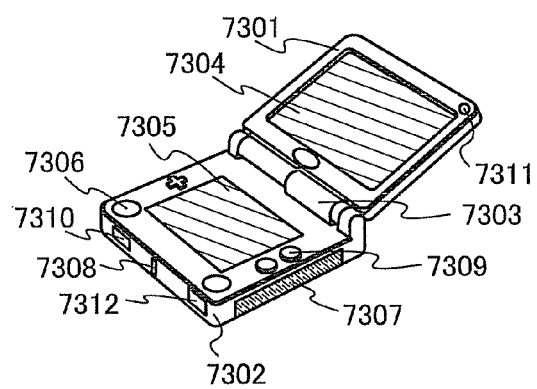

FIG. 6C illustrates a portable game machine having two housings, a housing 7301 and a housing 7302, which are connected with a joint portion 7303 so that the portable game machine can be opened or folded. A display portion 7304 is incorporated in the housing 7301 and a display portion 7305 is incorporated in the housing 7302. In addition, the portable game machine illustrated in FIG. 6C includes a speaker portion 7306, a recording medium insertion portion 7307, an LED lamp 7308, an input unit (an operation key 7309, a connection terminal 7310, a sensor 7311 (sensor having a function of measuring force, displacement, position, speed, acceleration, angular velocity, rotational frequency, distance, light, liquid, magnetism, temperature, chemical substance, sound, time, hardness, electric field, current, voltage, electric power, radiation, flow rate, humidity, gradient, oscillation, odor, or infrared rays), or a microphone 7312), and the like. It is needless to say that the structure of the portable game machine is not limited to the above as long as a light-emitting device is used for at least either the display portion 7304 or the display portion 7305, or both, and may include other accessories as appropriate. The portable game machine illustrated in FIG. 6C has a function of reading a program or data stored in a recording medium to display it in the display portion, and a function of sharing information with another portable game machine by wireless communication. Note that the functions of the portable game machine illustrated in FIG. 6C are not limited to these functions, and the portable game machine can have various functions.

Figure 6D:
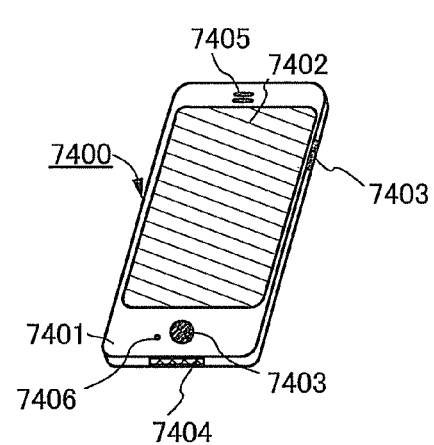

FIG. 6D illustrates an example of a cellular phone. A cellular phone 7400 is provided with a display portion 7402 incorporated in a housing 7401, operation buttons 7403, an external connection port 7404, a speaker 7405, a microphone 7406, and the like. Note that the cellular phone 7400 is manufactured by using a light-emitting device for the display portion 7402.

When the display portion 7402 of the cellular phone 7400 illustrated in FIG. 6D is touched with a finger or the like, data can be input into the cellular phone 7400. Further, operations such as making a call and creating e-mail can be performed by touch on the display portion 7402 with a finger or the like.

There are mainly three screen modes of the display portion 7402. The first mode is a display mode mainly for displaying images. The second mode is an input mode mainly for inputting data such as text. The third mode is a display-and-input mode in which two modes of the display mode and the input mode are combined.

For example, in the case of making a call or creating e-mail, a text input mode mainly for inputting text is selected for the display portion 7402 so that text displayed on a screen can be inputted. In this case, it is preferable to display a keyboard or number buttons on almost the entire screen of the display portion 7402.

When a detection device including a sensor for detecting inclination, such as a gyroscope or an acceleration sensor, is provided inside the cellular phone 7400, display on the screen of the display portion 7402 can be automatically changed by determining the orientation of the cellular phone 7400 (whether the cellular phone is placed horizontally or vertically for a landscape mode or a portrait mode).

The screen modes are switched by touching the display portion 7402 or operating the operation buttons 7403 of the housing 7401. Alternatively, the screen modes can be switched depending on kinds of images displayed on the display portion 7402. For example, when a signal of an image displayed on the display portion is a signal of moving image data, the screen mode is switched to the display mode. When the signal is a signal of text data, the screen mode is switched to the input mode.

Moreover, in the input mode, when input by touching the display portion 7402 is not performed within a specified period while a signal detected by an optical sensor in the display portion 7402 is detected, the screen mode may be controlled so as to be switched from the input mode to the display mode.

The display portion 7402 may function as an image sensor. For example, an image of a palm print, a fingerprint, or the like is taken by touch on the display portion 7402 with the palm or the finger, whereby personal authentication can be performed. Further, by providing a backlight or a sensing light source which emits a near-infrared light in the display portion, an image of a finger vein, a palm vein, or the like can be taken.

Figure 6E:
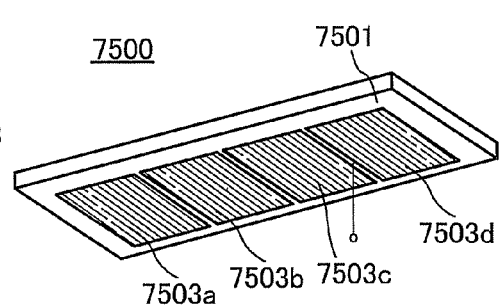

FIG. 6E illustrates an example of a lighting device. In a lighting device 7500, light-emitting devices 7503a to 7503d according to embodiments of the invention are incorporated in a housing 7501 as light sources. The lighting device 7500 can be attached to a ceiling, a wall, or the like.

The light-emitting device according to an embodiment of the invention includes a light-emitting panel in a thin film form. Thus, when the light-emitting device is attached to a base with a curved surface, the light-emitting device with a curved surface can be obtained. In addition, when the light-emitting device is located in a housing with a curved surface, an electronic appliance or lighting device with a curved surface can be obtained.

An electronic appliance according to an embodiment of the invention includes a light emitting element with high emission efficiency; therefore, the power consumption is low.

This embodiment can be combined with any of the other embodiments in this specification as appropriate.
(Embodiment 6)

Figure 7A:
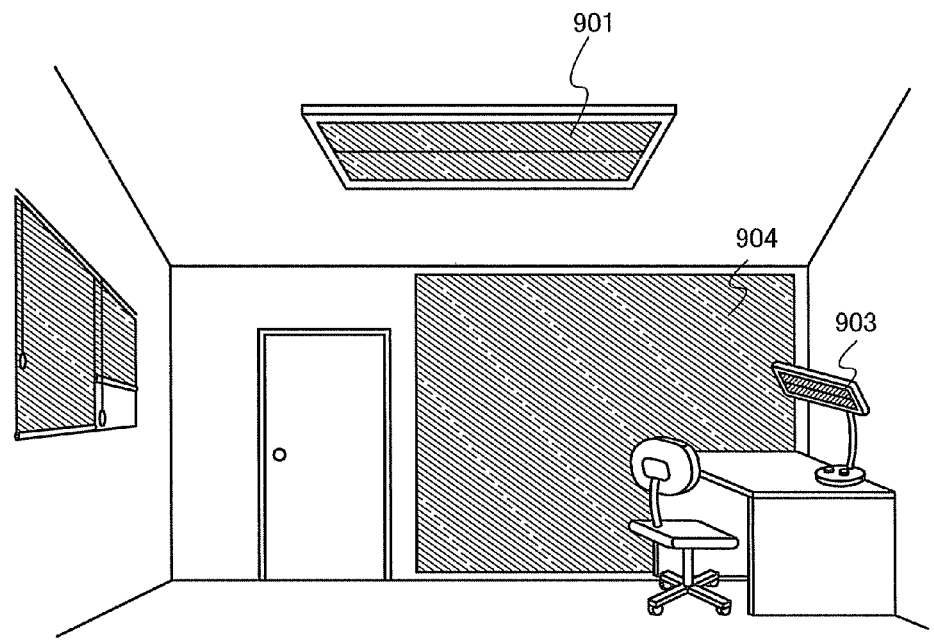
FIGS. 7A and 7B illustrate lighting devices according to an embodiment.
Figure 7B:
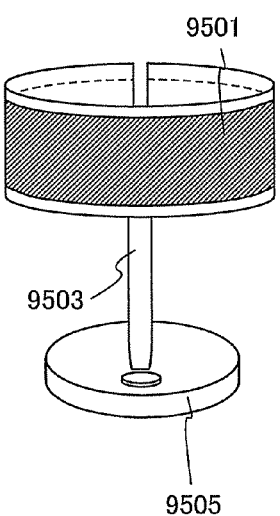

This embodiment shows, with reference to FIGS. 7A and 7B, examples of lighting devices on each of which a light-emitting device is mounted. The light-emitting device includes a light-emitting element in which a phosphorescent organometallic complex according to an embodiment of the invention is applied to an EL layer which is provided between a pair of electrodes.

According to an embodiment of the invention, a lighting device in which a light-emitting portion has a curved surface can also be achieved.

An embodiment of the invention can also be applied to lighting in a car; for example, lighting can be easily mounted on a dashboard, a ceiling, or the like.

FIG. 7A illustrates an interior lighting device 901 provided on a ceiling, a lighting device 904 provided on a wall surface, and a desk lamp 903 to which embodiments of the invention are applied. Since the light-emitting device can be enlarged, the light-emitting device can be used as a large-area lighting device.

FIG. 7B illustrates another example of the lighting device. A desk lamp illustrated in FIG. 7B includes a lighting portion 9501, a support 9503, a support base 9505, and the like. The lighting portion 9501 includes a light-emitting device according to an embodiment of the invention. According to an embodiment of the invention, a lighting device having a curved surface can be achieved.

EXAMPLE 1

Structures, fabrication methods, and results of measurement of characteristics of a light-emitting element according to an embodiment of the invention are described.

Structures of a light-emitting element fabricated in this example are described with reference to FIGS. 8A and 8B, Table 1, and Table 2. Specifically, a light-emitting element in which a phosphorescent organometallic complex according to an embodiment of the present invention is applied to an EL layer which is provided between a pair of electrodes is described.
(Structure of the Light-Emitting Element)

Figure 8A:
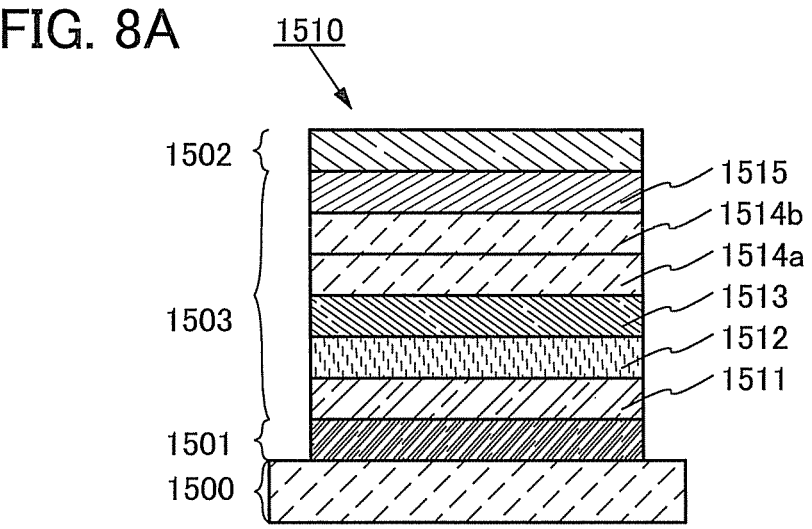
FIGS. 8A and 8B illustrate structures of an element according to an example.

FIG. 8A illustrates an example of the structure of a light-emitting element 1510 which was fabricated. In the light-emitting element 1510, an EL layer 1503 is provided between a first electrode 1501 and a second electrode 1502. The first electrode 1501 transmits light emitted from the EL layer 1503, which is reflected by the second electrode 1502.

In this example, the first electrode 1501 was formed as an anode using an indium tin oxide film containing silicon (abbreviation: ITSO film) over a glass substrate 1500. The second electrode 1502 was formed as a cathode using an aluminum film.
(Structure of the Layer Containing a Light-Emitting Organic Compound)

FIG. 8A illustrates the structure of the EL layer 1503. The EL layer 1503 includes a hole-injection layer 1511, a hole-transport layer 1512, a light-emitting layer 1513, a first electron-transport layer 1514a, a second electron-transport layer 1514b, and an electron-injection layer 1515 stacked in that order over the first electrode 1501 serving as the anode.

In this example, three types of light-emitting elements were fabricated by changing the light-emitting organic compound contained in the light-emitting layer of the light-emitting element 1510 having the above structure. Specifically, light-emitting elements (light-emitting elements 1 and 2) according to embodiments of the invention and a comparative element were fabricated in order to show an effect of the light-emitting element in comparison with the comparative element. Detailed structures of the elements fabricated are shown in Table 1.

TABLE 1

| EL Layer | HIL 1511 | HTL 1512 | Light-Emitting Layer 1513 | ETL 1514a | ETL 1514b | EIL 1515 |
|---|---|---|---|---|---|---|
| Light-Emitting Element 1 | DBT3P-II:MoOx (= 2:1) 40 nm | BPAFLP 20 nm | 2mDBTPDBq-II:PCBA1BP:Ir(nbppm)$_2$(acac) (= 0.8:0.2:0.05) 40 nm | 2mDBTPDBq-II 10 nm | Bphen 20 nm | LiF 1 nm |
| Light-Emitting Element 2 | DBT3P-II:MoOx (= 2:1) 40 nm | BPAFLP 20 nm | 2mDBTPDBq-II:PCBA1BP:Ir(nbppm)$_2$(acac) (= 0.8:0.2:0.01) 40 nm | 2mDBTPDBq-II 10 nm | Bphen 20 nm | LiF 1 nm |
| Comparative Element | DBT3P-II:MoOx (= 2:1) 40 nm | BPAFLP 20 nm | 2mDBTPDBq-II:PCBA1BP:Ir(tBuppm)$_2$(acac) (= 0.8:0.2:0.05) 40 nm | 2mDBTPDBq-II 10 nm | Bphen 20 nm | LiF 1 nm |

Figure 8B:
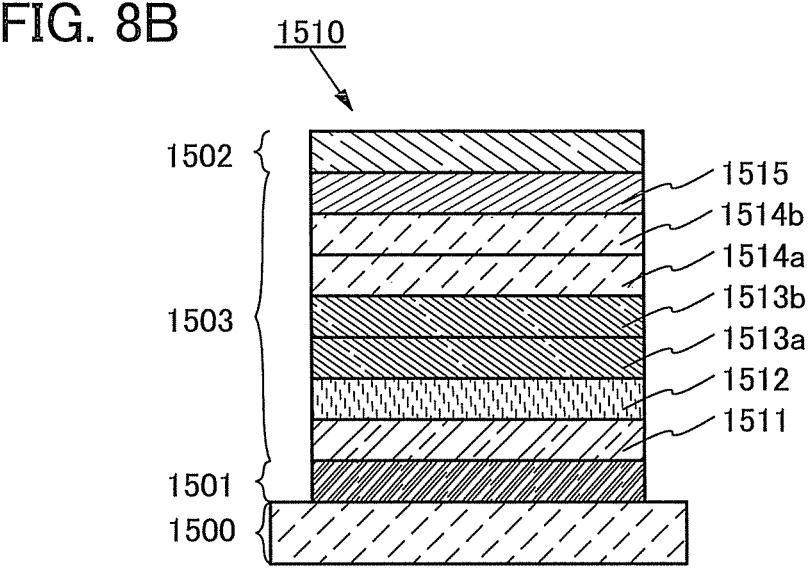

The light-emitting element according to an embodiment of the invention may be a light-emitting element in which the light-emitting layer 1513 is a two-layered body (see FIG. 8B). Specifically, the light-emitting element according to an embodiment of the invention may also employ a structure in which the light-emitting layer 1513 includes a first light-emitting layer 1513a in contact with the hole-transport layer 1512 and a second light-emitting layer 1513b in contact with the first electron-transport layer 1514a. In this example, a light-emitting element (light-emitting element 3) in which the light-emitting layer 1513 is a two-layered body was also fabricated. Detailed structures of the light-emitting element 3 are shown in Table 2.

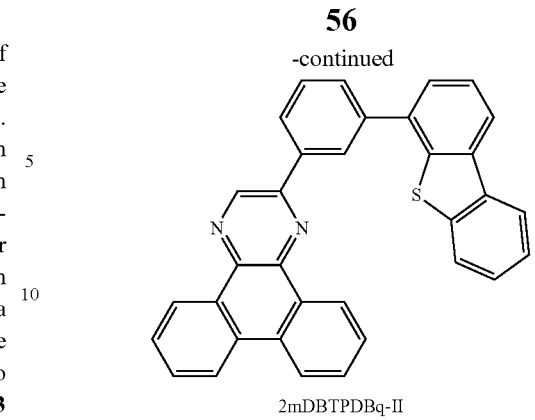

2mDBTPDBq-II

TABLE 2

| | HIL | HTL | Light-Emitting Layer | | ETL | | EIL |
|---|---|---|---|---|---|---|---|
| EL Layer | 1511 | 1512 | 1513a | 15133b | 1514a | 1514b | 1515 |
| Light-Emitting Element 3 | DBT3P-II:MoOx (= 2:1) 40 nm | BPAFLP 20 nm | 2mDBTPDBq-II:PCBA1BP:Ir(nbmppm)$_2$(acac) (= 0.8:0.2:0.05) 20 nm | 2mDBTPDBq-II:PCBA1BP:Ir(nbmppm)$_2$(acac) (= 0.8:0.2:0.01) 20 nm | 2mDBTPDBq-II 10 nm | Bphen 20 nm | LiF 1 nm |

Structural formulas of some organic compounds used in this example are shown below.

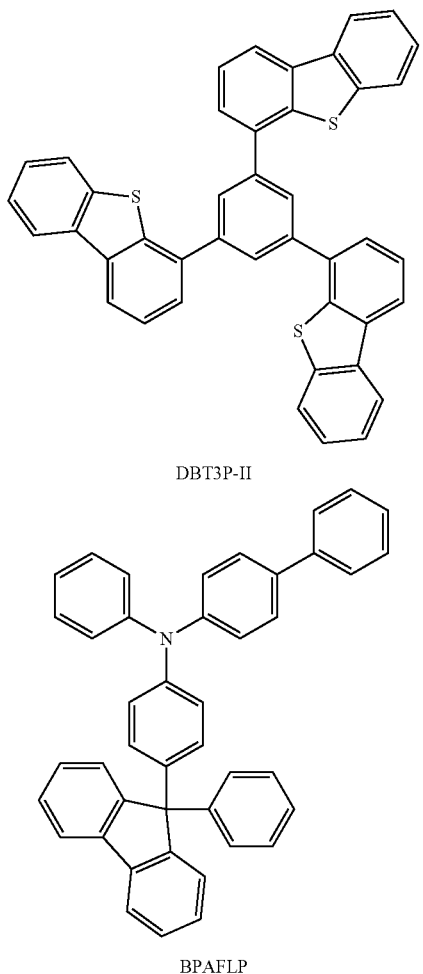

DBT3P-II

BPAFLP

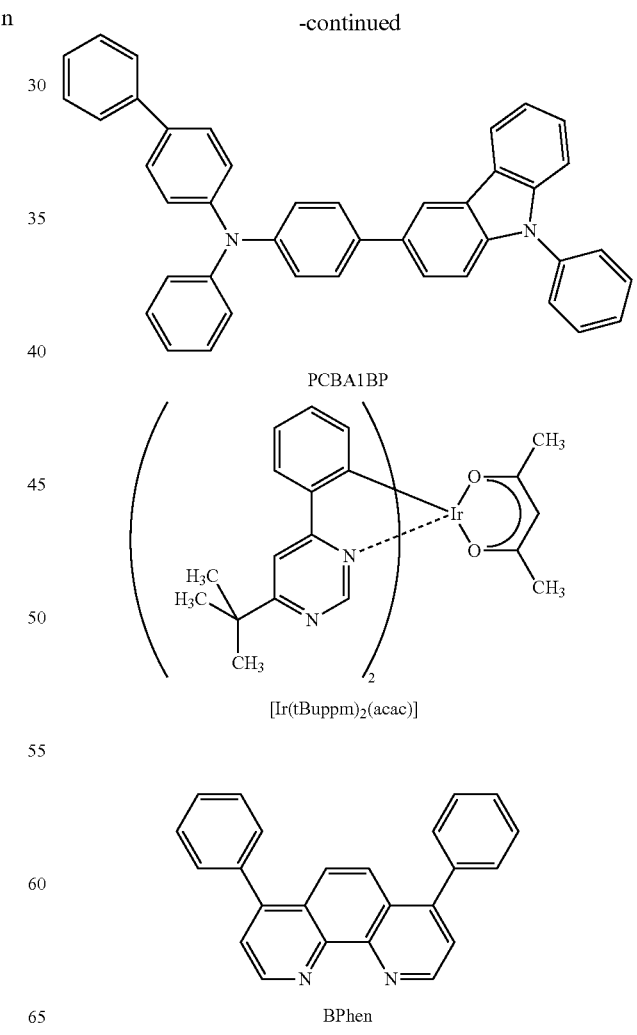

PCBA1BP

[Ir(tBuppm)$_2$(acac)]

BPhen (Fabrication of the Light-Emitting Element 1)

Next, fabrication of the light-emitting element 1 is described.

First, a light-transmitting conductive film was formed over the glass substrate 1500 by a sputtering method. In this example, an indium tin oxide film containing silicon (abbreviation: ITSO film) was formed to a thickness of 110 nm.

A partition having openings was formed over the light-transmitting conductive film such that the area of the first electrode was 2 mm square.

Next, the glass substrate 1500 was fixed to a substrate holder provided in a vacuum evaporation apparatus such that the side on which the first electrode was formed faced downward, and the pressure of the vacuum evaporation apparatus was reduced to approximately $10^{-4}$ Pa.

Next, the hole-injection layer 1511 was formed over the first electrode. The hole-injection layer 1511 was formed using a layer containing a composite material of an organic compound and an inorganic compound by co-evaporation of 1,3,5-tri(dibenzothiophen-4-yl)-benzene (abbreviation: DBT3P-II) and molybdenum(VI) oxide. The thickness of the layer containing a composite material was 40 nm, and the weight ratio of DBT3P-II and molybdenum oxide was adjusted to 2:1 (=DBT3P-II:molybdenum oxide). Note that the co-evaporation method refers to an evaporation method in which evaporation of a plurality of materials is performed using a plurality of evaporation sources at the same time in one treatment chamber.

Next, the hole-transport layer 1512 was formed over the hole-injection layer 1511. The hole-transport layer 1512 was formed using BPAFLP with a thickness of 20 nm by an evaporation method using resistance heating.

Next, the light-emitting layer 1513 was formed over the hole-transport layer 1512. The light-emitting layer 1513 was formed by co-evaporation of 2-[3-(dibenzothiophen-4-yl)phenyl]dibenzo[f,h]quinoxaline (abbreviation: 2mDBTP-DBq-II), 4-phenyl-4'-(9-phenyl-9H-carbazol-3-yl)triphenylamine (abbreviation: PCBA1BP), and Ir(nbppm)$_2$(acac) (endo- and exo-mixture). The thickness of the light-emitting layer 1513 was 40 nm, and the evaporation rate was adjusted so that the weight ratio of 2mDBTPDBq-II to PCBA1BP and Ir(nbppm)$_2$(acac) was 0.8:0.2:0.05 (=2mDBTPDBq-II:PCBA1BP:Ir(nbppm)$_2$(acac)).

Next, the electron-transport layer was formed over the light-emitting layer 1513. The electron-transport layer includes the first electron-transport layer 1514a and the second electron-transport layer 1514b. The first electron-transport layer 1514a was formed using 2mDBTPDBq-II with a thickness of 10 nm, and the second electron-transport layer 1514b was formed using BPhen with a thickness of 20 nm over the first electron-transport layer 1514a.

Then, the electron-injection layer 1515 was formed over the second electron-transport layer 1514b. The electron-injection layer 1515 was formed by evaporation of LiF, and the thickness thereof was 1 nm.

Lastly, the second electrode 1502 was formed over the electron-injection layer 1515. The second electrode 1502 was formed using aluminum (Al) with a thickness of 20 nm by an evaporation method using resistance heating.

Sealing was performed in a glove box under a nitrogen atmosphere so that the formed light-emitting element 1 was not exposed to the air.

Then, operating characteristics of the light-emitting element 1 were evaluated. Note that the evaluation was carried out at room temperature (in an atmosphere kept at 25° C.).

(Fabrication of the Light-Emitting Element 2)

Next, fabrication of the light-emitting element 2 is described.

The light-emitting element 2 was fabricated using the same materials and methods under the same conditions as the above-described light-emitting element 1 except for the concentration of the light-emitting organic compound used for the light-emitting layer 1513. Therefore, details of fabrication of the same components are referred to those of light-emitting element 1, and only the fabrication of the light-emitting layer 1513 which is a different component is described below.

The light-emitting layer 1513 of the light-emitting element 2 was formed by co-evaporation of 2mDBTPDBq-II, PCBA1BP, and Ir(nbppm)$_2$(acac). The thickness of the light-emitting layer 1513 was 40 nm, and the evaporation rate was adjusted so that the weight ratio of 2mDBTPDBq-II to PCBA1BP and Ir(nbppm)$_2$(acac) was 0.8:0.2:0.01 (=2mDBTPDBq-II:PCBA1BP:Ir(nbppm)$_2$(acac)).

Operating characteristics of the light-emitting element 2 were evaluated. Note that the evaluation was carried out at room temperature (in an atmosphere kept at 25° C.).

(Fabrication of the Light-Emitting Element 3)

Next, fabrication of the light-emitting element 3 is described.

The light-emitting element 3 was fabricated using the same materials and methods under the same conditions as the above-described light-emitting element 1 except that the light-emitting layer 1513 is a two-layered body formed using a different type of the light-emitting organic compound at a different concentration. Therefore, details of fabrication of the same components are referred to those of light-emitting element 1, and only the fabrication of the light-emitting layer 1513 which is a different component is described below.

The light-emitting layer 1513 of the light-emitting element 3 includes the first light-emitting layer 1513a and the second light-emitting layer 1513b each of which was formed by co-evaporation of 2mDBTPDBq-II, PCBA1BP, and (acetylacetonato)bis[5-methyl-4-(2-norbornyl)-6-phenylpyrimidinato](endo- and exo-mixture) (abbreviation: Ir(nbmppm)$_2$(acac)). The thickness of the light-emitting layer 1513 was 20 nm. Note that for the first light-emitting layer 1513a, the evaporation rate was adjusted so that the weight ratio of 2mDBTPDBq-II to PCBA1BP and Ir(nbmppm)$_2$(acac) was 0.8:0.2:0.05 (=2mDBTPDBq-II:PCBA1BP:Ir(nbmppm)$_2$(acac)). For the second light-emitting layer 1513b, the evaporation rate was adjusted so that the weight ratio of 2mDBT-PDBq-II to PCBA1BP and Ir(nbmppm)$_2$(acac) was 0.8:0.2:0.01 (=2mDBTPDBq-II:PCBA1BP:Ir(nbmppm)$_2$(acac)).

Operating characteristics of the light-emitting element 3 were evaluated. Note that the evaluation was carried out at room temperature (in an atmosphere kept at 25° C.).

(Fabrication of the Comparative Element)

Next, fabrication of the comparative element is described.

The comparative element was fabricated using the same materials and methods under the same conditions as the above-described light-emitting element 1 except for the light-emitting organic compound used for the light-emitting layer 1513. Therefore, details of fabrication of the same components are referred to those of light-emitting element 1, and only the fabrication of the light-emitting layer 1513 which is a different component is described below.

The light-emitting layer 1513 of the comparative element was formed by co-evaporation of 2mDBTPDBq-II, PCBA1BP, and (acetylacetonato)bis(6-tert-butyl-4-phenylpyrimidinato)iridium(III) (abbreviation: Ir(tBuppm)$_2$(acac)). The thickness of the light-emitting layer was 40 nm, and the evaporation rate was adjusted so that the weight ratio of 2mDBTPDBq-II to PCBA1BP and Ir(tBuppm)$_2$(acac) was 0.8:0.2:0.05 (=2mDBTPDBq-II:PCBA1BP:Ir(tBuppm)$_2$(acac)).

Operating characteristics of the comparative element were evaluated. Note that the evaluation was carried out at room temperature (in an atmosphere kept at 25° C.).

(Evaluation Results)

Figure 9:
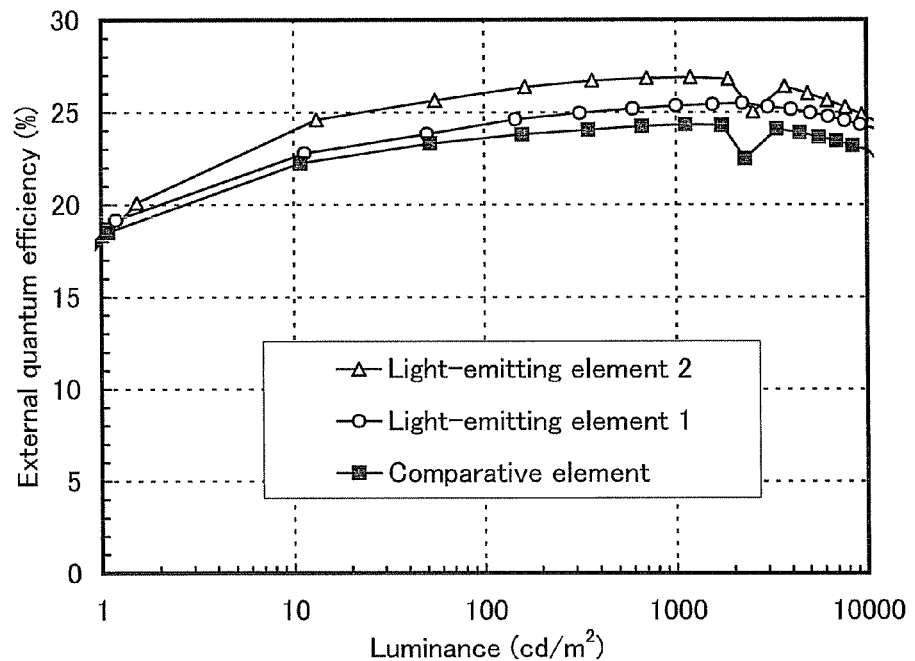
FIG. 9 shows external quantum efficiency vs. luminance characteristics of light-emitting elements according to an example.
Figure 10:
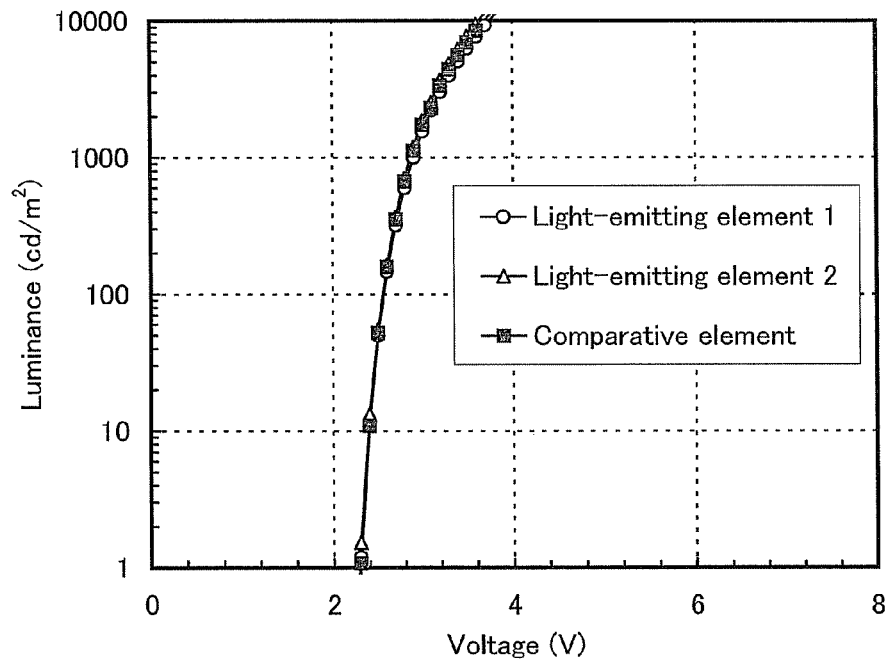
FIG. 10 shows luminance vs. voltage characteristics of light-emitting elements according to an example.
Figure 11:
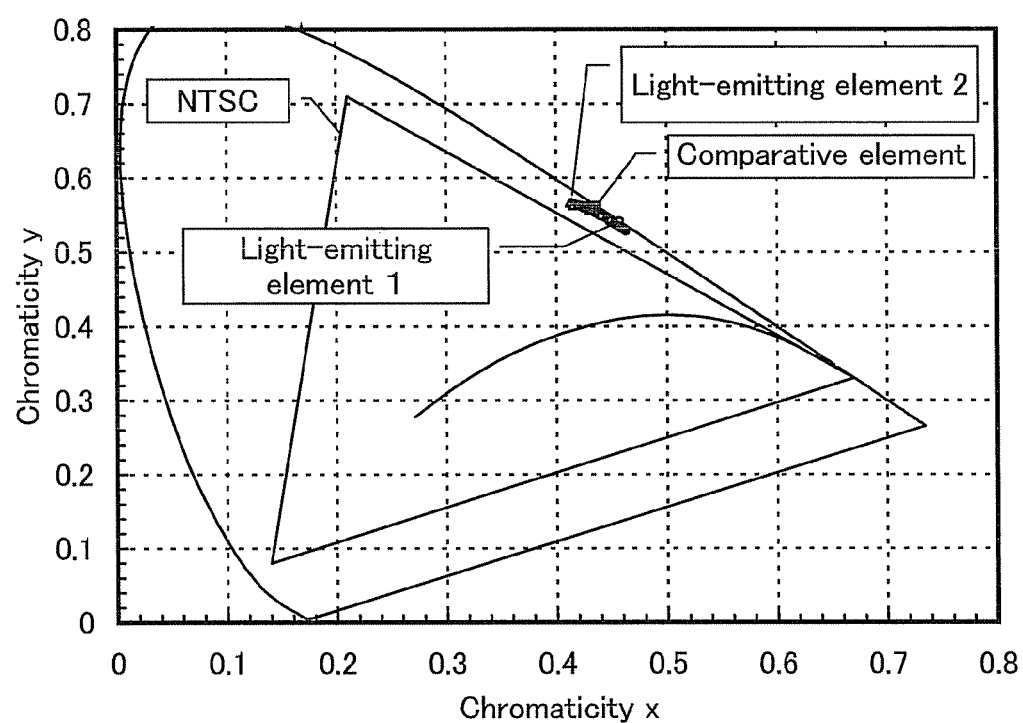
FIG. 11 shows chromaticity diagrams for describing light emitted from light-emitting elements according to an example.

FIG. 9, FIG. 10, and FIG. 11 respectively show external quantum efficiency vs. luminance characteristics, luminance vs. voltage characteristics, and chromaticities of the light-emitting elements 1 and 2 and the comparative element.

The CIE chromaticity coordinates of the light-emitting element 1 at a luminance of 1000 cd/m$^2$ were (x=0.46, y=0.53), and yellow-green light was emitted. Further, the external quantum efficiency, voltage, and current density at a luminance of 1000 cd/m$^2$ were 26.6%, 2.9 V, and 1.2 in A/cm$^2$, respectively.

The CIE chromaticity coordinates of the light-emitting element 2 at a luminance of 1200 cd/m$^2$ were (x=0.43, y=0.56), and green light was emitted. Further, the external quantum efficiency, voltage, and current density at a luminance of 1200 cd/m$^2$ were 26.9%, 2.9 V, and 1.2 mA/cm$^2$, respectively.

Figure 14:
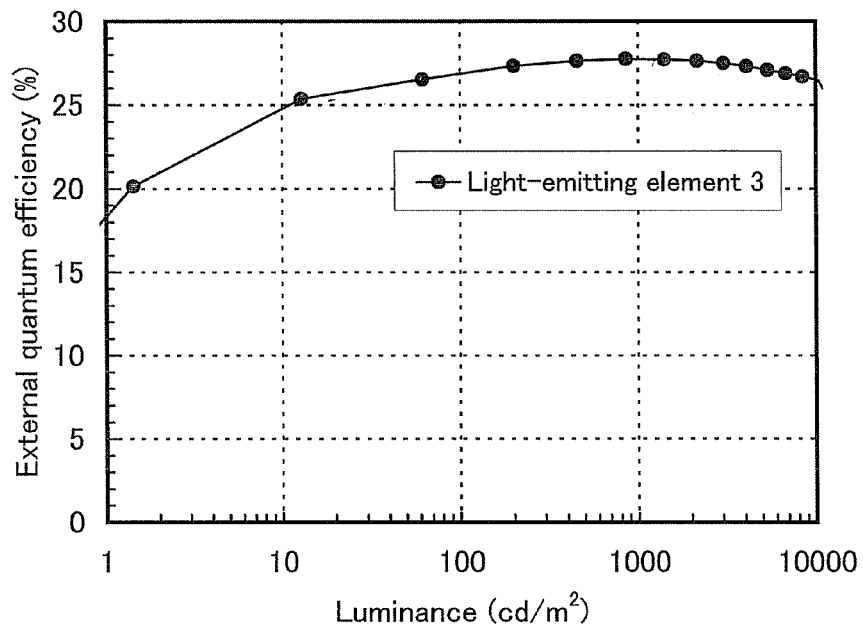
FIG. 14 shows external quantum efficiency vs. luminance characteristics of a light-emitting element according to an example.
Figure 15:
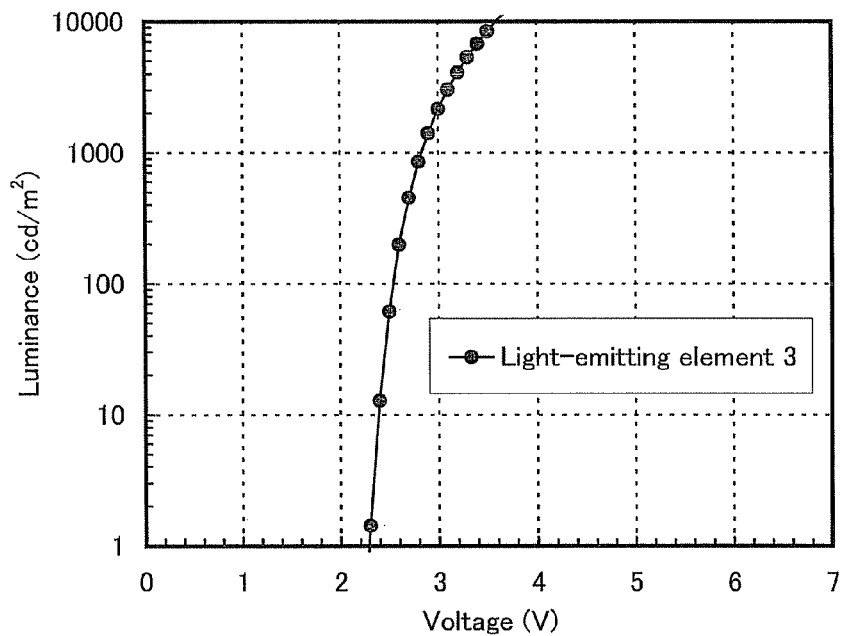
FIG. 15 shows luminance vs. voltage characteristics of a light-emitting element according to an example.
Figure 16:
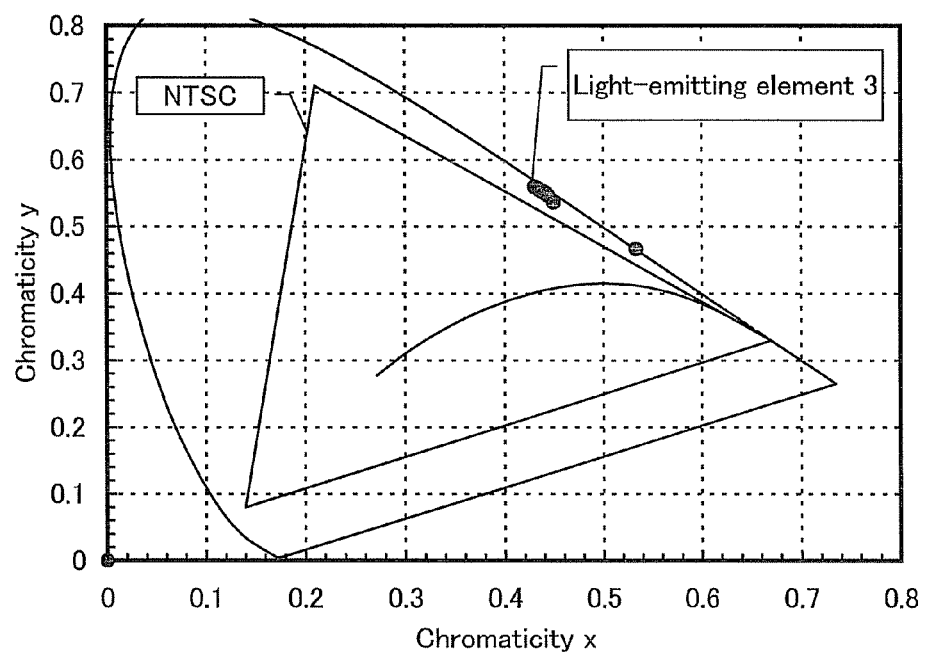
FIG. 16 shows a chromaticity diagram for describing light emitted from a light-emitting element according to an example.

FIG. 14, FIG. 15, and FIG. 16 respectively show external quantum efficiency vs. luminance characteristics, luminance vs. voltage characteristics, and the chromaticity of the light-emitting element 3.

The CIE chromaticity coordinates of the light-emitting element 3 at a luminance of 855 cd/m$^2$ were (x=0.44, y=0.55), and green light was emitted. Further, the external quantum efficiency, voltage, and current density at a luminance of 855 cd/m$^2$ were 27.8%, 2.8 V, and 0.86 mA/cm$^2$, respectively.

The CIE chromaticity coordinates of the comparative element at a luminance of 1120 cd/m$^2$ were (x=0.44, y=0.55), and green light was emitted. Further, the external quantum efficiency, voltage, and current density at a luminance of 1120 cd/m$^2$ were 24.3%, 2.9 V, and 1.28 mA/cm$^2$, respectively.

Reliability tests of the elements were conducted. In the reliability tests, changes in luminance over time were measured when the elements were driven under the conditions where the initial luminance was set to 5000 cd/m$^2$ and the current density was constant. Provided that the initial luminance was 100%, luminances of the light-emitting element 1, the light-emitting element 2, the light-emitting element 3, and the comparative element became lower than 90% after 33.7 hours, 35.5 hours, 20.1 hours, and 34.0 hours, respectively. Thus, each element has favorable reliability.

Each element fabricated in this example emitted light with extremely high external quantum efficiency. In particular, it is indicated that each of the light-emitting elements 1 to 3 has higher emission efficiency than the comparative element. Further, it is indicated that each element can be driven at a low voltage and has high reliability.

As mentioned above, the light-emitting element in which a phosphorescent organometallic complex according to an embodiment of the invention is applied to an EL layer provided between a pair of electrodes has high emission efficiency.

The following shows reasons of the above effects. The tricyclo[5.2.1.0(2,6)]decanyl group, the norbornyl group, or the adamantyl group, which is bonded to a ligand of a metal, does not cause the prolongation of the emission wavelength owing to the resonance effect and donates an electron to the ligand owing to the inductive effect. A phosphorescent organometallic complex including a ligand to which an electron is donated has a high molecular absorption coefficient; thus, when it is dispersed in a host material, energy can be received from the host material efficiently.

Alternatively, with the use of a phosphorescent organometallic complex including a ligand which has a tricyclo[5.2.1.0(2,6)]decanyl group, the norbornyl group, and the adamantyl group is bonded as a bulky substituent, concentration quenching is unlikely to occur because the increase in intermolecular distance inhibits the aggregation.

EXAMPLE 2

This example shows the synthesis of a phosphorescent organometallic complex according to an embodiment of the invention and results of evaluation of characteristics thereof Synthetic Example 1

This synthetic example specifically exemplifies a synthetic example of an organometallic complex Ir(nbppm)$_2$(acac) (endo- and exo-mixture) according to an embodiment of the invention, represented by the structural formula (100) in Embodiment 2. The structure of Ir(nbppm)$_2$(acac) is shown below.

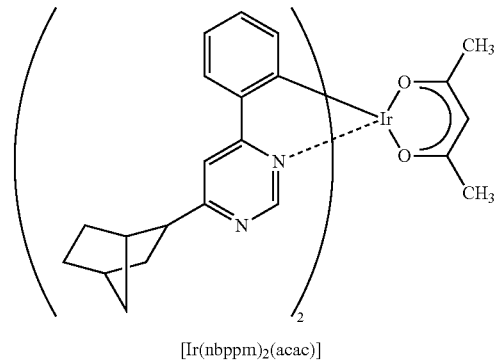

[Ir(nbppm)$_2$(acac)]

Step 1: Synthesis of 4-chloro-6phenylpyrimidine

Into a recovery flask equipped with a reflux pipe, 3.35 g of 4,6-dichloropyrimidine, 3.02 g of phenylboronic acid, 1.7 mL of tricyclohexylphosphine (abbreviation: PCy$_3$), 14.7 g of cesium carbonate, 0.31 g of tris(dibenzylideneacetone)dipalladium(0) (abbreviation: Pd$_2$(dba)$_3$), and 30 mL of dioxane were put, and the air in the flask was replaced by argon. This reaction container was heated by irradiation with microwaves (2.45 GHz, 120 W) for 60 minutes. The solvent of this reaction solution was distilled off, and then the obtained residue was purified by silica gel column chromatography using a mixed solvent of dichloromethane and hexane as a developing solvent in a volume ratio of 1:1, to give 4-chloro-6-phenylpyrimidine (light yellow powder, 34% in yield). Note that the irradiation with microwaves was performed using a microwave synthesis system (Discover, manufactured by CEM Corporation). The synthesis scheme of Step 1 is shown by (a-1).

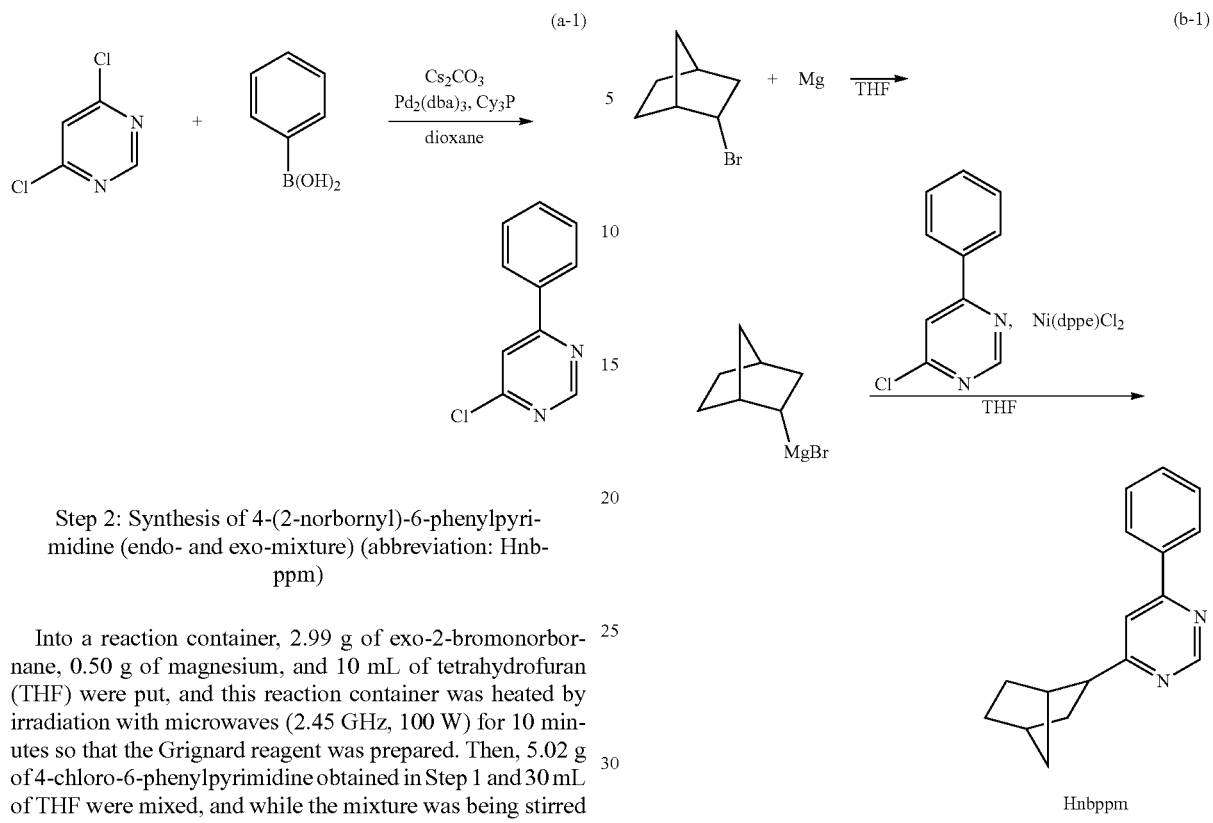

Step 2: Synthesis of 4-(2-norbornyl)-6-phenylpyrimidine (endo- and exo-mixture) (abbreviation: Hnbppm)

Into a reaction container, 2.99 g of exo-2-bromonorbornane, 0.50 g of magnesium, and 10 mL of tetrahydrofuran (THF) were put, and this reaction container was heated by irradiation with microwaves (2.45 GHz, 100 W) for 10 minutes so that the Grignard reagent was prepared. Then, 5.02 g of 4-chloro-6-phenylpyrimidine obtained in Step 1 and 30 mL of THF were mixed, and while the mixture was being stirred at −15° C., the obtained Grignard reagent was added thereto. Further, 30 mg of [1,2-bis(diphenylphosphino)ethane]nickel (II) dichloride (abbreviation: Ni(dppe)Cl$_2$) was also added, and the temperature of the mixture was increased to room temperature. An aqueous solution of ammonium chloride was added to this reaction solution, and an organic layer was extracted with ethyl acetate. The obtained organic layer was dried with magnesium sulfate. After the drying, the solution was filtered. The solvent of this solution was distilled off, and then the obtained residue was purified by flash column chromatography (silica gel) using a mixed solvent of hexane and ethyl acetate as a developing solvent in a volume ratio of 5:1, to give the objective pyrimidine derivative Hnbppm (yellow oily substance, 43% in yield). The synthesis scheme of Step 2 is shown by (b-1).

Step 3: Synthesis of di-μ-chloro-bis{bis[4-(2-norbornyl)-6-phenylpyrimidinato]iridium(III)} (endo- and exo-mixture) (abbreviation: [Ir(nbppm)$_2$Cl]$_2$)

Into a recovery flask equipped with a reflux pipe, 15 mL of 2-ethoxyethanol, 5 mL of water, 0.83 g of Hnbppm obtained in Step 2, and 0.49 g of iridium chloride hydrate (IrCl$_3$.H$_2$O) were put, and the air in the flask was replaced by argon. Then, irradiation with microwaves (2.45 GHz, 100 W) was performed for 30 minutes. The reaction solution was filtered and the obtained residue was washed with ethanol to give the dinuclear complex [Ir(nbppm)$_2$Cl]$_2$ (brown powder, 74% in yield). The synthesis scheme of Step 3 is shown by (c-1).

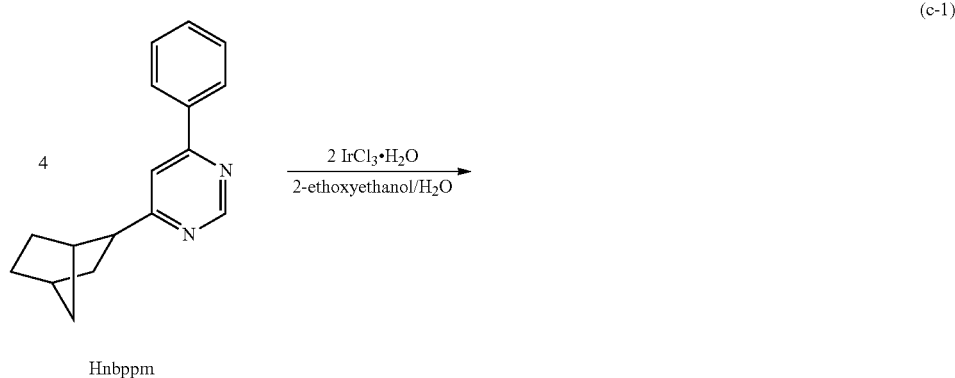

-continued

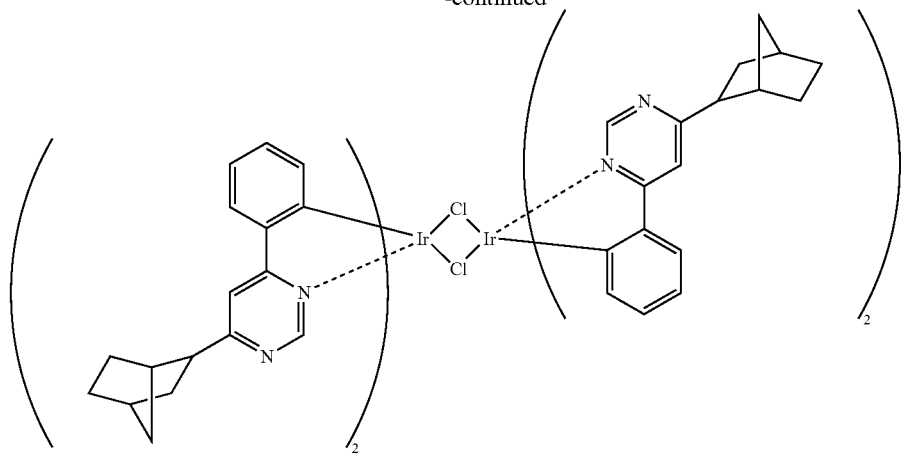

Step 4: Synthesis of Ir(nbppm)₂(acac) (endo- and exo-mixture)

In a recovery flask equipped with a reflux pipe were put 20 mL of 2-ethoxyethanol, 0.89 g of the dinuclear complex [Ir(nbppm)₂Cl]₂ obtained in Step 3, 0.19 mL of acetylacetone, and 0.65 g of sodium carbonate, and the air of the flask was replaced by argon. Then, irradiation with microwaves (2.45 GHz, 100 W) was performed for 30 minutes. The reaction solution was filtered and the obtained residue was washed with water, ethanol, and hexane. The residue was dissolved in dichloromethane, and filtered through a filter aid of Celite (produced by Wako Pure Chemical Industries, Ltd., Catalog No. 531-16855). The solvent of the filtrate was distilled off, and then the obtained residue was purified by flash column chromatography (silica gel) using a mixed solvent of dichloromethane and ethyl acetate as a developing solvent in a volume ratio of 50:1, to give the organometallic complex Ir(nbppm)₂(acac) according to an embodiment of the invention, as orange powder (54% in yield). The synthesis scheme of Step 4 is shown by (d-1).

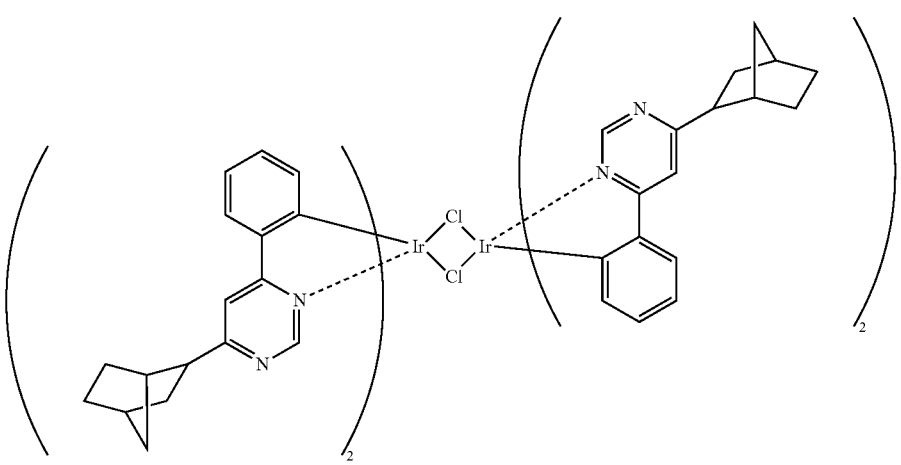

(d-1)

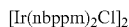

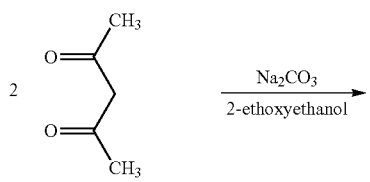
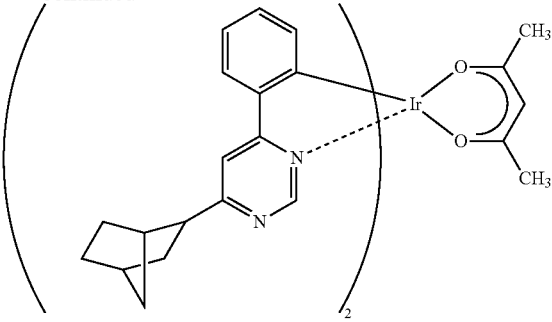

[Ir(nbppm)₂acac)]

Figure 12:
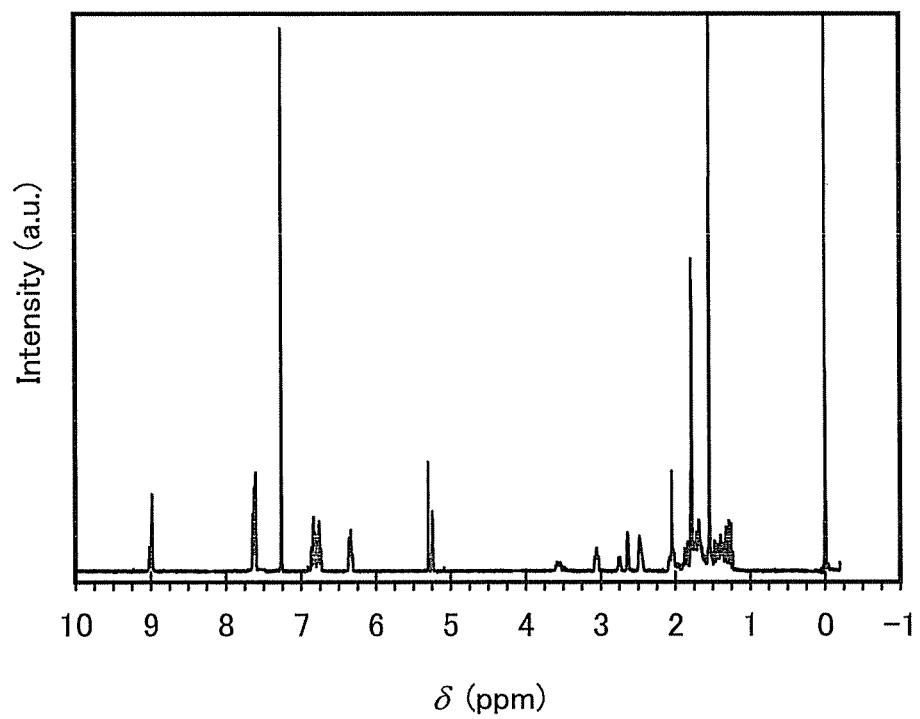
FIG. 12 shows a $^1$H-NMR chart of an organometallic complex represented by a structural formula (100).

An analysis result by nuclear magnetic resonance spectrometry (¹H-NMR) of the orange powder obtained in Step 4 is described below. FIG. 12 shows the ¹H-NMR chart. Note that in the obtained orange powder, endo-product signals and exo-product signals were mixed, and they were not able to be separated from each other in ¹H-NMR. Thus, the chemical shifts are described as a mixture thereof. This result revealed that the organometallic complex Ir(nbppm)₂(acac), represented by the above-described structural formula (100) according to an embodiment of the invention, was obtained in Synthetic Example 1.

¹H-NMR. δ (CDCl₃): 1.24-1.51, 1.61-2.06, 2.07, 2.48, 2.69, 3.03, 3.56, 5.24, 6.34, 6.74-6.86, 7.64, 8.99.

Figure 13:
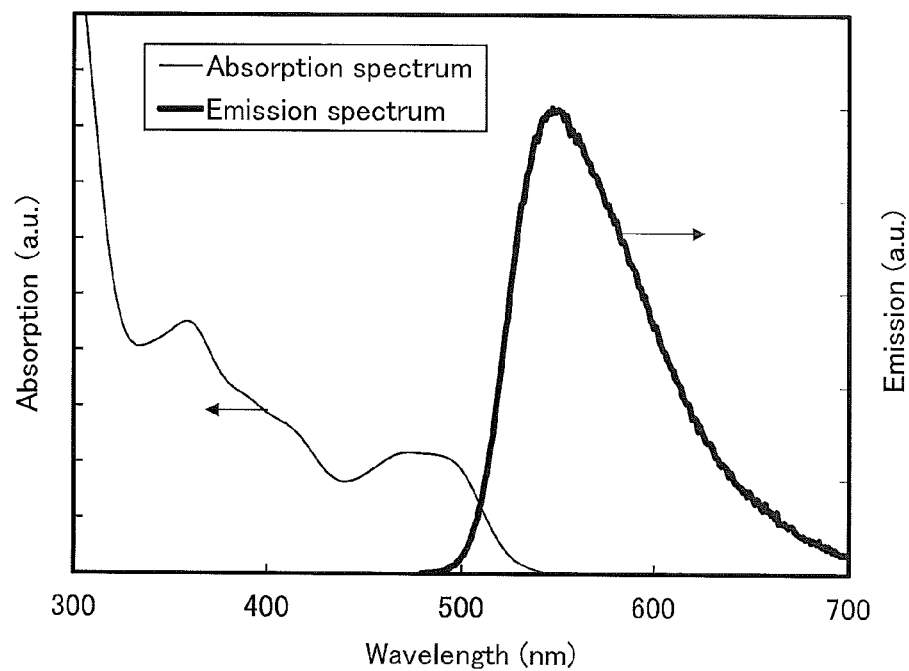
FIG. 13 shows an ultraviolet-visible absorption and emission spectra of the organometallic complex represented by the structural formula (100).

Next, an ultraviolet-visible absorption spectrum (hereinafter, simply referred to as absorption spectrum) and an emission spectrum of Ir(nbppm)₂(acac) in dichloromethane were measured. The absorption spectrum was measured with the use of an ultraviolet-visible light spectrophotometer (V-550, manufactured by JASCO Corporation) in the state where the dichloromethane solution (0.105 mmol/L) was put in a quartz cell at room temperature. The emission spectrum was measured with the use of a fluorescence spectrophotometer (FS920, manufactured by Hamamatsu Photonics Corporation) in the state where the degassed dichloromethane solution (0.105 mmol/L) was put in a quartz cell at room temperature. FIG. 13 shows the absorption spectrum and emission spectrum. In FIG. 13, the horizontal axis represents wavelength and the vertical axis represents absorption intensity and emission intensity. In FIG. 13, the thin line represents the absorption spectrum and the thick line represents the emission spectrum. Note that the absorption spectrum in FIG. 13 was obtained in such a way that an absorption spectrum measured by putting only dichloromethane in a quartz cell was subtracted from an absorption spectrum measured by putting the dichloromethane solution (0.105 mmol/L) in a quartz cell.

As shown in FIG. 13, the organometallic complex Ir(nbppm)₂(acac) according to an embodiment of the invention has an emission peak at 547 nm, and yellow green light was observed from the dichloromethane solution.

Synthetic Example 2

This synthetic example specifically exemplifies a synthetic example of an organometallic complex tris[4-(2-norbornyl)-6-phenylpyrimidinato]iridium(III) (endo- and exo-mixture) (abbreviation: Ir(nbppm)₃), represented by the structural formula (108) in Embodiment 2 according to an embodiment of the invention. The structure of Ir(nbppm)₃ is shown below.

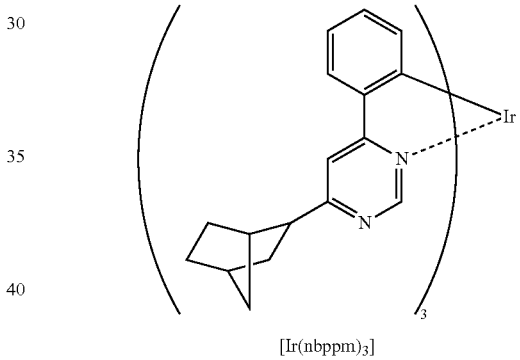

[Ir(nbppm)₃]

Synthesis of tris[4-(2-norbornyl)-6-phenylpyrimidinato]iridium(III) (endo- and exo-mixture) (abbreviation: Ir(nbppm)₃)

Into a recovery flask equipped with a reflux pipe, 1.24 g of the dinuclear complex [Ir(nbppm)₂Cl]₂, 0.53 g of 4-(2-norbornyl)-6-phenylpyrimidine (abbreviation: Hnbppm), 1.18 g of potassium carbonate, and 10 g of phenol were put, and the air in the flask was replaced by argon. Then, irradiation with microwaves (2.45 GHz, 100 W) was performed for 30 minutes. Methanol was added, and filtration was performed. The obtained residue was washed with water and then with methanol. The residue was dissolved in dichloromethane, and purification was performed by flash column chromatography (silica gel) using dichloromethane as a developing solvent, to give the organometallic complex Ir(nbppm)₃ according to an embodiment of the invention, as yellow powder (36% in yield). The synthesis scheme of this step is shown by (d-2).

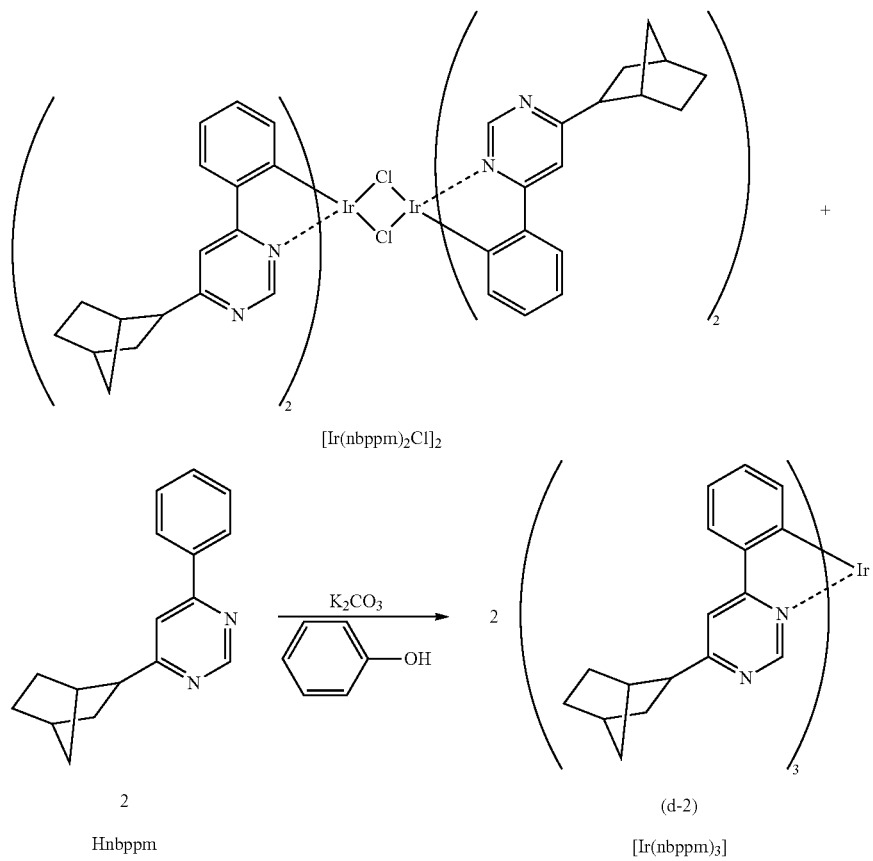

Figure 17:
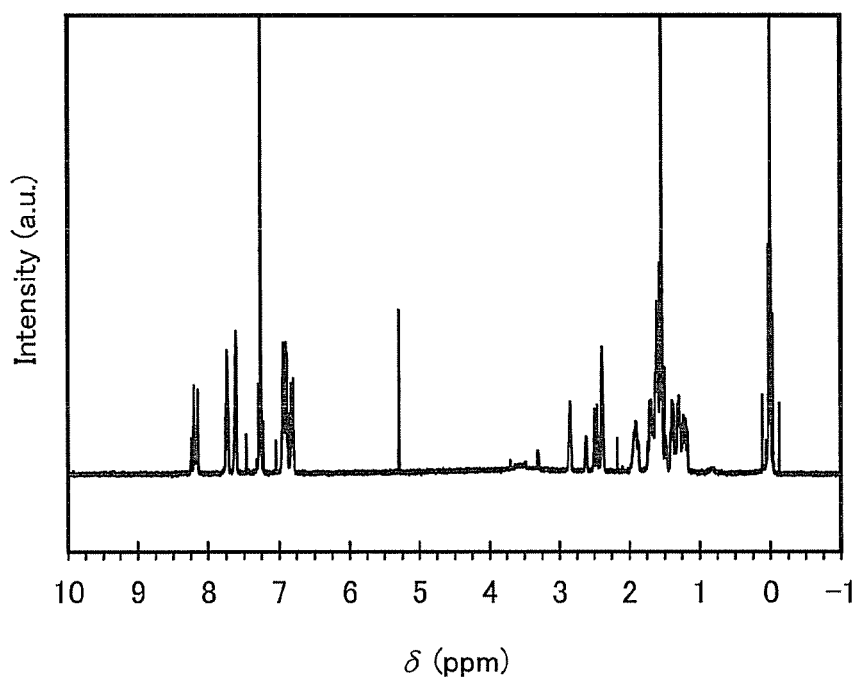
FIG. 17 shows a $^1$H-NMR chart of an organometallic complex represented by a structural formula (108).

An analysis result by nuclear magnetic resonance spectrometry ($^1$H-NMR) of the yellow powder obtained in the above step is described below. FIG. 17 shows the $^1$H-NMR chart. Note that in the obtained yellow powder, endo-product signals and exo-product signals were mixed, and they were not able to be separated from each other in $^1$H-NMR. The chemical shifts are described as a mixture thereof. This result revealed that the organometallic complex Ir(nbppm)$_3$, represented by the above-described structural formula (108) according to an embodiment of the invention, was obtained in Synthetic Example 2.

$^1$H-NMR. δ (CDCl$_3$): 1.18-1.72, 1.86-1.96, 2.38-2.50, 2.61, 2.84, 3.31, 6.78-6.85, 6.87-6.96, 7.61, 7.74, 8.14-8.24.

Figure 18:
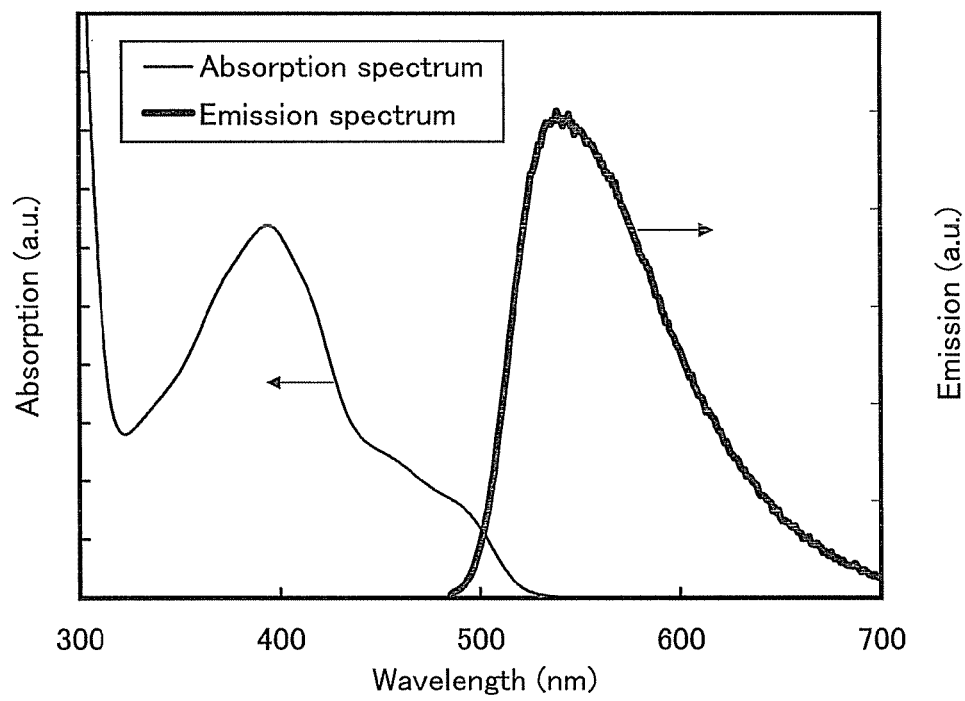
FIG. 18 shows an ultraviolet-visible absorption spectrum and emission spectrum of the organometallic complex represented by the structural formula (108).

Next, an absorption spectrum and an emission spectrum of Ir(nbppm)$_3$ in dichloromethane were measured. The measurements were carried out with the same apparatus and method under the same conditions to those of the case of Ir(nbppm)$_2$(acac). The sample concentration was, however, 0.085 mmol/L. FIG. 18 shows the absorption spectrum and emission spectrum. In. FIG. 18, the horizontal axis represents wavelength and the vertical axis represents absorption intensity and emission intensity. In FIG. 18, the thin line represents the absorption spectrum and the thick line represents the emission spectrum.

As shown in FIG. 18, the organometallic complex Ir(nbppm)$_3$ according to an embodiment of the invention has an emission peak at 541 nm, and yellow green light was observed from the dichloromethane solution.

The phosphorescence quantum yield (Φ) of Ir(nbppm)$_3$ was measured in the degassed toluene solution. The phosphorescence quantum yield was measured with the use of an absolute quantum yield measurement system (C9920-02, manufactured by Hamamatsu Photonics Corporation) at room temperature. The concentration of Ir(nbppm)$_3$ was 0.01 mmol/L. The phosphorescence quantum yield (Φ) of Ir(nbppm)$_3$ was 0.76. This result shows that Ir(nbppm)$_3$ is a material emitting phosphorescence with high efficiency in solution.

Note that a pyrimidine ring coordinating to iridium of the organometallic complex Ir(nbppm)$_3$ according to an embodiment of the invention has a norbornyl group as a substituent R$^1$; however, an organometallic complex Ir(tBuppm)$_3$ where a tertiary butyl group is included in the substituent R$^1$ instead of the norbornyl group has a phosphorescence quantum yield of 0.61.

When the substituent R$^1$ is a norbornyl group, electrons are more strongly donated to the pyrimidine ring coordinating to iridium owing to the inductive effect. As a result, the organometallic complex Ir(nbppm)$_3$ according to an embodiment of the invention emits phosphorescence with high efficiency.

Synthetic Example 3

This synthetic example specifically exemplifies a synthetic example of an organometallic complex Ir(nbmppm)$_2$(acac) (endo- and exo-mixture), represented by the structural formula (III) in Embodiment 2 according to an embodiment of the invention. The structure of Ir(nbmppm)$_2$(acac) is shown below.

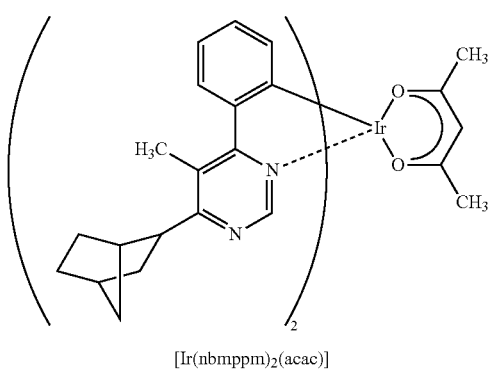

[Ir(nbmppm)₂(acac)]

Step 1: Synthesis of 4-chloro-5-methyl-6-phenylpyrimidine

Into a recovery flask equipped with a reflux pipe, 4.9 g of 4,6-dichloro-5-methylpyrimidine, 3.7 g of phenylboronic acid, 2.3 mL of PCy₃, 20 g of cesium carbonate, 0.41 g of Pd₂(dba)₃, and 40 mL of dioxane were put, and the air in the flask was replaced by argon. This reaction container was heated by irradiation with microwaves (2.45 GHz, 300 W) for 100 minutes. The solvent of this solution was distilled off, and then the obtained residue was purified by flash column chromatography (silica gel) using a mixed solvent of dichloromethane and hexane as a developing solvent in a volume ratio of 7:3, to give 4-chloro-5-methyl-6-phenylpyrimidine (yellow oily substance, 37% in yield). Note that the irradiation with microwaves was performed using a microwave synthesis system (MicroSYNTH, manufactured by Milestone General K.K.). The synthesis scheme of Step 1 is shown by (a-3).

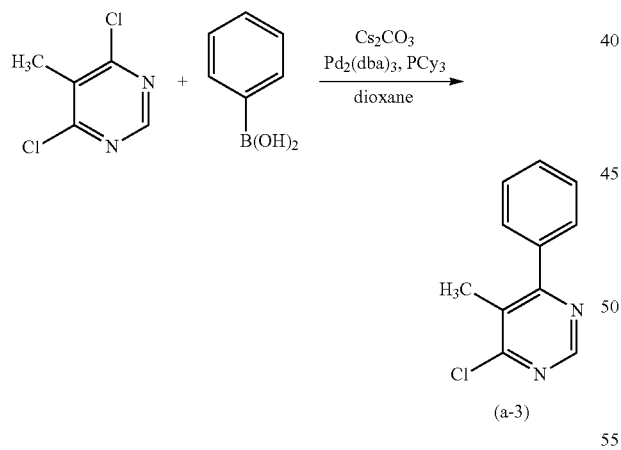

(a-3)

Step 2: Synthesis of 5-methyl-4-(2-norbornyl)-6-phenylpyrimidine (endo- and exo-mixture) (abbreviation: Hnbmppm)

Into a reaction container, 4.2 g of exo-2-bromonorbornane, 0.70 g of magnesium, and 12 mL of THF were put, and this reaction container was heated by irradiation with microwaves (2.45 GHz, 100 W) for 10 minutes so that the Grignard reagent was prepared. Then, 2.3 g of 4-chloro-5-methyl-6-phenylpyrimidine obtained in Step 1 and 20 mL of THF were mixed, and while the mixture was being stirred at −20° C., the obtained Grignard reagent was added thereto. Further, 40 mg of Ni(dppe)Cl₂ was also added, and the temperature of the mixture was increased to room temperature. An aqueous solution of ammonium chloride was added to this reaction solution, and an organic layer was extracted with ethyl acetate. The obtained organic layer was dried with magnesium sulfate. After the drying, the solution was filtered. The solvent of this solution was distilled off, and then the obtained residue was purified by flash column chromatography (silica gel) using a mixed solvent of dichloromethane and ethyl acetate as a developing solvent in a volume ratio of 9:1, to give the objective pyrimidine derivative Hnbmppm (yellow oily substance, 17% in yield). Note that the irradiation with microwaves was performed using a microwave synthesis system (Discover, manufactured by CEM Corporation). The synthesis scheme of Step 2 is shown by (b-3).

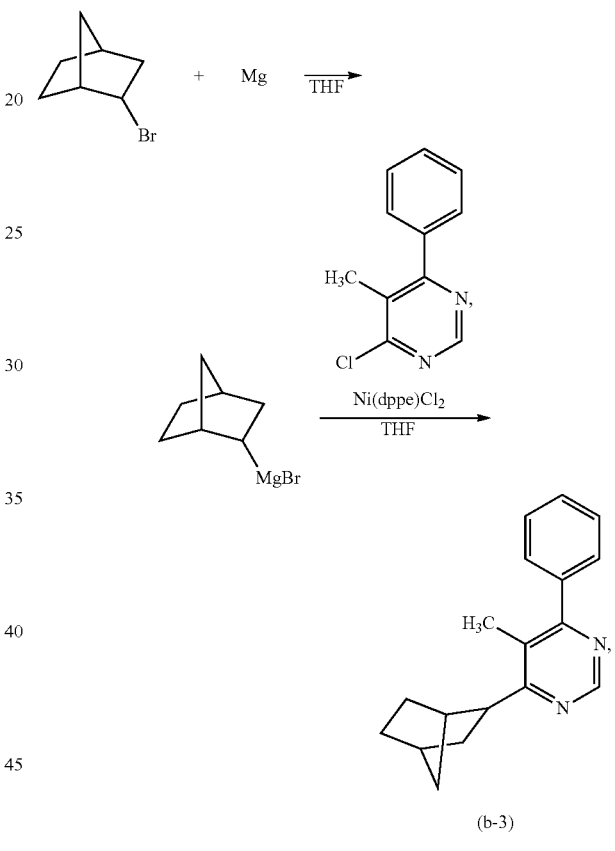

(b-3)

Hnbmppm

Step 3: Synthesis of di-μ-chloro-bis{bis[5-methyl-4-(2-norbornyl)-6-phenylpyrimidinato]iridium(II)} (endo- and exo-mixture) (abbreviation: [Ir(nbmppm)₂Cl]₂)

Into a recovery flask equipped with a reflux pipe, 15 mL of 2-ethoxyethanol, 5 mL of water, 0.5 g of Hnbmppm obtained in Step 2, and 0.28 g of iridium chloride hydrate (IrCl₃.H₂O) were put, and the air in the flask was replaced by argon. Then, irradiation with microwaves (2.45 GHz, 100 W) was performed for 30 minutes. The reaction solution was filtered and the obtained residue was washed with ethanol to give a dinuclear complex [Ir(nbmppm)₂Cl]₂ (yellow powder, 63% in yield). Note that the irradiation with microwaves was performed using a microwave synthesis system (Discover, manufactured by CEM Corporation). The synthesis scheme of Step 3 is shown by (c-3).

Step 4: Synthesis of Ir(nbmppm)₂(acac) (endo- and exo-mixture)

To a recovery flask equipped with a reflux pipe were added 20 mL of 2-ethoxyethanol, 0.45 g of the dinuclear complex [Ir(nbmppm)₂Cl]₂ obtained in Step 3, 0.093 mL of acetylacetone, and 0.32 g of sodium carbonate, and the air in the flask was replaced by argon. Then, irradiation with microwaves (2.45 GHz, 100 W) was performed for 30 minutes. The reaction solution was filtered and the obtained residue was washed with water, ethanol, and hexane, in that order. Then, purification was performed by flash column chromatography (silica gel) using dichloromethane as a developing solvent, to give the organometallic complex Ir(nbmppm)₂(acac) according to an embodiment of the invention, as yellow powder (40% in yield). Note that the irradiation with microwaves was performed using a microwave synthesis system (Discover, manufactured by CEM Corporation). The synthesis scheme of Step 4 is shown by (d-3).

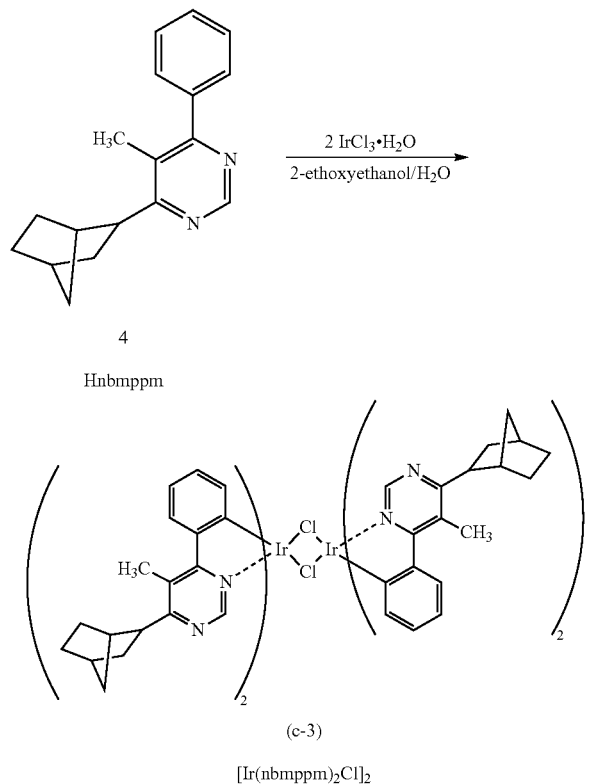

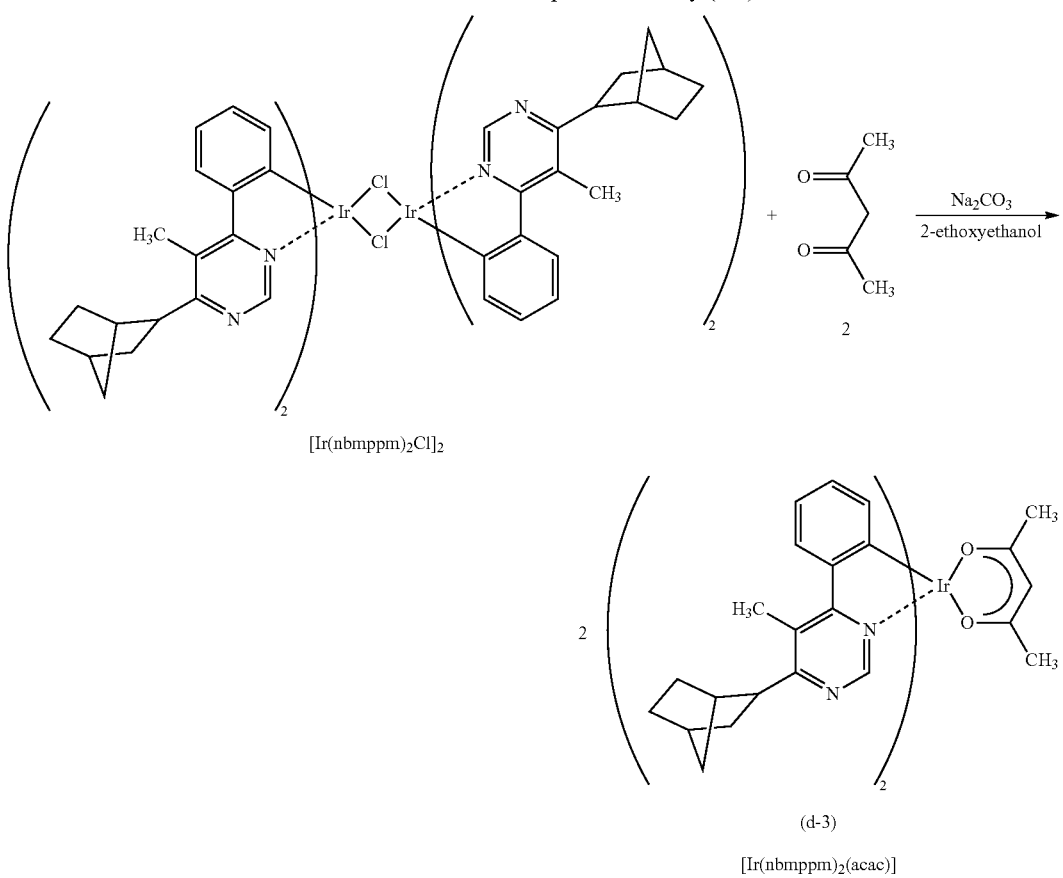

Figure 19:
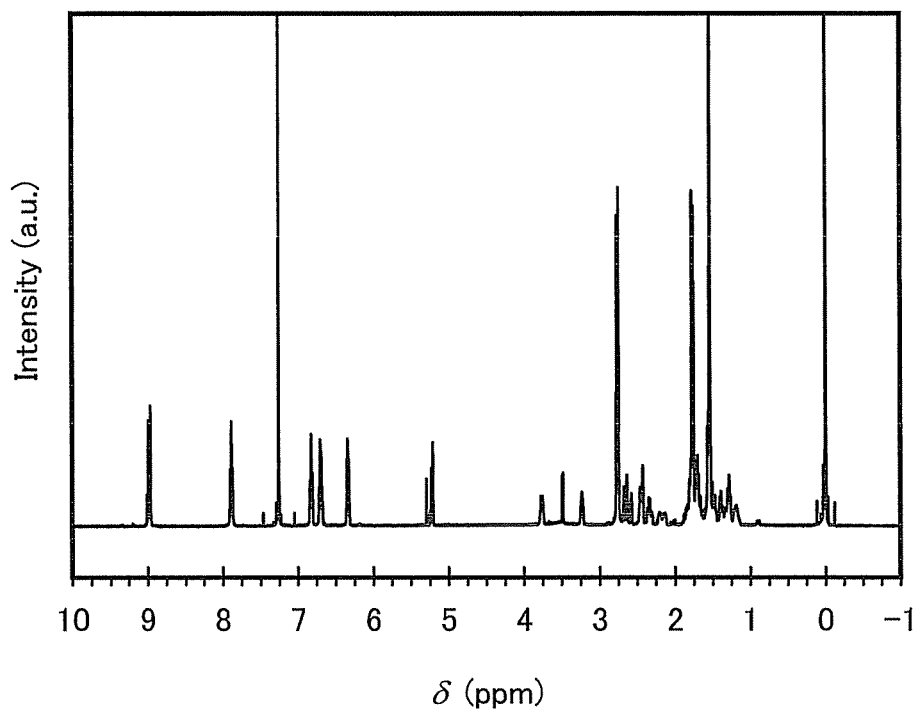
FIG. 19 is a $^1$H-NMR chart of an organometallic complex represented by a structural formula (111).

An analysis result by nuclear magnetic resonance spectrometry ($^1$H-NMR) of the yellow powder obtained in Step 4 is described below. FIG. 19 shows the $^1$H-NMR chart. Note that in the obtained yellow powder, endo-product signals and exo-product signals were mixed, and they were not able to be separated from each other in $^1$H-NMR. The chemical shifts are described as a mixture thereof. This result revealed that the organometallic complex Ir(nbmppm)$_2$(acac), represented by the above-described structural formula (III) according to an embodiment of the invention, was obtained in Synthetic Example 3.

$^1$H-NMR. δ (CDCl$_3$): 1.15-1.41, 1.47-1.51, 1.46-1.85, 2.14-2.68, 2.76, 3.23, 3.77, 5.21-5.25, 6.33-6.35, 6.70, 6.82, 7.87-7.90, 8.96-9.01.

Figure 20:
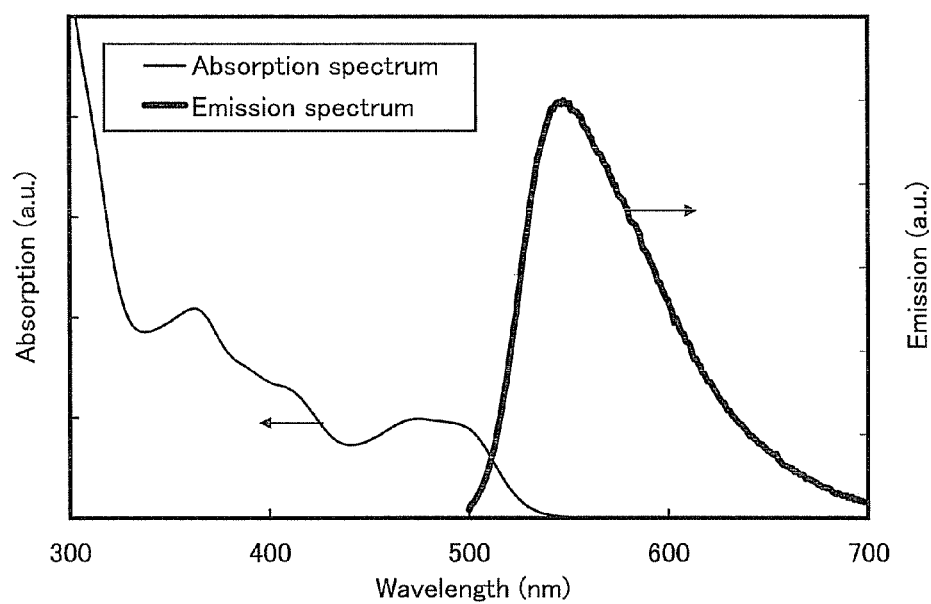
FIG. 20 shows an ultraviolet-visible absorption and emission spectra of the organometallic complex represented by the structural formula (111).

Next, an absorption spectrum and an emission spectrum of Ir(nbmppm)$_2$(acac) in dichloromethane were measured. The measurements were carried out with the same apparatus and method under the same conditions to those of the case of Ir(nbppm)$_2$(acac). The sample concentration was, however, 0.094 mmol/L. FIG. 20 shows the absorption spectrum and emission spectrum. In FIG. 20, the horizontal axis represents wavelength and the vertical axis represents absorption intensity and emission intensity. In FIG. 20, the thin line represents the absorption spectrum and the thick line represents the emission spectrum.

As shown in FIG. 20, the organometallic complex Ir(nbmppm)$_2$(acac) according to an embodiment of the invention has an emission peak at 547 nm, and yellow green light was observed from the dichloromethane solution.

Synthetic Example 4

This synthetic example specifically exemplifies a synthetic example of an organometallic complex (acetylacetonato)bis[4-(1-adamantyl)-6-phenylpyrimidinato]iridium(III) (abbreviation: Ir(Adm1ppm)$_2$(acac)), represented by the structural formula (128) in Embodiment 2 according to an embodiment of the invention. The structure of Ir(Adm1ppm)$_2$(acac) is shown below.

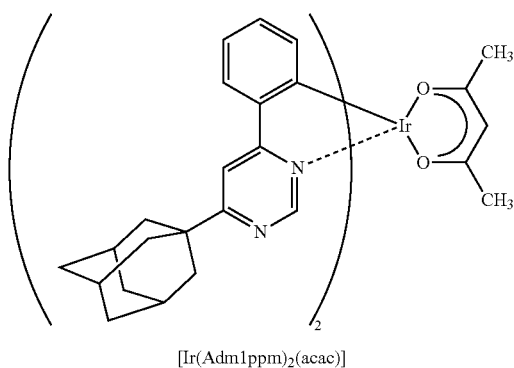

[Ir(Adm1ppm)$_2$(acac)]

Step 1: Synthesis of 1-(1-adamantyl)-3-phenyl-propane-1,3-dione

Into a flask equipped with a reflux pipe were put 14.50 g of acetophenone, 25.13 g of 1-adamantanecarboxylic acid ethyl, 22 g of tert-butoxysodium, and 60 mL of THF, and the air in the flask was replaced by nitrogen. This reaction container was heated at 80° C. for 7 hours and 30 minutes. Dilute hydrochloric acid was added to this reaction solution, and extraction was performed with toluene. The solvent of the obtained toluene solution was distilled off, and then the obtained residue was purified by flash column chromatography (silica gel) using a mixed solvent of dichloromethane and hexane as a developing solvent in a volume ratio of 9:1, to give 1-(1-adamantyl)-3-phenyl-propane-1,3-dione (colorless oily substance, 4% in yield). The synthesis scheme of Step 1 is shown by (a-4).

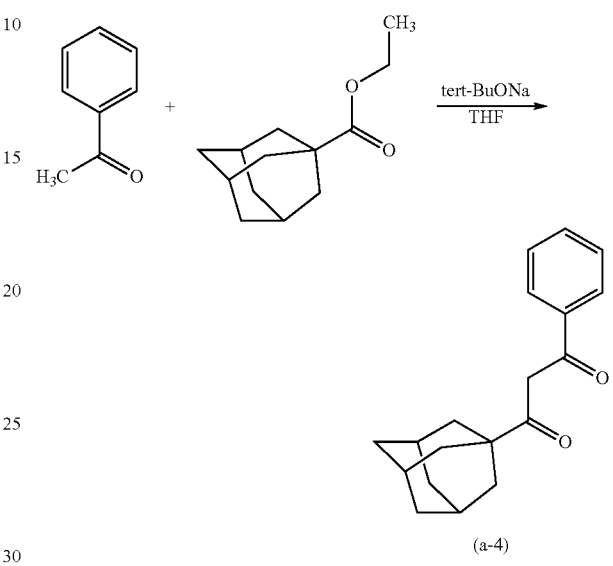

(a-4)

Step 2: Synthesis of 4-(1-adamantyl)-6-phenylpyrimidine (abbreviation: HAdm1ppm)

Then, 1-(1-adamantyl)-3-phenyl-propane-1,3-dione (1.39 g) obtained in Step 1 and 2.22 g of formamide were mixed, and the mixture was irradiated with microwaves (2.45 GHz, 300 W) at 220° C. for 15 minutes. This reaction solution was poured into a dilute aqueous solution of sodium hydroxide, and the organic layer was subjected to extraction with ethyl acetate. The obtained organic layer was dried with magnesium sulfate. After the drying, the solution was filtered. The solvent of this solution was distilled off, and then the obtained residue was purified by flash column chromatography (silica gel) using a mixed solvent of dichloromethane and ethyl acetate as a developing solvent in a volume ratio of 97:3, to give the objective pyrimidine derivative HAdm1ppm (reddish brown oily substance, 8% in yield). Note that the irradiation with microwaves was performed using a microwave synthesis system (MicroSYNTH, manufactured by Milestone General K.K.). The synthesis scheme of Step 2 is shown by (b-4).

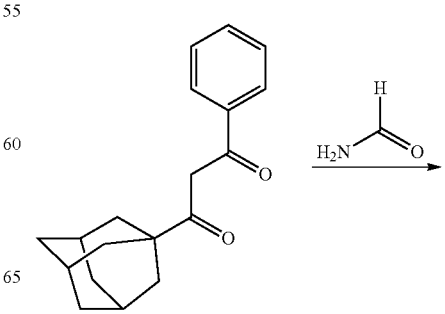

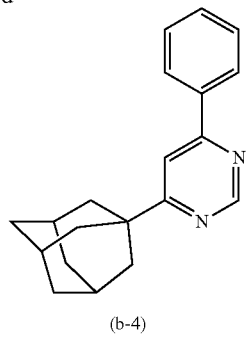

(b-4)

HAdm1ppm

Step 3: Synthesis of di-μ-chloro-bis{bis[4-(1-adamantyl)-6-phenylpyrimidinato]iridium(III)} (abbreviation: [Ir(Adm1ppm)₂Cl]₂)

In a recovery flask equipped with a reflux pipe were put 10 mL of 2-ethoxyethanol, 3 mL of water, 0.12 g of HAdm1ppm obtained in Step 2, and 0.062 g of iridium chloride hydrate (IrCl₃·H₂O), and the air in the flask was replaced by argon. After that, irradiation with microwaves (2.45 GHz, 100 W) was performed for 15 minutes. The reaction mixture was filtered and the obtained residue was washed with ethanol to give a dinuclear complex [Ir(Adm1ppm)₂Cl]₂ (yellow powder, 77% in yield). Note that the irradiation with microwaves was performed using a microwave synthesis system (Discover, manufactured by CEM Corporation). The synthesis scheme of Step 3 is shown by (c-4).

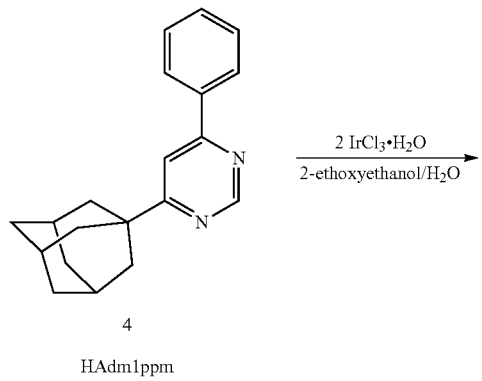

HAdm1ppm

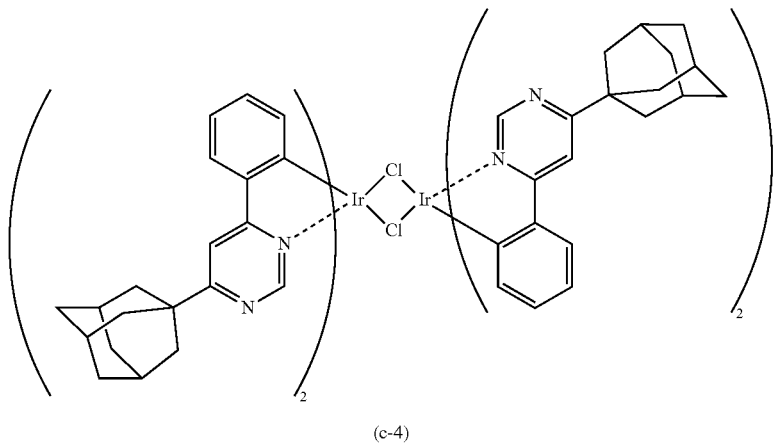

(c-4)

[Ir(Adm1ppm)₂Cl]₂

Step 4: Synthesis of Ir(Adm1ppm)₂(acac)

In a recovery flask equipped with a reflux pipe were put 20 mL of 2-ethoxyethanol, 0.13 g of the dinuclear complex [Ir(Adm1ppm)₂Cl]₂ obtained in Step 3, 0.025 mL of acetylacetone, and 0.085 g of sodium carbonate, and the air in the flask was replaced by argon. After that, irradiation with microwaves (2.45 GHz, 120 W) was performed for 15 minutes. The reaction mixture was filtered and the obtained residue was washed with water, ethanol, and hexane, in that order. Then, purification was performed by flash column chromatography (silica gel) using dichloromethane as a developing solvent, to give the organometallic complex Ir(Adm1ppm)₂(acac) according to an embodiment of the invention, as yellow powder (86% in yield). Note that the irradiation with microwaves was performed using a microwave synthesis system (Discover, manufactured by CEM Corporation). The synthesis scheme of Step 4 is shown by (d-4).

structural formula (128) according to an embodiment of the invention, was obtained in Synthetic Example 4.

¹H-NMR. δ (CDCl₃): 1.78 (s, 6H), 1.85 (s, 6H), 2.12 (s, 12H), 2.20 (s, 6H), 5.25 (s, 1H), 6.32 (d, 2H), 6.76 (t, 2H), 6.83 (t, 2H), 7.66 (m, 4H), 9.02 (s, 2H).

Figure 22:
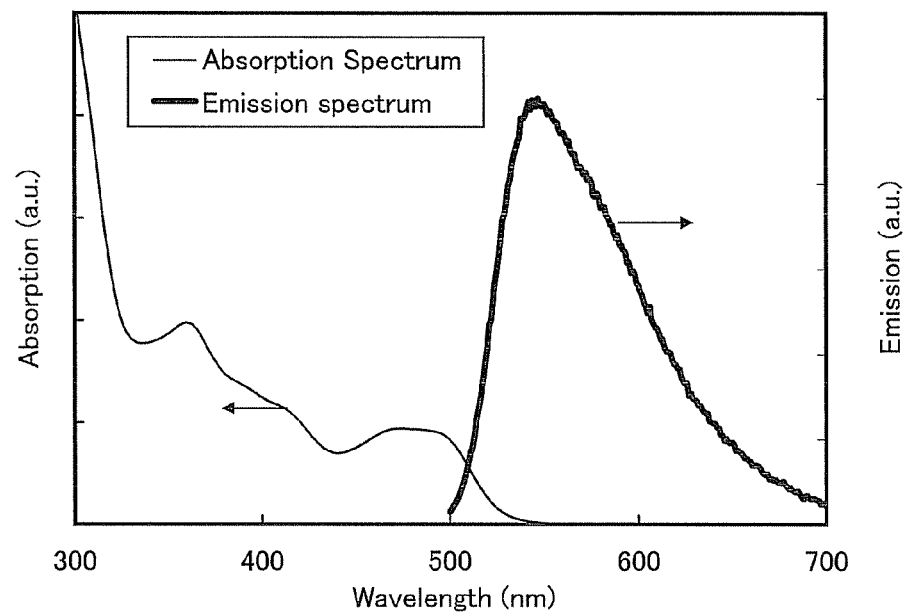
FIG. 22 shows an ultraviolet-visible absorption and emission spectra of the organometallic complex represented by the structural formula (128).

Next, an absorption spectrum and an emission spectrum of Ir(Adm1ppm)₂(acac) in dichloromethane were measured. The measurements were carried out with the same apparatus and method under the same conditions to those of the case of Ir(nbppm)₂(acac). The sample concentration was, however, 0.103 mmol/L. FIG. 22 shows the absorption spectrum and emission spectrum. In FIG. 22, the horizontal axis represents wavelength and the vertical axis represents absorption intensity and emission intensity. In FIG. 22, the thin line represents the absorption spectrum and the thick line represents the emission spectrum.

As shown in FIG. 22, the organometallic complex Ir(Adm1ppm)₂(acac) according to an embodiment of the invention has an emission peak at 543 nm, and yellow green light was observed from the dichloromethane solution.

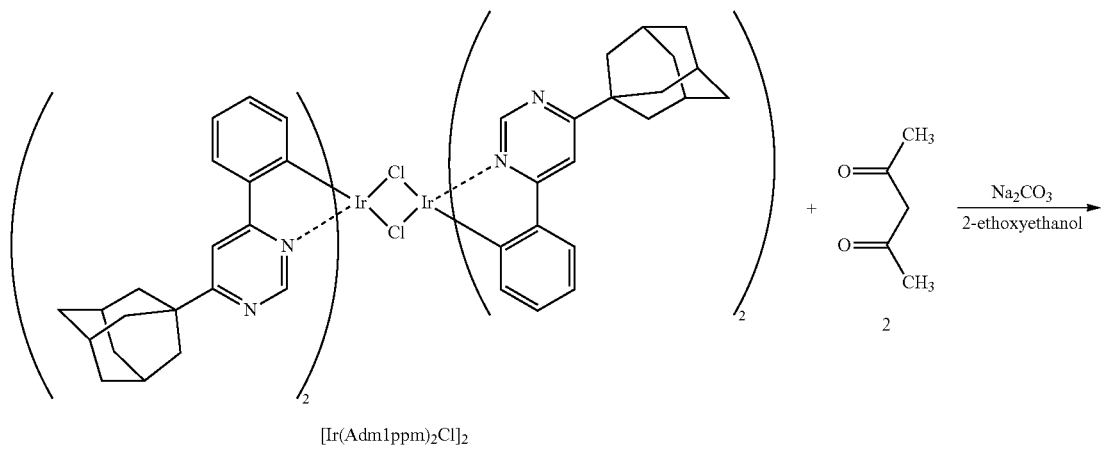

[Ir(Adm1ppm)₂Cl]₂

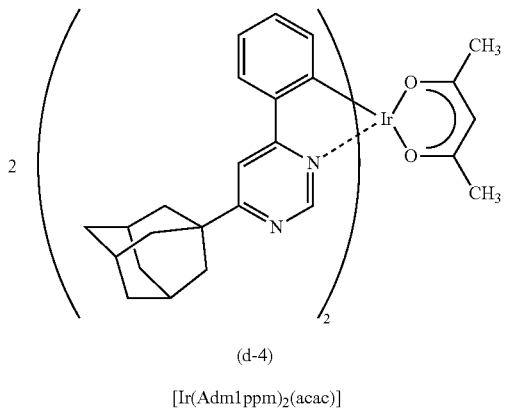

(d-4)

[Ir(Adm1ppm)₂(acac)]

Figure 21:
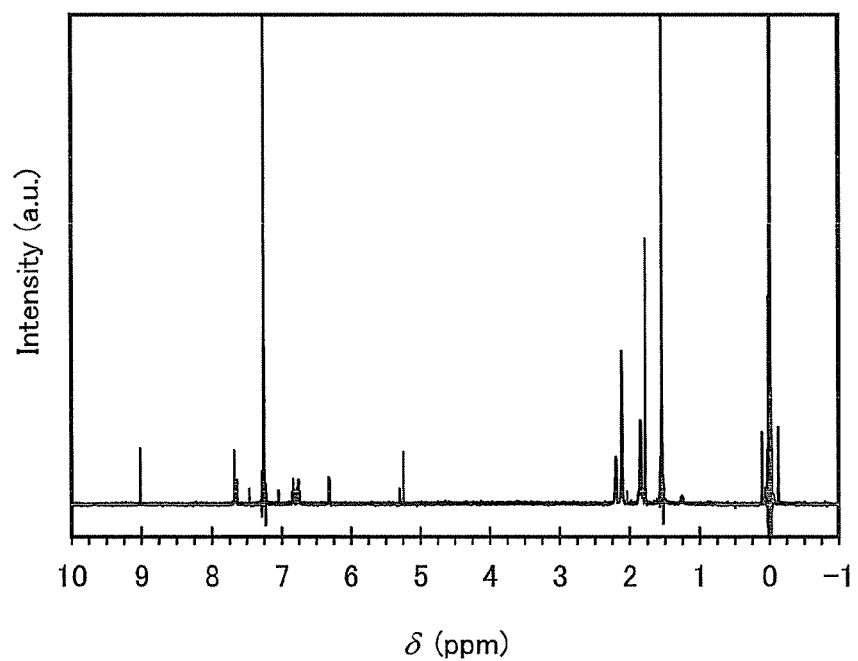
FIG. 21 is a $^1$H-NMR chart of an organometallic complex represented by a structural formula (128).

An analysis result by nuclear magnetic resonance spectrometry (¹H-NMR) of the yellow powder obtained in Step 4 is described below. FIG. 21 shows the ¹H-NMR chart. This result revealed that the organometallic complex Ir(Adm1ppm)₂(acac), represented by the above-described

Reference Example 1

The synthesis of BPAFLP used in the above Examples is specifically described. The structure of BPAFLP is shown below.

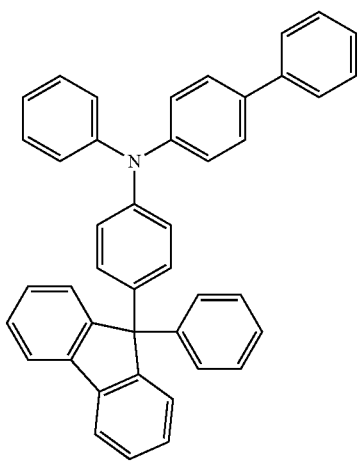

BPAFLP

Step 1: Synthesis of 9-(4-bromophenyl)-9-phenylfluorene

In a 100-mL three-neck flask, 12 g (50 mmol) of 2-bromobiphenyl dissolved in 10 mL of diethyl ether was slowly reacted with 1.2 g (50 mmol) of magnesium, which was followed by heating under reflux with stirring for 2.5 hours to form a Grignard reagent.

Into a 500-mL three-neck flask, 10 g (40 mmol) of 4-bromobenzophenone and 100 mL of diethyl ether were put. After the Grignard reagent which was synthesized in advance was slowly dropped into this mixture, the mixture was stirred and heated under reflux for 9 hours.

After the reaction, this mixture was filtered to give a residue. The residue was dissolved in 150 mL of ethyl acetate, 1N-hydrochloric acid was added to the mixture until the mixture was acidified, and the mixture was stirred for 2 hours. The organic layer of the mixture was washed with water, and then dried with magnesium sulfate. This suspension was filtered, and the obtained filtrate was concentrated to give a highly viscous substance.

Into a 500-mL recovery flask, this highly viscous substance, 50 mL of glacial acetic acid, and 1.0 mL of hydrochloric acid were put. The mixture was stirred and heated at 130° C. for 1.5 hours under a nitrogen atmosphere.

After the reaction, this reaction mixture was filtered to give a residue. The obtained residue was washed with water, an aqueous solution of sodium hydroxide, water, and methanol in that order, and then dried, so that 11 g of the objective white powder was obtained in a yield of 69%. The synthesis scheme (x-1) of Step 1 is shown below.

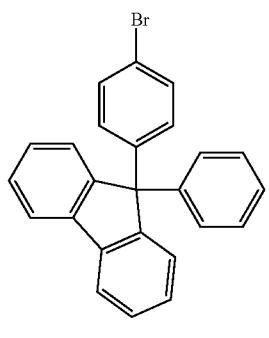

(x-1)

Step 2: Synthesis of BPAFLP

Into a 100-mL three-neck flask, 3.2 g (8.0 mmol) of 9-(4-bromophenyl)-9-phenylfluorene, 2.0 g (8.0 mmol) of 4-phenyl-diphenylamine, 1.0 g (10 mmol) of sodium tert-butoxide, and 23 mg (0.04 mmol) of bis(dibenzylideneacetone)palladium(0) were put, and the air in the three-neck flask was replaced by nitrogen. Then, 20 mL of dehydrated xylene was added to this mixture. After the mixture was deaerated while being stirred under reduced pressure, 0.2 mL (0.1 mmol) of tri(tert-butyl)phosphine (10 wt % hexane solution) was added thereto. This mixture was stirred and heated under a nitrogen atmosphere at 110° C. for 2 hours.

After the reaction, 200 mL of toluene was added to the reaction mixture, and the resulting suspension was filtered through Florisil (produced by Wako Pure Chemical Industries, Ltd., Catalog No. 540-00135) and Celite. The obtained filtrate was concentrated, and purification was performed by silica gel column chromatography (with a developing solvent of toluene and hexane in a 1:4 ratio). The obtained fraction was concentrated, and acetone and methanol were added to the mixture. The mixture was irradiated with ultrasonic waves and then allowed to precipitate 4.1 g of the objective white powder in a yield of 92%. The synthesis scheme (x-2) of Step 2 is shown below.

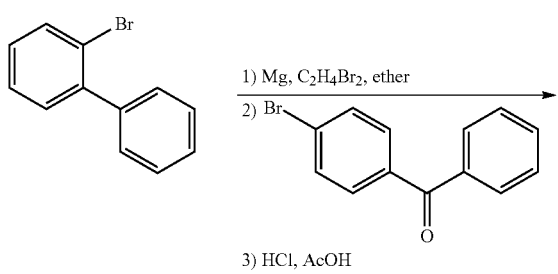

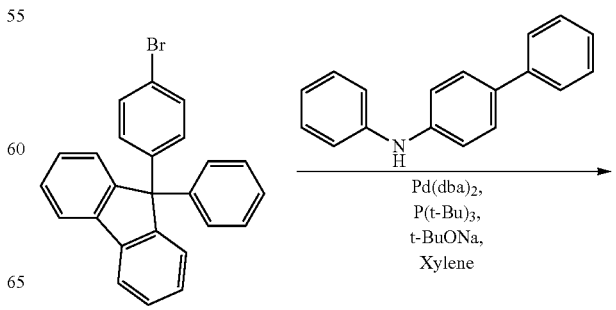

-continued

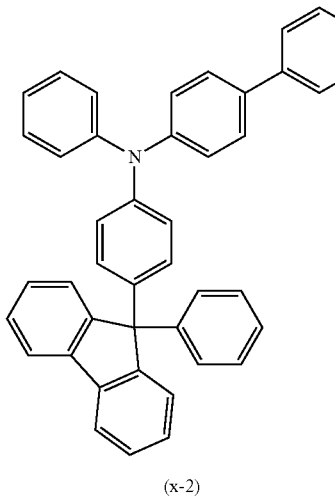

(x-2)

The Rf value of the objective substance by a silica gel thin layer chromatography (TLC) (with a developing solvent of ethyl acetate and hexane in a 1:10 ratio) was 0.41, that of 9-(4-bromophenyl)-9-phenylfluorene was 0.51, and that of 4-phenyl-diphenylamine was 0.27.

The compound obtained in Step 2 above was evaluated by a nuclear magnetic resonance spectrometry ($^1$H-NMR). The measurement data are shown below. The measurement result revealed that the obtained compound was a fluorene derivative BPAFLP. The following shows the $^1$H-NMR data of the obtained substance.

$^1$H-NMR (CDCl$_3$, 300 MHz): δ (ppm)=6.63-7.02 (m, 3H), 7.06-7.11 (m, 6H), 7.19-7.45 (m, 18H), 7.53-7.55 (m, 2H), 7.75 (d, J=6.9, 2H).

Reference Example 2

The synthesis of 2mDBTPDBq-II used in the above Examples is described.

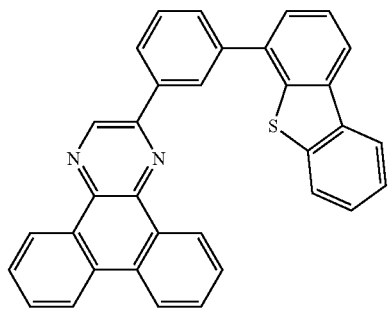

2mDBTPDBq-II

Synthesis of 2mDBTPDBq-II

The synthesis scheme (y-1) of 2mDBTPDBq-II is shown below.

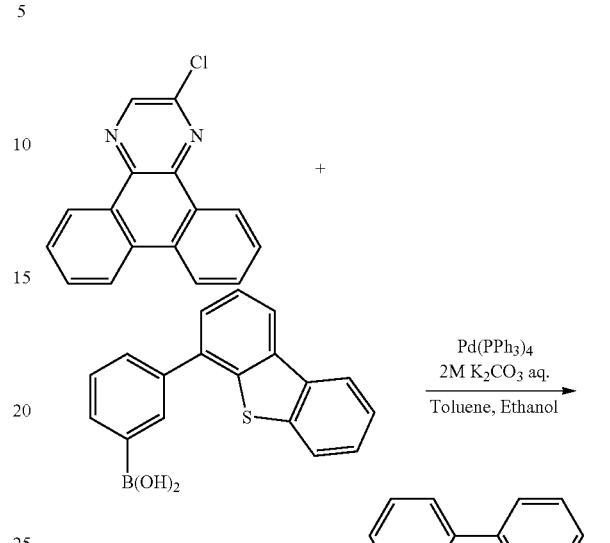

(y-1)

2mDBTPDBq-II

Into a 2-L three-neck flask, 5.3 g (20 mmol) of 2-chlorodibenzo[f,h]quinoxaline, 6.1 g (20 mmol) of 3-(dibenzothiophen-4-yl)phenylboronic acid, 460 mg (0.4 mmol) of tetrakis(triphenylphosphine)palladium(0), 300 mL of toluene, 20 mL of ethanol, and 20 mL of a 2M aqueous solution of potassium carbonate were put. The mixture was degassed by being stirred under reduced pressure, and the air in the three-neck flask was replaced by nitrogen. This mixture was stirred under a nitrogen stream at 100° C. for 7.5 hours. After cooled to room temperature, the obtained mixture was filtered to give a white residue. The obtained residue was washed well with water and ethanol in that order, and then dried. The obtained solid was dissolved in about 600 mL of hot toluene, followed by filtration through Celite and Florisil, whereby a clear colorless filtrate was obtained. The obtained filtrate was concentrated and purification was performed by silica gel column chromatography using about 700 mL of silica gel. The chromatography was carried out using toluene at a temperature of about 40° C. as a developing solvent. Acetone and ethanol were added to the solid obtained after the purification, followed by irradiation with ultrasonic waves. Then, the precipitate was collected by filtration and the obtained solid was dried to give 7.85 g of the objective white powder in a yield of 80%.

By a train sublimation method, 4.0 g of the obtained white powder was purified. In the purification, the white powder was heated at 300° C. under a pressure of 5.0 Pa with a flow rate of an argon gas of 5 mL/min. A portion which was solidified at about 240° C. to 230° C. was recovered to obtain 3.5 g of the objective white powder in a yield of 88%.

A nuclear magnetic resonance spectrometry ($^1$H-NMR) identified this compound as the objective substance 2mDBT-PDBq-II. The following shows the $^1$H-NMR data of the obtained substance.

$^1$H-NMR. (CDCl$_3$, 300 MHz): δ (ppm)=7.45-7.52 (m, 2H), 7.59-7.65 (m, 2H), 7.71-7.91 (m, 7H), 8.20-8.25 (m, 2H), 8.41 (d, J=7.8 Hz, 1H), 8.65 (d, J=7.5 Hz, 2H), 8.77-8.78 (m, 1H), 9.23 (dd, J=7.2 Hz, 1.5 Hz, 1H), 9.42 (dd, J=7.8 Hz, 1.5 Hz, 1H), 9.48 (s, 1H).

Reference Example 3

The synthesis of Ir(tBuppm)$_2$(acac) used in the above Examples is described.

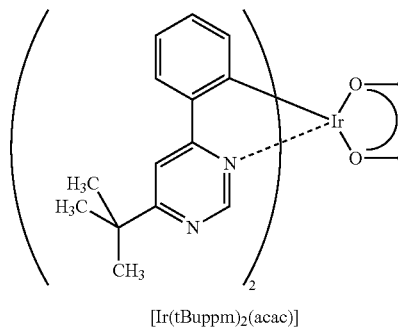

[Ir(tBuppm)$_2$(acac)]

Step 1: Synthesis of 4-tert-butyl-6-phenylpyrimidine (abbreviation: HtBuppm)

The synthesis scheme of Step 1 is shown in (d-1) below.

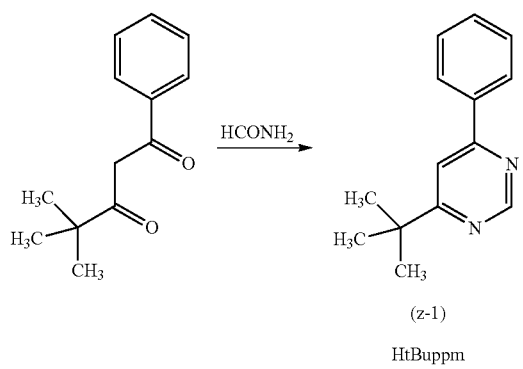

(z-1)

HtBuppm

Into a recovery flask equipped with a reflux pipe, 22.5 g of 4,4-dimethyl-1-phenylpentane-1,3-dione and 50 g of formamide were put, and the air in the flask was replaced by nitrogen. This reaction container was heated, so that the reaction solution was refluxed for 5 hours. After that, this solution was poured into an aqueous solution of sodium hydroxide, and an organic layer was extracted with dichloromethane. The obtained organic layer was washed with water and saturated saline, dried with magnesium sulfate, and filtered. The solvent of the filtrate was distilled off, and then the obtained residue was purified by silica gel column chromatography using hexane and ethyl acetate as a developing solvent in a volume ratio of 10:1, to give a pyrimidine derivative HtBuppm (colorless oily substance, 14% in yield).

Step 2: Synthesis of di-μ-chloro-bis[bis(6-tert-butyl-4-phenylpyrimidinato)iridium(III)] (abbreviation: [Ir(tBuppm)$_2$Cl]$_2$)

The synthesis scheme of Step 2 is shown in (d-2) below.

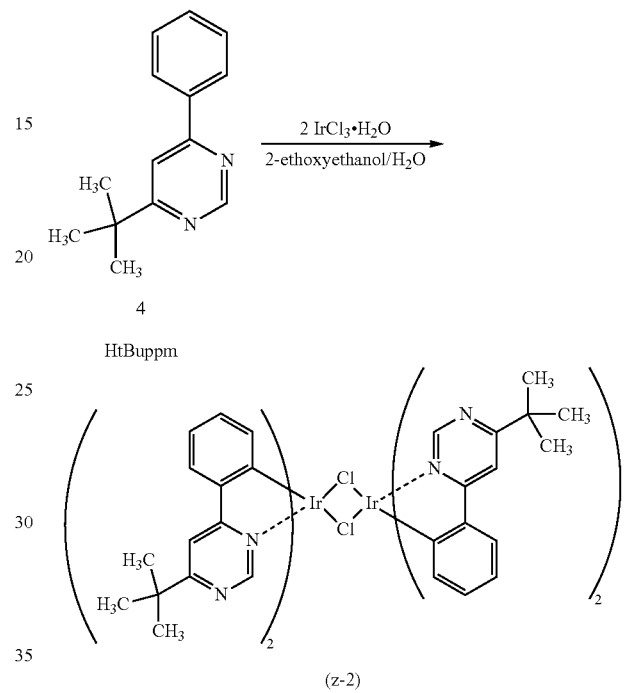

(z-2)

[Ir(tBuppm)$_2$Cl]$_2$

Into a recovery flask equipped with a reflux pipe, 15 mL of 2-ethoxyethanol, 5 mL of water, 1.49 g of HtBuppm obtained in Step 1, and 1.04 g of iridium chloride hydrate (IrCl$_3$.H$_2$O) were put, and the air in the flask was replaced by argon. Then, irradiation with microwaves (2.45 GHz, 100 W) for 1 hour was performed. The solvent was distilled off, and then the obtained residue was suction-filtered and washed with ethanol to give a Binuclear complex [Ir(tBuppm)$_2$Cl]$_2$ (yellow green powder, 73% in yield).

Step 3: Synthesis of Ir(tBuppm)$_2$(acac)

The synthesis scheme of Step 3 is shown in (d-3) below.

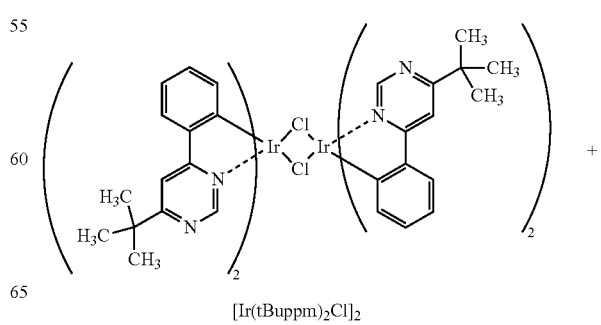

[Ir(tBuppm)$_2$Cl]$_2$

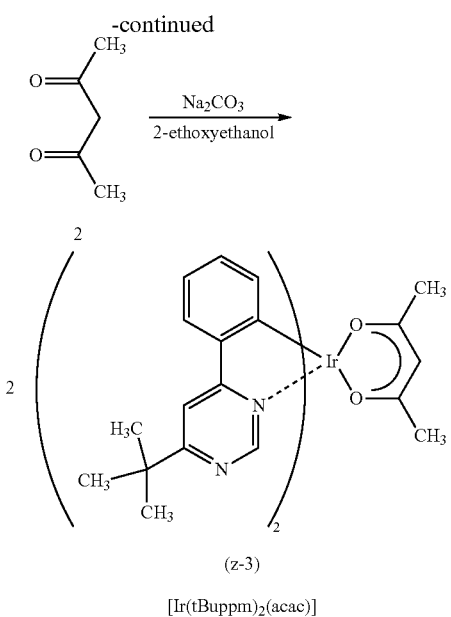

(z-3)

[Ir(tBuppm)₂(acac)]

Into a recovery flask equipped with a reflux pipe, 40 mL of 2-ethoxyethanol, 1.61 g of the dinuclear complex [Ir(tBuppm)₂Cl]₂ obtained in Step 2, 0.36 g of acetylacetone, and 1.27 g of sodium carbonate were put, and the air in the flask was replaced by argon. Then, irradiation with microwaves (2.45 GHz, 100W) for 60 minutes was performed. The solvent was distilled off, and the obtained residue was suction-filtered and washed with water and ethanol. This solid was dissolved in dichloromethane, and the mixture was filtered through a filter in which Celite, alumina, and Celite were stacked in that order. The solvent was distilled off, and the obtained solid was recrystallized with a mixed solvent of dichloromethane and hexane, so that the objective substance was obtained as yellow powder (68% in yield).

An analysis result by nuclear magnetic resonance spectrometry ($^1$H-NMR) of the yellow powder obtained in Step 3 is described below. The result revealed that Ir(tBuppm)₂(acac) was obtained in this synthetic example. The following shows the $^1$H-NMR data of the obtained substance.

$^1$H-NMR. δ (CDCl₃): 1.50 (s, 18H), 1.79 (s, 6H), 5.26 (s, 1H), 6.33 (d, 2H), 6.77 (t, 2H), 6.85 (t, 2H), 7.70 (d, 2H), 7.76 (s, 2H), 9.02 (s, 2H).

EXPLANATION OF REFERENCE

901: lighting device, 903: desk lamp, 904: lighting device, 1101: anode, 1102: cathode, 1103: EL layer, 1103a: EL layer, 1103b: EL layer, 1104: intermediate layer, 1104a: electron-injection buffer, 1104b: electron-relay layer, 1104c: charge production region, 1111: hole-injection layer, 1112: a hole-transport layer, 1113: light-emitting layer, 1114: electron-transport layer, 1115: electron-injection layer, 1400: light-emitting device, 1401: driver circuit portion (source side driver circuit), 1402: pixel portion, 1403: driver circuit portion (gate side driver circuit), 1404: sealing substrate, 1405: sealing member, 1407: space, 1408: wiring, 1409: FPC (flexible printed circuit), 1410: element substrate, 1411: switching TFT, 1412: current control TFT, 1413: electrode, 1414: partition, 1416: EL layer, 1417: electrode, 1418: light-emitting element, 1423: n-channel TFT, 1424: p-channel TFT, 1500: glass substrate, 1501: electrode, 1502: electrode, 1503: EL layer, 1510: light-emitting element, 1511: hole-injection layer, 1512: hole-transport layer, 1513: light-emitting layer, 1513a: light-emitting layer, 1513b: light-emitting layer, 1514a: electron-transport layer, 1514b: electron-transport layer, 1515: electron-injection layer, 2500: light-emitting device, 2501: substrate, 2502: electrode, 2503: electrode, 2504: EL layer, 2505: insulating layer, 2506: partition layer, 7100: television device, 7101: housing, 7103: display portion, 7105: stand, 7107: display portion, 7109: operation key, 7110: remote controller, 7201: main body, 7202: housing, 7203: display portion, 7204: keyboard, 7205: external connection port, 7206: pointing device, 7301: housing, 7302: housing, 7303: joint portion, 7304: display portion, 7305: display portion, 7306: speaker portion, 7307: recording medium insertion portion, 7308: LED lamp, 7309: operation key, 7310: connection terminal, 7311: sensor, 7312: microphone, 7400: cellular phone, 7401: housing, 7402: display portion, 7403: operation button, 7404: external connection port, 7405: speaker, 7406: microphone, 7500: lighting device, 7501: housing, 7503a-7503d: light-emitting device, 9501: lighting portion, 9503: support, 9505: support base.

This application is based on Japanese Patent Application serial no. 2011-091514 filed with Japan Patent Office on Apr. 15, 2011, the entire contents of which are hereby incorporated by reference.

The invention claimed is:

1. A compound represented by a formula (G3):

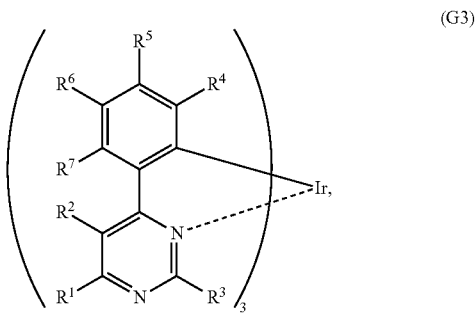

(G3)

wherein $R^1$ to $R^7$ are separately selected from hydrogen, halogen, a substituted or unsubstituted alkyl group having 1 to 4 carbon atoms, a substituted or unsubstituted alkoxy group having 1 to 4 carbon atoms, a substituted or unsubstituted alkylthio group having 1 to 4 carbon atoms, a substituted or unsubstituted haloalkyl group having 1 to 4 carbon atoms, and a substituted or unsubstituted aryl group having 6 to 10 carbon atoms, and wherein at least one of $R^1$, $R^5$, $R^6$, and $R^7$ is an alicyclic hydrocarbon having an intramolecular carbon-carbon bridged bond.

2. The compound according to claim 1, wherein $R^1$ is the alicyclic hydrocarbon.

3. The compound according to claim 1, wherein the alicyclic hydrocarbon is selected from a tricyclo[5.2.1.0(2,6)]decanyl group, a norbornyl group, and an adamantyl group.

4. A compound represented by a formula (G2):

$$\left( \begin{array}{c} R^6 \underset{R^7}{\overset{R^5}{\bigcirc}} R^4 \\ R^2 \underset{R^1}{\overset{}{\bigcirc}} N \\ R^1 \quad N \quad R^3 \end{array} \right)_2 Ir-L,$$

(G2)

wherein $R^1$ to $R^7$ are separately selected from hydrogen, halogen, a substituted or unsubstituted alkyl group having 1 to 4 carbon atoms, a substituted or unsubstituted alkoxy group having 1 to 4 carbon atoms, a substituted or unsubstituted alkylthio group having 1 to 4 carbon atoms, a substituted or unsubstituted haloalkyl group having 1 to 4 carbon atoms, and a substituted or unsubstituted aryl group having 6 to 10 carbon atoms, wherein at least one of $R^1$, $R^5$, $R^6$, and $R^7$ is an alicyclic hydrocarbon having an intramolecular carbon-carbon bridged bond, and wherein L is a monoanionic ligand represented by any of formulae (L1) to (L7):

(L1)

(L2)

(L3)

(L4)

(L5)

(L6)

(L7)

and wherein: $R^{71}$ to $R^{109}$ separately represent any of hydrogen, a substituted or unsubstituted alkyl group having 1 to 4 carbon atoms, a substituted or unsubstituted haloalkyl group having 1 to 4 carbon atoms, and a substituted or unsubstituted alkoxy group having 1 to 4 carbon atoms,; $A^1$ to $A^3$ separately represent any of nitrogen, sp² carbon bonded to hydrogen, and sp² carbon bonded to a substituent R; and R represents any of an alkyl group having 1 to 4 carbon atoms, a haloalkyl group having 1 to 4 carbon atoms, and a phenyl group.

5. The compound according to claim 4, wherein the monoanionic ligand is represented by any of the formula (L1) and (L7).

6. The compound according to claim 4,
wherein the compound is represented by any one of formula (100), (111), and (128):

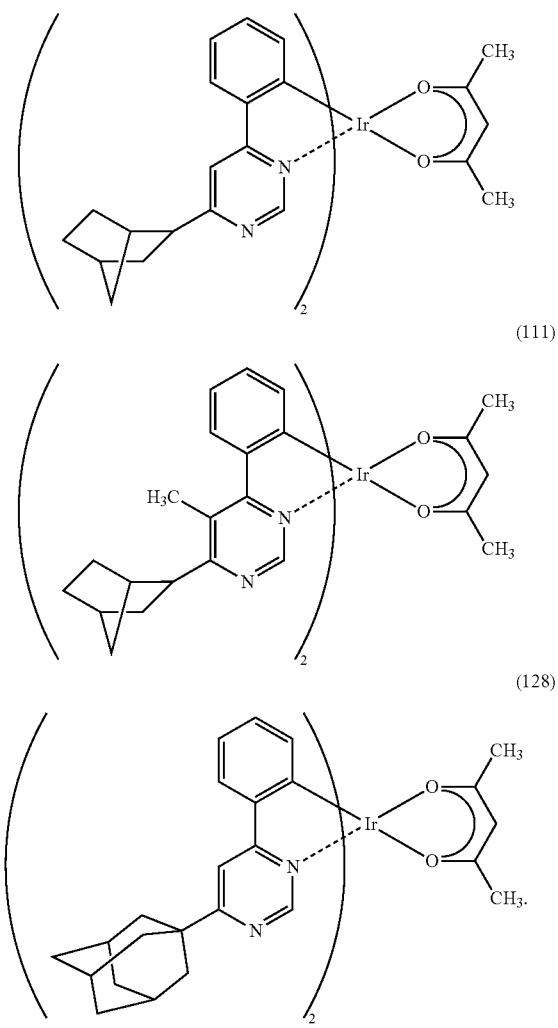

7. The compound according to claim 1,
wherein the compound is represented by a formula (108):

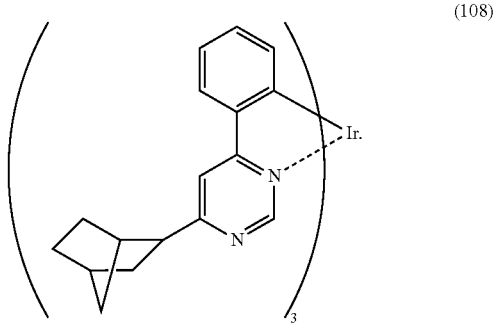

8. The compound according to claim 1,
wherein:

the halogen is fluorine, the substituted or unsubstituted alkyl group is selected from a methyl group, an ethyl group, a propyl group, an isopropyl group, a n-butyl group, a sec-butyl group, an isobutyl group, and a tert-butyl group;

the substituted or unsubstituted alkoxy group is selected from a methoxy group, an ethoxy group, a propoxy group, an isopropoxy group, a n-butoxy group, a sec-butoxy group, an isobutoxy group, and a tert-butoxy group;

the substituted or unsubstituted alkylthio group is selected from a methylsulfanyl group, an ethylsulfanyl group, a propylsulfanyl group, an isopropylsulfanyl group, a n-butylsulfanyl group, an isobutylsulfanyl group, a sec-butylsulfanyl group, and tert-butylsulfanyl group; and the substituted or unsubstituted haloalkyl group is selected from a fluoromethyl group, a difluoromethyl group, a trifluoromethyl group, a 2,2,2-trifluoroethyl group, a 3,3,3-trifluoropropyl group, and a 1,1,1,3,3,3-hexafluoroisopropyl group.

9. The compound according to claim 4,
wherein:

the halogen is fluorine, the substituted or unsubstituted alkyl group is selected from a methyl group, an ethyl group, a propyl group, an isopropyl group, a n-butyl group, a sec-butyl group, an isobutyl group, and a tert-butyl group;

the substituted or unsubstituted alkoxy group is selected from a methoxy group, an ethoxy group, a propoxy group, an isopropoxy group, a n-butoxy group, a sec-butoxy group, an isobutoxy group, and a tert-butoxy group;

the substituted or unsubstituted alkylthio group is selected from a methylsulfanyl group, an ethylsulfanyl group, a propylsulfanyl group, an isopropylsulfanyl group, a n-butylsulfanyl group, an isobutylsulfanyl group, a sec-butylsulfanyl group, and tert-butylsulfanyl group; and the substituted or unsubstituted haloalkyl group is selected from a fluoromethyl group, a difluoromethyl group, a trifluoromethyl group, a 2,2,2-trifluoroethyl group, a 3,3,3-trifluoropropyl group, and a 1,1,1,3,3,3-hexafluoroisopropyl group.

10. The compound according to claim 4,
wherein: $R^{71}$ to $R^{109}$ separately represent any of hydrogen, an alkyl group having 1 to 4 carbon atoms, and an alkoxy group having 1 to 4 carbon atoms; $A^1$ to $A^3$ separately represent any of nitrogen, $sp^2$ carbon bonded to hydrogen, and $sp^2$ carbon bonded to a substituent R; and R represents any of an alkyl group having 1 to 4 carbon atoms and a phenyl group.

11. The compound according to claim 4,
wherein the monoanionic ligand is represented by the formula (L1).

* * * * *

UNITED STATES PATENT AND TRADEMARK OFFICE
CERTIFICATE OF CORRECTION

PATENT NO. : 9,200,022 B2
APPLICATION NO. : 13/446216
DATED : December 1, 2015
INVENTOR(S) : Hideko Inoue et al.

It is certified that error appears in the above-identified patent and that said Letters Patent is hereby corrected as shown below:

In the Specification:

Column 2, Line 45; Change "a carbon" to --α carbon--.

Column 5, Line 9; Change "provided:" to --provided.--.

Column 5, Line 19; Change "having," to --having--.

Column 8, Line 1; Change "et-carbon" to --α-carbon--.

Column 9, Line 4; Change "vacuum-evaporation" to --vacuum evaporation--.

Column 13, Line 56; Change "(TZO)," to --(IZO)--.

Column 14, Line 62; Change "property;" to --property,--.

Column 16, Line 4; Change "N",N",N''',N''',Nm-octaphenyldibenzo" to --N",N",N''',N'''-octaphenyl--.

Column 16, Line 36; Change "9-yl]ethenyl}" to --9-yl)ethenyl]--.

Column 17, Line 46; Change "$10^{-6}$/V·s" to --$10^{-6}$ cm$^2$/V·s--.

Column 23, Line 16; Change "$R^6$ and $R^7$," to --$R^6$, and $R^7$,--.

Column 27, Line 65; Change "G Morlock," to --G. Morlock,--.

Column 49, Line 67; Change "Ruined" to --formed--.

Column 50, Lines 40; Change "polyvinyl" to --poly(vinyl--.

Column 58, Line 39; Change "nato](endo" to --... nato]iridium(III) (endo--.

Column 59, Lines 16-17; Change "1.2 in A/cm$^2$," to --1.2 mA/cm$^2$--.

Column 60, Line 15; Change "thereof" to --thereof.--.

Column 60, Line 48; Change "6phenylpyrimidine" to --6-phenylpyrimidine--.

Column 62, Line 41; Change "(IrCl$_3$.H$_2$O)" to --(IrCl$_3$·H$_2$O)--.

Column 67, Line 56; Change "In. FIG. 18," to --In FIG. 18,--.

Signed and Sealed this
Nineteenth Day of April, 2016

Michelle K. Lee
*Director of the United States Patent and Trademark Office*

CERTIFICATE OF CORRECTION (continued)
U.S. Pat. No. 9,200,022 B2

In the Specification:

Column 68, Lines 64 to 65; Change "formula (III)" to --formula (111)--.

Column 70, Line 53; Change "iridium(II)}" to --iridium(III)}--.

Column 70, Line 59; Change "(IrCl$_3$.H$_2$O)" to --(IrCl$_3$·H$_2$O)--.

Column 73, Line 9; Change "formula (III)" to --formula (111)--.

Column 73, Line 9; Change "formula (III)" to --formula (111)--.

Column 76, Line 9; Change "(IrCl$_3$.H$_2$O)" to --(IrCl$_3$·H$_2$O)--.

Column 84, Line 42; Change "(IrCl$_3$.H$_2$O)" to --(IrCl$_3$·H$_2$O)--.

Column 84, Line 47; Change "Binuclear" to --dinuclear--.

In the Claims:

Column 88, Line 67, Claim 5; Change "formula" to --formulae--.

Column 89, Lines 2 to 3, Claim 6; Change "formula" to --formulae--.